United States Patent [19]
Descales et al.

[11] Patent Number: 6,070,128
[45] Date of Patent: *May 30, 2000

[54] METHOD FOR DETERMINING PROPERTIES USING NEAR INFRA-RED (NIR) SPECTROSCOPY

[75] Inventors: Bernard Descales, Marseilles; Didier Lambert, Saint-Mitre-les-Remparts; Jean-Richard Llinas, Marseille; Andr´´Martens, Chateauneuf les Martigues; Sebastien Osta, Istres; Michel Sanchez; Sylvie Bages, both of Lavera, all of France

[73] Assignee: Eutech Engineering Solutions Limited, Cheshire, United Kingdom

[*] Notice: This patent is subject to a terminal disclaimer.

[21] Appl. No.: 08/838,879

[22] Filed: Apr. 9, 1997

Related U.S. Application Data

[63] Continuation-in-part of application No. 08/465,680, Jun. 6, 1995, Pat. No. 5,712,797, which is a continuation-in-part of application No. 08/467,179, Jun. 6, 1995, Pat. No. 5,763,883, which is a continuation-in-part of application No. 08/465,920, Jun. 6, 1995, Pat. No. 5,740,073.

[30] Foreign Application Priority Data

Apr. 9, 1996 [EP] European Pat. Off. .............. 96430003

[51] Int. Cl.$^7$ .................................................... G01N 31/00
[52] U.S. Cl. ......................... 702/30; 702/27; 250/339.09
[58] Field of Search .................. 702/30, 27; 364/528.01, 364/528.03; 250/339.07–339.09

[56] References Cited

U.S. PATENT DOCUMENTS

| | | | |
|---|---|---|---|
| 5,446,681 | 8/1995 | Gethner et al. | 702/27 |
| 5,452,232 | 9/1995 | Espinosa et al. | 702/30 |
| 5,475,612 | 12/1995 | Espinosa et al. | 702/30 |
| 5,712,797 | 1/1998 | Descales et al. | 702/30 |
| 5,740,073 | 4/1998 | Bages et al. | 702/30 |
| 5,763,883 | 6/1998 | Descales et al. | 250/339.09 |

OTHER PUBLICATIONS

O. U. Anders, "Ratio Matching—A Statistical Aid for Discovering Generic Relationships among Samples," *Analytical Chemistry* (Oct. 1972), 44, pp. 1930–1933.

C. W. Brown, et al., "Infrared Analysis of Weathered Petroleum Using Vacuum Techniques," *Analytical Chemistry* (Jan. 1976), 48, pp. 191–195.

A. J. Martens, et al., "Test Olefin Feed by Micropyrolysis," *Hydrocarbon Processing* (Apr. 1979), pp. 199–202.

J. J. Royer, "Proximity Analysis: A Method for Multivariate Geodata Processing, Application to Geochemical Processing," *Sci. Terre, Serl: Inf. Geol.* (Apr. 1984), 20, pp. 223–243.

(List continued on next page.)

*Primary Examiner*—Marc S. Hoff
*Assistant Examiner*—Bryan Bui
*Attorney, Agent, or Firm*—Fay, Sharpe, Fagan, Minnich & McKee, LLP

[57] ABSTRACT

A method of determining or predicting a value $P_x$ of a property (e.g. octane number) of a material X or a property of a product of a process from the material or yield of the process for example a blending, separation, or chemical (e.g. polymerization) process, which method comprises measuring the absorption $D_{ix}$ of the material at more than one wavelength in the region 600–2600 nm, comparing the the signals indicative of the absorptions or a derivative thereof with signals indicative of absorptions $D_{im}$ or derivatives thereof at the same wavelength for a number of standards S in a bank for which the property or yield P is known, and choosing from the bank at least one standard $S_m$ with property $P_m$ the standard having the smallest average value of the absolute difference at each wavelength i between the signal for the material and the signal for the standard $S_m$ to obtain $P_x$, with averaging of the properties or yields $P_m$ when more than one standard $S_m$ is chosen. If desired the method can be used as such to control the process by comparison of $P_m$ with the desired value and adjustment of the process to minimize deviations from $P_m$; in an alternative process the signal (or function thereof) of the standard(s) with the smallest average value of the absolute difference may be used directly to control the process.

46 Claims, 3 Drawing Sheets

OTHER PUBLICATIONS

H. A. M. Rasheed, et al., "Identification of Petroleum Products by the Ratio Matching Method," *Journal of Petroleum Research* (1986), 5, pp. 1–17.

M. A. Puskar, et al., "Infrared Screening Technique for Automated Identification of Bulk Organic Mixtures," *Analytical Chemistry* (Aug. 1986), 58, pp. 1981–1989.

H. A. M. Rashid, et al., "Gasoline Analysis Using Gas Liquid Chomatography and Ratiomatching for Quality Control," *Journal of Petroleum Research* (1988), 7, pp. 169–179.

B. Descales, et al., "Determination of Research and Motor Octane Numbers (RON and MON) of Gasolines by the Near Infra Red (NIR) Method," *Pet. Tech.* (1989), 349, pp. 2–8.

H. A. Rashid, et al., "Determination of Several Physical Properties of Light Petroleum Products Using IR," *Fuel Science and Technology Int'l.* (1989), 7, pp. 237–250.

A. Martens, et al., "NIR Process Control of a Steam Cracker," *Int. Conf. Near Infrared Spectrosc.* (1991), pp. 447–481.

S. Kokot, et al., "Application of FT–IR Spectroscopy for the Prediction of Properties of Australian Refined Petroleum Products," *Proc. SPIE–Int. Soc. Opt. Eng.* (1992), 1575, pp. 195–196 495–498.

J. M. McDonald, et al., "Gasoline Blending Using NIR Spectroscopy and LP Optimization," *NPRA Computer Conf.* (1992), CC–92–137, pp. 1–9.

S. J. Swarin, et al., "Predicting Gasoline Properties Using Near–IR Spectroscopy Beyond Octane Numbers and Hydrocarbon Classes," *Spectroscopy* (Sep. 1992), 7, pp. 42–49.

B. Descales, et al., "Analyse en ligne sur des unités pétrochimiques par spectrophotométrie proche infrarouge," *Analysis* (1993), 23, pp. M25–M28.

I. Cermelli, et al., "On Line Near Infrared Analysis Applications in Petrochemistry," *Near Infrared Spectroscopy*, Harwood, New York, (1992), pp. 395–400.

S. M. Maggard, et al., "The Advantage of Blending Reformulated Fuels Using Near Infrared Octane and Combustion Analysis with Closed Loop Feedback," *Proc.–Annu. Symp. Instr. Process Ind.* (1993), 48, pp. 61–67.

J. Workman, Jr., "A Review of Process Near Infrared Spectroscopy: 1980–1994," *Near Infrared Spectrosc.* (1993), 1, pp. 221–245.

J. Coates, "New Analyser Technology to Monitor Refinery Unit Production Efficiency," *Hydrocarb. Technol. Int.* (1994), pp. 193–197.

T. Zerlia, "Spettroscopia del vicino infrarosso (NIR) per l'esame di prodotti proliferi," *Riv. Combust.* (Sep. 1994), 48, pp. 349–354.

Y. Yamamoto, et al., *Idemitsu Giho* (1994), 37, pp. 608–615.

D. Lambert, et al., "Optimize Stream Cracking with Online NIR Analysis," *Hydrocarbon Processing* (Dec. 1995), pp. 103–108.

METHOD FOR DETERMINING PROPERTIES USING NEAR INFRA-RED (NIR) SPECTROSCOPY

CROSS-REFERENCES TO RELATED APPLICATIONS

This application is a continuation-in-part of the following applications: Ser. No. 08/465,680 filed Jun. 6, 1995, now U.S. Pat. No. 5,712,797 and Ser. No. 08/467,179 filed Jun. 6, 1995, now U.S. Pat. No. 5,763,883 and Ser. No. 08/465,920 filed Jun. 6, 1995, now U.S. Pat. No. 5,740,073.

STATEMENT REGARDING FEDERALLY SPONSORED RESEARCH OR DEVELOPMENT

Not applicable

REFERENCE TO MICROFICHE APPENDIX

Not applicable

BACKGROUND OF INVENTION

1. Field of Invention

This invention relates to a method of determining or predicting by near infra red (NIR) spectroscopy properties of feeds or products and/or yields in physical or chemical processes or separations, in particular involving hydrocarbons, especially in hydrocarbon refineries or for lubricant uses, or chemical processes including polymerisation. The invention also relates to control of such processes.

2. Description of Related Art

NIR spectroscopy has many advantages over other methods of analysis e.g. in refineries and can cover a large number of repetitive applications accurately, quickly and on line. The NIR region between 800 and 2500 nm contains the totality of molecular information in the form of combinations and overtones from polyatomic vibrations, but Mathematical techniques are needed to exploit this information and to calculate the desired parameters. U.S. Pat. No. 5,490,085 (issued Feb. 6, 1996), U.S. Pat. No. 5,452,232 (issued Sep. 19, 1995) and U.S. Pat. No. 5,475,612 (issued Dec. 12, 1995), the disclosure of which is hereby incorporated by reference, describe the use of NIR for determining octane number of a product, or determining yields and/or properties of a product of a chemical process in a refinery or separation process from analysis on the feeds to that process, and yields and/or properties of a product of a blending operation again from analysis on the feed thereto.

At present, numerical methods described for modelling physicochemical properties based on NIR spectra are all of a correlative nature and involve relations of a regressional character between the property(ies) studied. Among these multivariable analyses are multilinear regression (MLR), Principle Component Regression (PLR), Canonic regression, and regression by Partial Least Squares (PLS). In all cases there is sought between the property and the NIR spectrum a relation which may be linear but is usually quadratic or of higher algebraic form involving regression coefficients applied to each absorption. The establishment of any regression requires a progressive calibration, as the approach is empirical and not supported by a theory.

These techniques have disadvantages, the chief of which is the need for establishing a strong correlation between the spectrum and the property, and their difficulty in dealing with positive or negative synergy between components contributing to that property. For example for determining chemical composition e.g. LINA (linear, isoparaffin, Naphthenic, Aromatics) in a hydrocarbon feed to a catalyst reformer, a PLS technique based on the NIR spectra has been described for use. The model works well on the calibration set but the response of the models when pure hydrocarbons are added e.g. cyclohexane is not satisfactory, as the model predicts changes in isoparaffins and naphthenes the reverse of that found experimentally Furthermore there are other practical difficulties, mainly in the need to identify samples of families having the same kind of relation between the spectra and the properties to be modelled. Thus the model may be limited especially with a non linear relation between spectrum and property. Especially when at the edges of the available data the accuracy of the model diminishes. The stability of the model is also a problem, as is the need when adding new standards to do laborious revisions to give the new model, especially when adjusting to a new feedstock for a process; thus testing 6 properties on 4 products leaving a distillation unit requires 24 models, each of which has to be changed for each change of the feed not included in the calibration.

We have discovered a new approach avoiding the above problems with correlations, and regression calculations, and being capable of being expanded automatically with use of a new product of different quality.

BRIEF SUMMARY OF THE INVENTION

The present invention provides a method of determining or predicting a value Px, of a property of a material X or a property of a product of a process from said material or yield of said process, which method comprises measuring the absorption $D_i x$ of said material at more than one wavelength in the region 600–2600 nm, comparing signals indicative of said absorptions or mathematical functions thereof with signals indicative of absorptions $D_i m$ at the same wavelengths or mathematical functions thereof for a number of standards S in a bank for which the said property or yield P is known, and choosing from the bank at least one and preferably at least 2 standard $S_m$ with property $P_m$, said standard $S_m$ having the smallest average values of the absolute values of the difference at each wavelength i between the signal for the material and the signal for the standard $S_m$ to obtain value $P_x$, and with averaging of said properties or yields Pm, when more than 1 standard $S_m$ is chosen.

The present invention also provides a method of controlling a process for which a material X is a feed or a product, in order to keep substantially constant the value $V_c$ of a property P of said product or the product of said process from said feed, or the yield of said process, which method comprises measuring the absorption $D_{ix}$ of said material at more than one wavelength in the region 600–2600 nm, comparing signals (i) indicative of said absorptions or a mathematical function thereof with signals (ii) indicative of absorptions $D_{im}$ at the same wavelengths or a mathematical function thereof for at least 2 standards $S_m$ for which the said property or yield has a known value V, at least one of said standards $S_{mc}$ having a value $V_c$ for said property or yield and controlling said process to ensure that said standard $S_{mc}$ or standard(s) $S_{mc}$ is the standard or standards having the smaller or smallest average value of the absolute difference at each wavelength i between the signal for said material and the signal from the standard $S_m$.

This method can also be performed without determining said property or yield of said process before controlling the process.

The above methods can be performed without regression or correlation techniques, e.g. between the absorption at any wavelength of the material and the property/yield.

BRIEF DESCRIPTION OF THE SEVERAL VIEW OF THE DRAWINGS

DETAILED DESCRIPTION OF THE INVENTION

Figure 1:
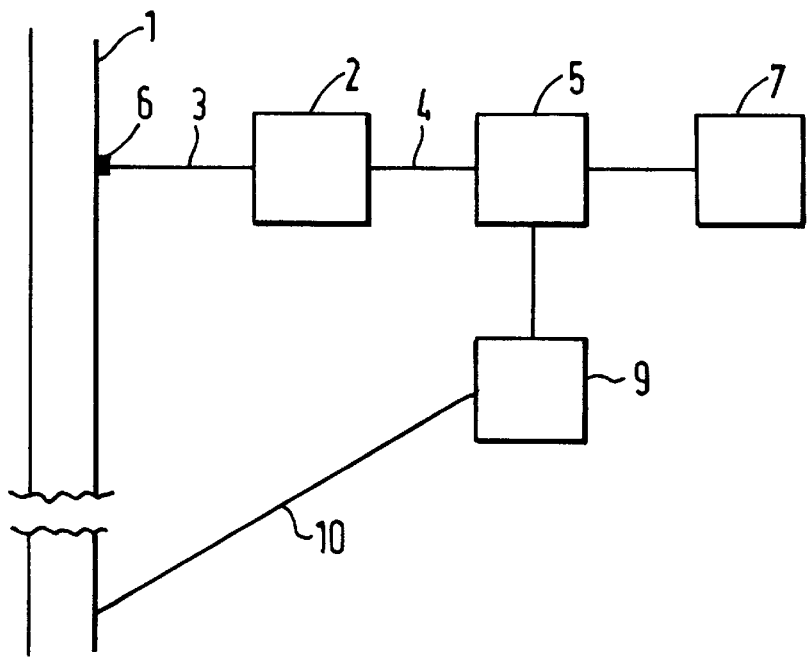
FIG. 1 represents a schematic diagram showing an apparatus for use in the invention.

In FIG. 1, an optical fibre 3 links a spectrometer 2 and a probe 6 in or at process line 1. The spectrophotometer 2 produces absorbance signals at more than 1 wavelength, which signals as such (or after mathematical treatment to form e.g. derivative signals) are passed via line 4 to computer 5, where the signals as such or after conversion e.g. to one or more derivative signals, are used to enable the computer to access the databank 7 of standard signals e.g. absorptions and properties/yields therein. The signals are compared to those of one or more standard absorption(s) as described above and its/their corresponding property(ies) or yield(s). The output of the computer 5 is in the form of a property of the material in line 1 or yield or property of product of the process from that material and may be printed in hard copy. Preferably, however, the output property/yield is used to control the process involved with the product in line 1, i.e. for which line 1 is a feed or a product line; in this case the computer 5 is linked to and instructs the controller 9 which, via 10, controls that process e.g. via valves/temperature and/or pressure controls in line 1 or in relation to line 1. By this means the property of material in line 1 or yield or property of product of the process from that material can be optimized. Alternatively, the output of the computer 5 is in the form of a signal which is used to control the process involved with the product in line 1, i.e. for which line 1 is a feed or a product line; in this case the computer 5 is linked to and instructs the controller 9 which, via 10, controls that process e.g. via valves/temperature and/or pressure controls in line 1 or in relation to line 1. By this means the property of material in line 1 or yield or property of product of the process from that material can be kept substantially constant without the need to determine the property or yield.

Figure 2:
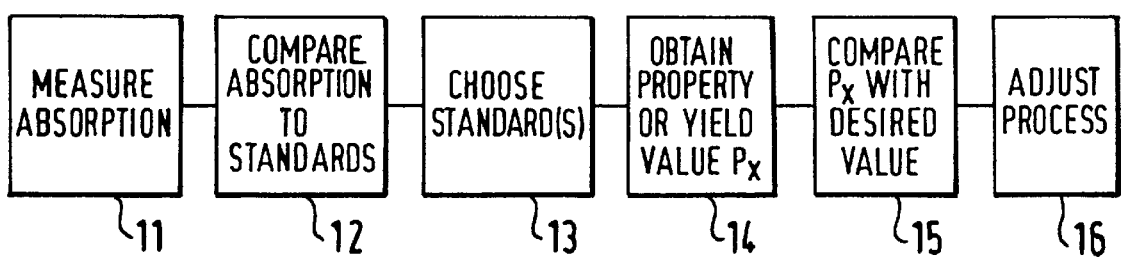
FIGS. 2 and 4 represent schematic diagrams for the method of the invention; and, FIG. 3 is a read out from a computer analyzing NIR data.

In FIG. 2, the initial operation 11 is to measure the absorption of the unknown, after which in the second step 12, the absorptions are compared to absorptions in spectra of standards, and in the third step 13, the spectra of the standards Sm are chosen according to criteria described above, and then in step 14, the property(ies) of the standard (s) Sm chosen is used to obtain the desired property or yield. If the spectrum of only 1 standard Sm is chosen, then the value $P_x$ of the unknown is the same as that of that standard Pm. If more than 1 spectrum is chosen, the value $P_x$ of the unknown is the average of the values Pm of the standards. If desired in an optional step 16, the value $P_x$ is compared to the desired value for the unknown and in step 16 the process involving the unknown is adjusted to make the value $P_x$ the same as the desired value.

Figure 4:
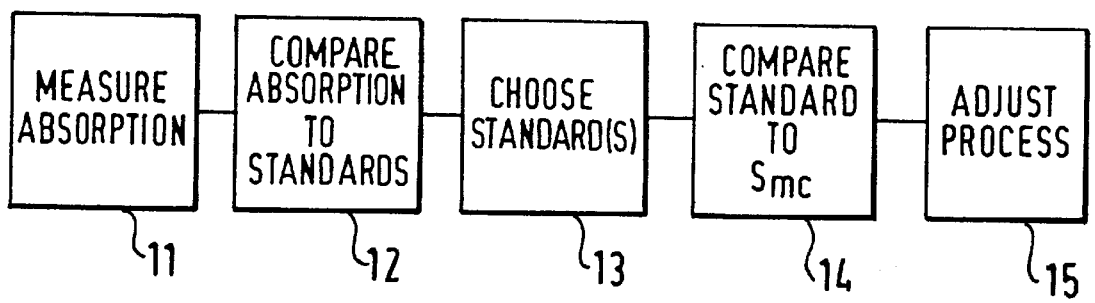

In FIG. 4, steps 11, 12 and 13 are as in FIG. 2 but then in step 14, if the standard $S_m$ chosen is not $S_{mc}$, in step 15 the process involving the unknown is adjusted to keep the standard chosen to be $S_{mc}$ and hence to keep the value of the property or yield substantially constant.

Thus for the performance of the method of the invention, a bank is prepared in which the NIR spectra are recorded at many wavelengths for a large number of standard materials, together with their properties (or those of products obtained by processes therefrom) determined by alternative techniques e.g. gas chromatography for chemical compositions and yields determined by known methods or viscosities by known mechanical methods. The standards are chosen to cover the area in which the method is to be used, so for octane number determination, a range of gasolines can be chosen of widely varying octane numbers, with e.g. different contents of lead, or other additives such as alkyl ethers and aromatics. For the determination of properties of polyethylenes a range of polyethylenes is chosen of widely varying properties, e.g. with different contents of comonomer, or other properties such as molecular weight. For viscosity determinations for base oils, a range of base oils is chosen of widely varying viscosities. The number of wavelengths chosen may be 2–1000 e.g. 5–200 or 10–20 such as 40–80 especially for oil refining/petrochemical operations as described below, or 5–100 or 10–80 such as 25–65 especially for use with processes which are polymerisation, oligomerisation or an organic reaction in which at least one of the reactant and a product is a functionalised compound, or 10–80 such as 40–70 especially where material X is a composition comprising part of a lubricating oil fraction from a distillation of oil. The number of standards can be at least 100 or 1000, or 100,000 up to 5 million depending on property(ies) chosen.

The wavelengths chosen may be at regular intervals such as each 1–50 or 10–50 (especially for such processes like polymerisation oligomerisation and reaction as described above) or 15–35 nm (or each 1–5 nm or each nanometer) or may be at irregular intervals e.g. with intervals of 1–200 nm e.g. 1–100 or 1–50 such as 2–50 or 4–50 or 10–60 nm, which may be random or chosen because of a change in the shape of the spectral curve at that wavelength e.g. a peak, trough or shoulder or chosen by chemical or statistical criteria such as factor analysis. The wavelengths may be in the region 600–2600 nm, such as 800–2600 nm, in particular 1500–2600 or 2000–2550 nm, especially for oil refining/petrochemical operations as described below or 800–2600 eg 800–2000 especially 1000–1800 nm or 2000–2550 nm for diene containing gasolines such as ones produced by cracking e.g. steam cracking. The wavenumbers may be in the region 16,600–3840cm$^{-1}$, e.g. 12,500 to 3840cm$^{-1}$ in particular 6660–3840 or 5000–3900cm$^{-1}$, or 12500 to 3840 12500–5000 especially 10000–5500 or 5000–3900cm$^{-1}$ especially for oil refining/petrochemical operations as described below; corresponding frequencies in Hertz can be obtained by multiplying these wavenumbers by 3×10$^{10}$cm/sec. Wavelengths may also be in the region 600–2500 nm, e.g. 900–2500 nm such as 1000–2000 nm, while the wavenumbers may be 16,600–4000 cm$^{-1}$ such as 11000–4000 or 10000–5000 cm$^{-1}$, both in particular for the polymerisation, oligomerisation or organic reactions described above and below. Wavelengths may also be in the region 600–2600 nm, e.g. 1000–2500 nm but preferably 1500–2600 or 2000–2550 nm, while the wavenumbers may be 16,600–3840cm$^{-1}$, e.g. 10000–4000cm$^{-1}$ e.g. 6660–3840cm$^{-1}$ or 5000–3900cm$^{-1}$, especially for processes in which material X is a composition comprising part of a lubricating oil fraction from the distillation of oil.

The signals eg absorptions (or derivatives) for the unknown sample are compared with the signals eg absorptions (or derivatives) at the same wavelength of the standards, and those standards chosen having the smallest differences. The properties of those chosen standards are then averaged to determine the property of the unknown sample. The absorptions at more than one wavelength may be chosen, e.g. 2–1000 such as 5–100 or 10–20. Other methods of signal processing apart from derivatives such as Fourier transformation may be used in a similar way. The process can be controlled so that at least one of the standards chosen in one Smc having the desired value Vc for the property or yield.

In the method of the invention the standards chosen are those with the smallest average values of the absolute difference at each wavelength i between the signal exemplified by absorption/optical density (or a derivative thereof) $D_{ix}$ for the unknown material and the corresponding signal eg absorption/optical density (or derivative thereof) $D_{im}$ for the standard. The averages may be in respect of the mean value of $D_{ix}-D_{im}$ (whatever its sign i.e. absolute difference), or $(D_{ix}-D_{im})^2$ and may be the simple mean value or the differences may be weighted to take account of the different sensitivity of the absorption to the property at that wavelength or the different sensitivity of the spectrometer at that wavelength. For each standard in the bank of standards for the type of material in question, the average difference is found as described and the standard or standards with the smallest average differences chosen, e.g. at least 1 but preferably at least 2 such as upto 1000 smallest such as 1 (or 2)–100 or 1 (or 2)–20 but is particular 1 (or 2)–10 and especially 2–6 smallest. Advantageously the average differences chosen and hence the standard (or standards) $S_m$ chosen for the property or yield wanted are such that in relation to the unknown material X and each chosen standard $S_m$ the following functions is met when $i_{xm} < i_{min}$ then $P_x - P_m \leq$ experimental error in P where $P_x$ is property of unknown X, $P_m$ is property of chosen standard $S_m$, $i_{xm}$ is defined by $i^2(xm) = \Sigma(D_{ix}-D_{im})^2$ and the $i_{min}$ is defined by the proximity index, which is the minimum value in relation to 2 standards Sa and Sb with properties $P_a$ and $P_b$ for which $P_a - P_b < E\sqrt{2}$, where E is the experimental error in determining said property or yield in the standard. The value $P_x$ of the property or yield is the same as property or yield $P_m$ or the average $P_m$ if more than one standard $S_m$ is chosen. If more than one standard $S_{mc}$ meets the proximity index function, then the average of the $S_{mc}$ values usually corresponds to the desired value $V_c$, especially the arithmetic means, but optionally with averaging. In a modification of the method of this invention the signals (ii) are indicative of absorptions $D_{im}$ at the same wavelength or a mathematical function thereof of one standard $S_{mc}$ having the known value $V_c$ of said property or yield and controlling said process to ensure that the above function is met.

In order to aid the choice of the appropriate standards, especially in relation to a large number of wavelengths for a complex unknown mixture, it is preferred to limit the choice to those defined by means of a minimal index. For the chosen standard the minimal index is at least the same as the differences between the absorptions of the unknown and the standards. Mathematically, this may be expressed as $i^2ab \leq i^2M$ where iM is the minimal index for the property, and iab is a measure of the deviation (called the proximity index) at all the chosen wavelengths between absorption of the unknown and a chosen standard b. That measure is defined by $$i(ab)^2 = \Sigma_i(D_{ia}-D_{ib})^2 \qquad (1)$$

where $D_{ia}$ is the optical density (or absorbence) of unknown a at wavelength i (or a derivative thereof e.g. a first, second or third derivative of that density), and $D_{ib}$ is the optical density (or absorbence) of standard b at that wavelength i (or a derivative thereof e.g. a first, second or third derivative of that density). The value of $D_1$ is the optical density or the optical density difference with respect to the baseline of the spectrum at that wavelength, or the baseline interpolated between 2 wavelengths on either side thereof. If desired signals corresponding to other mathematical functions of the absorption eg after Fourier transformation or spectral subtraction or division may be used to provide corresponding proximity and Minimal Indices.

If desired instead of the optical density $D_i$ a normalized density $W_i$ may be used where $W_i = D_i/\Sigma D_i$. This normalization avoids errors due to small electronic fluctuations in the apparatus and compensates for small differences in the optical path between the optical cells. In this case the proximity index is defined by $$I(ab)^2 = \Sigma_i(W_{ia}-W_{ib})^2 \qquad (2)$$

The indices can be weighted as desired for increasing resolution. One approach is to define the indices as follows.

$$l(ab)^m = \Sigma Abs \text{ value } (X_{ia}-X_{ib})^m/\sigma_i^n \qquad (3)$$

where $X_i$ is $D_i$ or $W_i$ or a mathematical combination thereof, $\sigma_i$ is the standard deviation of X for the set of samples considered (at that wavelength) and each of m and n which are the same or different is weighting factor which is positive but can be a whole number or a fraction. Other variants can be used with other weighting factors such as those involving the spectral experimental error $e_i$; where $e_i$ is the reproducibility of the spectral measurement at wavelength i. The choice between the different options for the weighted indices may be dictated by numerical efficiency.

The reproducibility of the experimental measurements in the standards may be at least 90% or 94% or 95%. The minimal index may be obtained from a reference standard samples set according to the following procedure, hereafter called the Minimal Index Procedure. The NIR spectra for 2 standard samples A and B and their property P e.g. Octane Number, or viscosity e.g. for a polymer, or density e.g. for a lubricating oil fraction are determined. By means of equation (1), (2) or (3), the value of the proximity index $i_{ab}$ is determined via the absorptions at a series of wavelengths; this index is applicable to the difference in properties $P_a - P_b$ called $EP_{ab}$.

This process is repeated with other pairs of standards c and d, e and f etc to obtain a series of Proximity Indices $i_{cd}$ etc with corresponding property differences $EP_{cd}$ etc. For different values of a parameter L which is greater than the indices $i_{ab}$ etc, the corresponding values of $EP_{ab}$ etc are averaged to give an average $EP_{ij}$ for that value of L; the different values of $EP_{ij}+t\sigma/\sqrt{K}$ are then plotted on a graph against L $\sigma$ is the accuracy of the property determination and K is the number of pairs of samples for which $i_{ab}$ is inferior to a given L. t is the Student factor at a given level of confidence. The intercept is then measured between the curve obtained and a line usually horizontal which is the reproducibility of the property level at an appropriate confidence interval e.g. 90% or more usually 95%; the abcissa portion of the intercept gives the minimal index $i_{min}$, which is the minimum value of $i_{ab}$ for which $P_a = Pb$ within the frame of experimental error.

From this minimal index by Procedure 1, the standards can be chosen which have values of $i^2_{ab} \leq i^2_{min}$ where in this case a is the unknown and b is a standard, as in this case the difference between Property or yield a and Property or yield b is less than or equal to σ√2, where σ is the experimental error in measuring the property. Then from the property P value or values of the chosen standard, the property of the unknown is obtained directly or by averaging those values, usually the arithmetic means, but optionally with weighting. If the standard meeting the requirement is Smc with property or yield value $V_C$, the process is under control, but if a different standard is nearest to the unknown then process needs adjustment as described below.

The method of the invention may be used to determine more than one Property P at once or the process may be controlled to keep substantially constant more than 1 property P at once, in either case e.g. at least 2, such as 1–30 e.g. 2–10 properties at once. Each property of the standards has a particular unweighted, minimal index, which may lie in the region $0-10^{-10}$ e.g. $10^{-1}$ to $10^{-9}$ or $10^{-2}$ to $10^{-8}$, in particular $10^{-7}$ (or $5 \times 10^{-7}$) to $5 \times 10^{-4}$ for Minimal Indices derived from absorbencies; corresponding Minimal Indices may be obtained for other signals/functions. If the Minimal Index chosen is the smallest for all the properties desired, then the same one may be used for all the properties and the standards chosen will be suitable for all the properties. The Minimal Index for each property may be used separately, with different numbers of standards chosen for each property (assuming different Minimal Indices). If desired the same Minimal Index may be used, which is not the smallest, resulting in some of the chosen standards (with a higher Minimal Index) giving some properties of high accuracy and some (with a lower Minimal Index) giving some properties of less high accuracy.

The property to be determined or the value of the property or yield to be controlled may be of the sample being analyzed or a product obtained from that sample e.g. a product of blending, cracking, separating or polymerising the samples, as the property value obtained is derived from the standards, and they will have been determined as needed for the eventual use. Our U.S. Pat. No. 5,452,232 and U.S. Pat. No. 5,475,612 referred to above described such techniques when applied to use of NIR with correlation to blending, separating or cracking operation; the same principles apply in the present method.

If the density of the standards in the data bank is sufficient to have $i^2 ab \leq i^2$ min as is usually the case, the above procedure is very satisfactory. But there are occasions when the bank is incomplete, because of shortage of data of properties in a particular area i.e. a low density of standards or the sensitivity of the property to changes in absorption is so small, that a very small Minimal Index is required and there may be few standards with proximity indices meeting it. It is possible simply choose a larger Minimal Index with e.g. 1–5 times such as 1.5–2 times the Minimal Index; the results may be less accurate than those from a smaller minimal index.

However, a more accurate approach with a low density of standards involves a special densification process of Procedure 2, in which random or semi random densification of the neighbourhood of the unknown is achieved by generation of synthetic standards, based on standards already in the bank. Each new synthetic standard may be obtained from combinations of standards taken at random from the bank but preferably it is obtained from the other standards by the constraint of choosing only a mixture of N standards for which $$(\text{Min})C_j - u_j \leq C_{ij} \leq (\text{Max})C_j + u_j \quad (4)$$

and $$\Sigma C_{ij} = 1 \quad (5)$$

where $C_{ij}$ is the fraction of component j in the sample $_i$.

Min $C_j$ is the minimum amount of $_j$ in the initial calibration mixture i.e. standards in the bank or in the samples for which the method is to be used, and Max $C_j$ is the maximum amount of $_j$ in the initial calibration mixture i.e. standards in the bank or in the samples for which the method is to be used, and uj is usually between 1 and 0.01 or 1 and 0.05 preferably between 0.5 and 0.1 and can be fixed for each property or yield.

The constraints over the choice of such mixtures of N standards can also be equally fixed in the spectral area from which the samples will be drawn in order to remain in the areas of similar chemical nature.

The number of samples effectively drawn into the bank in this densification can be of several thousand generally 1000–2000. The calculation time is extended without significant deterioration in the results. If no further neighbours are found, the trawl of new samples drawn in is enlarged.

The spectrum of each mixture is calculated by the combination of the spectra of the standards used according to the formula $$S_{Mi} = \Sigma C_{ij} X S_j \quad (6)$$

where $S_j$ is the spectrum in the mixture of component $_j$ in the calibration matrix.

The properties or yields of each mixture PMi can be calculated by a generally linear combination of the properties or yields of the standards according to the formula $$P_{Mi} = \Sigma C_{ij} X P_j \quad (7)$$

where $P_j$ is the property or yields of component j

In the case of non linear additive properties, appropriate mixing factors can be applied e.g. by blending factors or similar for density and viscosity.

Having obtained the spectrum and the properties of the synthetic mixtures, these can be used as "standards" to help determine the properties of an unknown sample in the same way as a conventional standard, or to control the process by keeping the properties (or signal or function thereof) constant in the same way as a conventional standard.

Instead of using either of the two above approaches, 1–7, a third type Procedure 3 may be used as follows. The Q nearest samples to unknown X can be found from a selection from the bank samples for which the proximity index to the unknown samples is (V) X $i_{min}$) where v is $0.1 < v < 10$, (8) preferably $0.5 < v < 2$ or $1 \leq v \leq 5$. Then by the method of least squares is found a generally linear combination of the standard products, which are the Q nearest samples, to reproduce the spectrum of X according to the equation.

$$S_x \leq \Sigma C_R \times S_r \quad (9)$$

where $C_r$ is the coefficient for sample R in the total Q and $S_R$ is the spectrum of sample R. The coefficient $C_R$ which can be normalized to $C_R=1$ or not and/or optimized by the least squares route, allows an estimation of the property $P_x$ according to the equation $$P_x = \Sigma C_R \times P_R \qquad (10)$$

where $P_R$ is the property of sample R.

The eventual size of the estimation error can be derived by application of Gaussian theory, also called the propagation error (see Eq.10).

The above third approach can only be applied if the product X is situated inside the maximum extension of the standard products defined by equation (8) i.e. within the range of bank samples defined in equation (8). If this is not the case, X is outside the field of the actual bank of products and escapes from the area of knowledge of the method into the area of learning.

The densification process described in relation to equations 4–7, or 9 or 10 is usually applied to the method of the invention involving no correlation or regression techniques. However, if desired the densification process may be applied to increase the number of "standards" for consideration in an NIR analytical technique involving the correlation on regression techniques as described above e.g. MLR. The present invention also provides a method for adding an extra synthetic standard to a bank of known standards, each of which relates at least one absorption in the 600–2600 nm region (or a signal indicative thereof or of a mathematical function of said absorption eg a derivative thereof) of a known material to a known property related to that material, which method comprises choosing from the bank at least 2 standards for which equations 4 and 5 above are met, considering mixing the chosen standards in at least one proportion to produce at least one mixture for use as a synthetic standard, and estimating the spectrum and property/yield of said mixture according to equation 6 and 7 respectively.

The spectrum and property/yield of each "mixture" can then be added to the bank and used to develop models through the known correlation/regression approach, e.g. as described in the above mentioned patents.

As explained above if the nearest standard to the unknown is not one having the value $V_C$ for the property or yield, or having a value V for said property or yield within ±10%, e.g. ±5% or ±1% of said value $V_C$, or if the function $P_x-P_m$ is greater than the experimental error, especially more than 10%, 5% or 1% greater, then the process has deviated and needs adjustment, e.g. by changing one of the parameters of the process e.g. reaction conditions such as temperature, pressure, or amount/nature of catalyst for a reaction, or proportions or nature of the feeds in the case of a blending or reaction.

The method of the invention may be applied from the spectrum of a material to determine at least one physical, chemical, physicochemical and/or rheological property of that material or to control the process to keep substantially constant the value of at least one of said properties. The material may be a product of a chemical or physical or separation process, or which may be a feed to such a process, or the method can be used to determine at least one of said properties of a product of that process from the spectrum of at least one feed to that process, or to determine the yield of at least one product of that process. Each of the feed (or feeds) or products to the process may be a solid liquid or gas preferably at least one feed or product is a liquid.

Thus the method may be used for the physicochemical determination or prediction or process control in relation to at least one feed or product used in or obtained by an industrial process of the refining of oil and/or in petrochemical operations. The process may be a hydrocarbon conversion or separation process, preferably a reforming or catalytic cracking or hydrotreatment process or distillation or blending. In particular it may be used for determination of at least one property of a feed and/or the prediction and/or determination of at least one property and/or yield of product or control of said process to keep substantially constant said property or yield. It may be applied to a number of different processes such as processes for separating petroleum products such as atmospheric distillation vacuum distillation or separation by distillation, under pressure greater than atmospheric, as well as thermal or catalytic conversion, with or without partial or total hydrogenation, of a petroleum product, such as catalytic cracking e.g. fluid catalytic cracking (FCC), hydrocracking, reforming, isomerization, selective hydrogenation, viscoreduction or alkylation.

Of particular value is the use of the method in blending operations involving the prediction and/or determination of at least one property of a blend of liquid hydrocarbons or control of the value of said property. The blend may be optionally with other additives such as alkyl ethers), this method may include or not the determination for each constituent of the blend of a blend index for the property considered. In this method as applied to blending, the blend indices can be obtained simply by calculation and without the need for preparation of standard physical mixtures other than those contained in the databank. The blend indices can be combined linearly or non linearly within the fields of stability to determine from the value of this combination value for at least one property of the blend obtained. The blend may be made by mixing at least 2 of butane, hydrogenated steamcracked gasoline, isomerate, reformate, MTBE or TAME, FCC derived gasoline. This process may be repeated with numerical addition of other constituents separately to the liquid hydrocarbon base to determine a series of blending indices and then determination from these indices of the properties of the multi constituent lend (see e.g. Ex. 2 hereafter).

Examples of properties that can be determined and/or predicted or properties of materials in process controlled by the method of the invention include the following: for automobile fuels/gasolines, at least one of the Research Octane Number (RON), Motor Octane Number (MON) and/or their arithmetic mean, with or without lead additive and/or the methyl tert, butyl ether or methyl isoamyl ether and/or benzene content:

For automobile fuels/gasolines, at least one of the vapour pressure, density, volatility, distillation curve, e.g. percentage distilled at 70° C. and/or 100° C., oxygen content or benzene or sulphur content, chemical composition and/or gum content e.g. express in mg/100 ml, and/or susceptibility to lead (these properties are particularly determined for use in blending operations):

For diesel fuels or gas oils, at least one of the cetane number (e.g. motor measured), cetane index, cloud point, "discharge point", filterability, distillation curve, density e.g. at 15° C., flash point, viscosity e.g. at 40° C., chemical composition, sensitivity to additives and percentages of sulphur;

For distillation products from crude oil e.g. under atmospheric pressure at least one of the density, percentage of sulphur, viscosity at 100° C., distillation curve, paraffin content, residual carbon content or Conradson carbon content, naphtha content, flash point for petrol, cloud point for gas oil e.g. light gas oil and/or viscosity at 100° C. and/or sulphur content for atmospheric residues, and yield for at least one of the cuts, gasoline (bp 38–95° C.), benzine (bp 95–149° C.) naphtha bp 149–175° C., jet fuel bp 175–232° C., light gas oil bp 232–342° C., heavy gas oil bp 342–369° C., and atmospheric residue greater than 369° C.

For at least one of a feed or a product of a process of a catalytic cracking e.g. FCC process, at least one of the density, percentage of sulphur, aniline point, gas oil index, gasoline index, viscosity at 100° C., refractive index at 20° C., and/or 60° C., molecular weight, distillation temperature e.g. 50% distillation temperature, percentage of aromatic carbon, content of total nitrogen and factors characterizing the suitability of the feed for the cracking e.g. KUOP, crackability factor, cokability factor, and yield e.g. of gas, gasoline, gas oil or residue. Thus there may be determined the yields and/or properties of the different products obtained by distillation of the cracked products, such as RON and/or MON, clear or leaded for the gasoline cut and the viscosity at 100° C. for the distillation residue.

For at least one of a product or a feed of a catalytic reforming process, at least one of the density, distillation temperature and/or chemical composition (expressed as a percentage) of saturated linear hydrocarbon, isoparaffins, naphthenes, aromatics and olefins.

For at least one of a product or a feed of a process of hydrogenating gasoline at least one of the density, distillation temperature, RON and/or MON, clear or leaded vapour pressure, volatility, chemical composition (expressed as a percentage) of saturated linear hydrocarbons, isoparaffins, naphthenes, aromatics e.g. benzene, and mono/di substituted benzenes, olefins e.g. cyclic and non cyclic olefins, diolefins, the maleic anhydride index, and yield e.g. of at least one of the products obtained.

The method of the invention may also be used with chemical reactions in which at least one product is a hydrocarbon, and none of the feeds or products contains an element other than carbon or hydrogen. The hydrocarbon which may be gaseous or liquid at 25° C. Such reactions may involve as feed or product at least one olefin or actylene e.g. linear or branched, aliphatic or cycloaliphatic olefin with an internal or external ethylenic unsaturation, preferably of 2–20 carbons especially 2–8 carbons for alkenes or alkynes (such as ethylene, propylene, butene 1 or 2, isobutene, isopentene) or acetylene, and 5–8 carbons for cycloalkenes e.g. cyclohexene. The feed or product may also be an aromatic hydrocarbon e.g. benzene or naphthalene, optionally substituted by at least one (e.g. 1–3) alkyl or alkenyl group e.g. of 1–20 carbons, such as 1–6 carbons, especially methyl, ethyl or isopropyl; examples are benzene, toluene xylene, cumene and styrene. The feed or product may also be a non aromatic hydrocarbon, e.g. linear or branched aliphatic or cycloaliphatic with e.g. 1–20 or 5–8 carbons respectively, preferably 1–6 carbons and 6 or 7 carbons respectively, examples are methane, ethane, propane, n-butane, isobutane, and cyclohexane. The feed or product may also be a diene, conjugated or unconjugated, aliphatic or cycloaliphatic with e.g. 4–20 carbons or 6–20 carbons respectively; examples are butadiene and isoprene and cyclohexadiene. Examples of the reactions are hydrogenation (e.g. butadiene to butene-1 or 2 or cyclohexene to cyclohexane) dehydrogenation (e.g. ethane to ethylene or ethyl benzene to styrene), isomerisation (e.g. butene-1 or -2 to isobutene, or pentene-1 to isopentene) alkylation (e.g. benzene with ethylene to form ethylbenzene and/or styrene, or isobutene with butane to form iso octane), and cracking.

In addition to the use in petrochemical operations, the method is of wider application and may be applied in the pharmaceutical industry such as the production of pharmaceutically active compounds for use as medicines e.g. by fermentation, and in the perfumery industry for making perfumes and fragrances, especially in their blending and control thereof. The method may also be used in the food industry e.g. in brewing to control fermentation processes, in fermentation to make wine and quality control thereof, and control of food production e.g. sugar and water content in fruit juice and in control of maturing processes for fruits and vegetables. In each case the method may be applied to determine a property of the sample tested or product from that sample or keep substantially constant said property, which may be a fermentation or blended product preferably on line and especially with continuous feed back from the results to control the production process.

The known correlative techniques for modelling physicochemical properties based on NIR spectra have disadvantages, the chief of which is the need for establishing a strong correlation between the spectrum and the property, and their difficulty in dealing with positive or negative synergy between components contributing to that property. In the case of high density polyethylene one multi linear regression model in respect of density gives a coefficient of correlation that can on occasion be insufficiently high, so as to give problems in a polymerization process based on it.

The method of the invention can avoid the above problems with correlations, and regression calculations, and can be capable of being expanded automatically with use of a new product of different quality.

The present invention also provides a method of determining or predicting a value Px, of a property of a material X which is a feed to a process or a property of a product of a process from said material or yield of said process which method comprises measuring the absorption ($D_i$m) of said material at more than one wavelength in the region 600–2600 nm, comparing signals indicative of said absorptions or mathematical functions thereof with signals indicative of absorptions $D_i$m at the same wavelengths or mathematical functions thereof for a number of standards S in a bank for which the said property or yield P is known, and choosing from the bank at least one, and preferably at least 2 standard $S_m$ with properties or yield $P_m$ said standard Sm having the smallest average value of the absolute difference at each wavelength i between the signal for the material and the signal for the standard $S_m$ to obtain value $P_m$ with averaging of said properties or yield Pm, when more than 1 standard $S_m$ is chosen, and wherein said process is at least one of a polymerization, an oligomerization or an organic reaction in which at least one of the reactant and a product is a functionalized compound. The present invention also provides a control method in which the controlled process is at least one of said processes. The above method can be performed without regression or correlation techniques, e.g. between the absorption at any wavelength of the material and the property/yield.

The present invention also provides a method for adding an extra synthetic standard to a bank of known standards, each of which relates at least one absorption in the 600–2600 nm region (or a signal indicative thereof or of a mathematical function of said absorption eg a derivative thereof) of a known material to a known property related to that material, wherein said property is of said material, which is a feed to a process, or product of said process, or yield of said process, which method comprises choosing from the bank at least 2 standards for which equations 4 and 5 above are met, considering mixing the chosen standards in at least one proportion to produce at least one mixture for use as a synthetic standard, and estimating the spectrum and property of said mixture according to equation 6 and 7 respectively, said process being at least one of a polymerisations an oligomerization or an organic reaction in which at least one of the reactant and a product is a functionalized compound. The spectrum and property of each "mixture" can then be added to the bank and may be used to develop models through the known correlation/regression approach, eg based on that in the patents described above.

The method of the present invention is applicable to chemical reactions, which may be polymerisations or oligomerisations, or alternatively reactions in which at least one of a reactant and a product is a functionalised compound. In the chemical reactions each of the feeds and the products may be a solid, liquid or gas, preferably all the feeds are liquids and/or gases, and preferably all the products are liquids and/or solids, especially liquids.

Examples of polymerisations are condensation and addition polymerisation. Condensation polymerisations may produce thermoset polymers, such as phenolic novolac or resole resins curing with or without curing agents like hexamine, or polyurethanes, or thermoplastic polymers such as polyamides, e.g. polylactams such as Nylon-6 and polymers from polyamines and polycarboxylic acids e.g. poly hexamethylene adipate, and polyesters, such as those from diols e.g. aliphatic diols and organo di carboxylic acids e.g. aromatic or aryl bis (alkylene) dicarboxylic acids, such as poly ethylene terephthalate. Addition polymerisations tend to produce thermoplastic polymers, and may be thermal or free radical or catalysed reactions e.g. with Bronsted or proton acids or metals, especially transition metals. Examples of such polymerisations are those involving polymerisation at an olefinic double bond or ring opening of an epoxide or episulphide. The olefinic double bond is preferably a vinyl group $CH_2=C-$ and may be in a hydrocarbon e.g. an olefin especially an alkene such as one of 2–12 carbons especially ethylene alone or mixed with at least one alpha olefin of 3–12 carbons (especially in amount of 0.5–30% by weight based on total olefins) such as propylene, butene-1, 4-methyl-pentene-1, hexene-1, octene-1 or styrene; copolymers of such olefinic hydrocarbons, especially ethylene, with non hydrocarbon comonomers e.g. esters with olefinic groups such as vinyl esters e.g. vinyl acetate or alkyl(meth)acrylate or vinyl chloride may also be made. Addition polymerisation of iso olefins e.g. of 4–8 carbons such as isobutene alone or with other comonomers such as butadiene is included, as in addition polymerisation of olefinic non hydrocarbon monomers such as vinyl esters e.g. of 3–20 carbons especially 4–10 carbons such as vinyl acetate and propionate, and alkyl(meth)acrylates wherein the alkyl group has 1–20 carbons, especially 1–4 carbons for solid polymers e.g. polymethyl methacrylate, and 4–20 carbons for polymers for use as pour point depressants and VI improvers e.g. polydodecyl acrylate and methacrylate and copolymers with 2–10 monomers of different alkyl chain lengths. Vinyl chlorine homopolymers and copolymers e.g. with vinylidene chloride may also be made.

The method may also be used for ring opening reactions such as reactions of epoxides, episulphides or cyclic imines with organic compounds containing at least one active hydrogen such as compounds with at least one OH, NH or SH group, such as alcohols, phenols, primary or secondary amines or thiols. Alcohols e.g. of 1–30 carbons such as 2–6 carbons (e.g. butanol) especially alkanols or cycloalkanols are preferred. The epoxide is usually of 2–8 carbons e.g. ethylene oxide, propylene oxide, butylene oxide or cyclohexane oxide, while the episulphide and cyclic imines are preferably the corresponding analogues e.g. ethylene imine and ethylene sulphide.

In the case of polymerisation the method may be used to estimate the properties of the polymer or control the polymerisation to keep substantially constant said properties. The estimation or control may be made from the NIR spectrum of the feedstock (under constant conditions) or from the NIR spectrum of the product. Examples of properties are number and weight average molecular weights, and the molecular weight distribution, viscosity e.g. at 100° C., fluidity index, density, and chemical composition e.g. percentage of at least one monomer or comonomer in the polymer percentage of unsaturation e.g. ethylenic type, or side chain grouping, e.g. methyl, crystallinity, rigidity, flow parameters, draw strength at the flow threshold, free cracking resistance and shock resistance. In addition for polyisobutenes, the property may also be content of butene-1, and light and heavy polyisobutenes and unsaturation expressed in groups per liter and maleinisation index (or succinylation ratio) (sensitivity to Diels Alder reactions) as well as particular types of unsaturation e.g. vinylidene $CH_2=C-$ VIN, $tri(CH_3-C(CH_3)=CH<)TR11$, $tri2 (TR12)(CH_3-CH=C-)$ TRITOT $(R-CH=C<)$, TETRA $(>C=C<)$. For polyolefins e.g. polyethylene, other properties include percentage of comonomer, volatile compounds and degree of conversion. For polyalkylenoxylated compounds e.g. ethylene oxide condensates e.g. with alcohols, the method may be used to monitor the degree of conversion or the amount of alkylene oxide consumed, as well as the quality of the product e.g. content of groups derived from at least one epoxide or the distribution of those groups in the polymer chain, the product weight and number average molecular weight and its distribution, proportions of low and high molecular weight products (e.g. 150–600 or 600–15000 such as 5000–12000 respectively) Hydroxyl index (or mean number of hydroxyl groups per molecule), percentage of primary secondary and tertiary hydroxyl groups, allylic or propylenic type unsaturation, or impurity content.

The method is of especially value in the polymerisation of ethylene alone or with at least one alpha olefin as described above. The process is usually catalysed by at least one transition metal catalyst especially of Group IVA, VA or VIA, of the Periodic Table, such as titanium, zirconium, vanadium and/or chromium. The catalysts may be organometallic (including II complexes), especially with the above transition metals, and may be in the presence of at least one organo aluminium cocatalyst as in Zeigler Natta catalysts. Non organometallic catalysts such as chromium oxide may be used. The catalyst may be unsupported or supported e.g. on silica and/or alumina.

The method may also be applied to organic chemical processes, which are not polymerisations (including oligomerisations); thus processes involving only monomeric starting materials and products are suitable. In particular these include processes in which at least one of a reactant and a product is a functionalised compound i.e. is not a hydrocarbon but contains at least one functional group, e.g. with at least one atom other than carbon and hydrogen, in particular at least one oxygen, nitrogen, sulphur, phosphorus, or halogen e.g. chlorine, bromine, iodine or fluorine atom, especially 1–3 such atoms in the compound. The functional group may be an alcohol, phenol, thiol, primary secondary or tertiary amine, aldehyde, ketone, ester, acid amide, nitrile or ether or sulphide, or aromatic or aliphatic halide.

In particular the process may be a hydration such as an olefin to an alcohol (e.g. ethylene or propylene to ethanol or isopropanol respectively) dehydration such as an alcohol to an olefin (e.g. tert butanol to isobutene) etherification such as reaction of an alcohol or phenol with an olefin (e.g. tert butanol with isobutene to form Methyl tert butyl ether) or reaction of an olefin with water (e.g. ethylene to diethyl ether), esterification such as reaction of a carboxylic acid (or derivative thereof e.g. acid chloride) with an alcohol e.g. alkanol of 1–20 carbons) or with an olefin (e.g. ethylene, propylene or n or isobutene), such as reaction of acetic acid with ethylene to form ethyl acetate or with dehydrogenation) vinyl acetate. The process may also be an oxidation e.g. an alcohol or aldehyde to an acid such as methanol to formic acid, or a hydrocarbon to an alcohol or ketone or an acid e.g. naphtha to acetic acid or methane to formic acid or cumene to acetone and phenol, an ammoxidation e.g. an aliphatic substituted olefin (with optionally 3–6 carbons) to a nitrile such as propylene to acrylonitrile, or a carbonylation of an olefin or an alcohol to form a carboxylic acid and/or anhydride, such as the reaction of methanol with carbon monoxide to form acetic acid and/or anhydride.

In a further embodiment the present invention provides a method of determining or predicting a value Px, of a property of a material or a property of a product of a process from said material or yield of said process which method comprises measuring the absorption $(D_ix)$ of said material at more than one wavelength in the region 600–2600 nm, comparing signals indicative of said absorptions or mathematical functions thereof with signals indicative of absorptions $D_im$ at the same wavelengths or mathematical functions thereof for a number of standards S in a bank for which the said property or yield P is known, and choosing from the bank at least one, preferably at least 2 standard $S_m$ with property $P_m$ having the smallest average value of the absolute difference at each wavelength i between the signal for the material and the signal for the standard $S_m$ to obtain $P_m$ with averaging of said properties or yields Pm when more than 1 standard $S_m$ is chosen and wherein said material X is a composition comprising part of a lubricating oil fraction obtainable from a distillation of oil e.g. a vacuum distillation of oil. The control process of the invention may also be applied with the material X is a composition comprising part of a lubricating oil fraction obtainable from a distillation of oil e.g. a vacuum distillation of oil.

The above method can be performed without regression or correlation techniques, e.g. between the absorption at any wavelength of the material and the property/yield.

The densification process described in relation to equations 4–7, or 9 or 10 is usually applied to the method of the invention involving no correlation or regression techniques. However, if desired the densification process may be applied to increase the number of "standards" for consideration in any NIR analytical technique involving the correlation on regression techniques as described above e.g. MLR. The present invention also provides a method for adding an extra synthetic standard to a bank of known standards, each of which relates at least one absorption in the 600–2600 nm region (or a signal indicative thereof or of a mathematical function of said absorption eg a derivative thereof) of a known material to a known property related to that material, wherein said property is of said material or is of a product or yield of a process from said material, which method comprises choosing from the bank at least 2 standards for which equations 4 and 5 above are met, considering mixing the chosen standards in at least one proportion to produce at least one mixture for use as a synthetic standard, and estimating the spectrum and property of said mixture according to equation 6 and 7 respectively and wherein said material X is a composition comprising part of a lubricating oil fraction obtainable from a vacuum distillation of oil e.g. a vacuum distillation of oil.

The spectrum and property of each "mixture" can then be added to the bank and may be used to develop the models through known correlation/regression approach, e.g. as described in the above mentioned patents.

This embodiment of the method of the present invention is applicable to various petroleum hydrocarbon fractions, which comprise part (and only part) of a lubricating oil fraction e.g. from a vacuum distillation of oil after removal of materials boiling above 370° C. (under atmospheric pressure). Such fractions include the partly purified lube cut from the distillation, e.g. after at least one of the steps of dewaxing and dearomatizing and preferably both, (as in lube base oil) and the partly purified vacuum distillation residue e.g. after at least one of the steps of deasphalting, dewaxing and dearomatizing, and preferably all 3 (as in bright stock). Such fractions also include the aromatic extract of the lube oil cut or distillation residue, or a wax separated therefrom.

The method is preferably applied to lube base oils or bright stock and their properties or control of their production. The base oil may be a 100–600 neutral or solvent or BS oil e.g. 100, 150, 200, 300, 400 or 500 neutral oil or BS solvent. It may have at leas tone of and preferably all of the following properties a density at 15° C. of 0.80–0.95 kg/l e.g. 0.85–0/92 kg/l, a kinematic viscosity at 40° C. of 10–1000cSt e.g. 15–700cSt, and at 100° C. of 0.5–50cSt e.g. 1–40cSt, a Flash Point of 180° C. min e.g. 190° C. min, a pour point of 0° C. maximum e.g. –5° C. or –7° C. maximum and a Viscosity Index of 80 min e.g. 90 min. The base oil may be present alone, or may be mixed with the aromatic extract as in process oils, which may have at least one of, and preferably all of the following properties, a density at 15° C. of 0.95–1.10 kg/l, e.g. 0.97–1.06 kg/l, a Kinematic Viscosity at 40° C. of at least 30cSt e.g. at least 37cSt, and at 100° C. of at most 50cSt e.g. at most 45cSt and a Flash Point of at least 185° C. e.g. 190° C. min. The base oil may also be present mixed with at least one wax e.g. in amount of, 0–50% such as 1–40% or 15–35% by weight as in "slack wax", the mixture of oil and solid wax separated in the dewaxing step, or waxes as in the residue from the dearomatization step.

The base oil may also be mixed with at least one non hydrocarbon additive to boost its effectiveness for lubricant use. Types of additives which may each be present in amounts of 0.01–10% by weight (based on the weight of base oil) e.g. 0.1–1% are (i) detergents/dispersants such as alkyl phenates and/or alkyl aryl sulphates (ii) antioxidants such as phenol derivatives, (iii) viscosity index improvers and pour point depressants, such as alkyl poly(methyl) acrylate homo and especially copolymers, styrene butadiene polymers and polyisobutylene (iv) anti corrosives, such as sulphur compounds, zinc sulphophosphates and dithiophosphates, and (v) solid or liquid lubricity additives, such as graphite, molybdenum disulphide and silicones.

The method may also be applied to the aromatic extract resulting from the extraction of aromatics (e.g. with furfural) from the lube cut of the vacuum distillate or the deasphalted vacuum residue. This aromatic extract is different from the base oil as it contains a much higher amount of aromatics, such as benzene, toluene and xylenes, and higher molecular weight aromatics e.g. of at least 30 carbons than the base oil. The aromatic extract may be used alone or mixed with an amount of base oil to form process oil.

The method may also be applied to solid or liquid paraffins or waxes e.g. as separated in a dewaxing step from the lube cut or the deasphalted residue. The wax may be mixed with base oil as in slack wax, or substantially free of base oil and may then if desired be further purified to produce a paraffin. Waxes may be used industrially while paraffins may be used for food and cosmetic uses.

The method is preferably applied for process control in a part of a refinery producing lubricants and by products therefrom, but may also be used for identification of unknowns e.g. for "finger printing" oils such as formulated oils.

Examples of properties that can be determined/estimated for the various materials or whose values can be kept substantially constant in the control processes are as follows. Where the material is a base oil (or formulated oil) the property may be at least one of the density, sulphur content, Flash Point, Flow Point, kinematic viscosity at 40° C. and at 100° C., Viscosity Index, aromatic carbon content, Polycyclic Aromatic hydrocarbon content, nitrogen base content, and inflammability according to Pensky Martens °C. When the material is a crude paraffin or slack wax, the property may be at least one of the density, viscosity e.g. at 40° C. or 100° C. and oil content. When the material is a process oil, the property may be at least one f the density, sulphur content, Polycyclic Aromatic hydrocarbon content, viscosity e.g. at 40° C. or 100° C. and the Flash Point e.g. Cleveland Flash Point.

In each case the method may be applied to determine a property of the feed tested or yield from that feed preferably on line and especially with continuous feed back from the results to control the production process. Alternatively the method may be applied to determine the nearest standards of property or yield and then the process controlled e.g. on line and especially with feedback fro the results to control the production process.

In each of the above processes the property or yield of a product determined or predicted by the method of the invention can be compared to the desired figure and notice taken of any deviations by adjusting the parameters of the process e.g. flow rates proportion or nature of feed(s) (e.g. via operation of control valves) and/or temperature/pressure etc to bring the property or yield back to the desired figure. In each of the above processes the control may be performed based on deviations from the signals (or functions) for the standard or from the property(ies) of that standard. These controls of the process, which may be a blending, separation or chemical e.g. polymerisation process, are usually performed wit a micro computer which is linked to the spectrometer and also performs the search for the standards Sm. The inline control of the process is very efficient and very fast.

The present invention also provides an apparatus suitable for carrying out the method of the invention comprising an infra red spectrometer and a computer wherein the infra red spectrometer is linked to the computer programmed in such manner that the property or yield may be determined continuously and in real time or to determine the nearest standard and this in turn is linked to a control means to adjust the process to any deviations when $S_{mc}$ is not the nearest standard. The spectrometer is suitable for measuring spectra in at least partly in the 600–2600 nm wavelength range and can be linked to a signal processing device to allow numerical treatment of the spectrum, preferably by Fourier Transformation. The spectrometer receives at least one signal from a vessel containing product or from a feed or product line. The spectrometer is suitable for measuring spectra in at least partly in the 600–2600 nm wavelength range and can be linked to a signal processing device to allow numerical treatment of the spectrum, preferably by Fourier Transformation. The spectrometer receives at least one signal from a vessel containing product or from a feed or product line. The information obtained can be used as an information vector for the computer which is programmed to determine the property or yield or nearest standard e.g. via calculations on the proximity indices in relation to standards. Conveniently in relation to a process, the computer may be used in a closed loop feed back or feed forward control system for controlling processing equipment e.g. changing the process parameters in response to variations in the property and/or yield of product from the desired value or nearest standard from measurement of more than one absorptions in the NIR spectrum of the product and/or feed.

The present invention also provides a computer programmed to perform the method of the invention of determining or predicting the value $P_x$ of the property or yield, controlling the process or programmed to perform the method of the invention of adding an extra synthetic standard to the bank of known standards. The apparatus for use with the former method of the invention comprises an NIR spectrometer receiving at least one signal from a feed or product line in said process and being coupled to a computer to effect continuous measurement of the spectra of the feed and/or product and provide feed back or feed forward control of the process. The present invention also provides a computer implemented method for a system including a spectrometer linked to a process line containing a material X, a computer linked to the spectrometer, and a controller linked to the computer and the process line, the computer including databanks having stored therein signals indicative of absorptions of standard materials (or mathematical functions thereof) and corresponding properties of said materials or products of said process for which X is a feed, or yield of said process, the method comprises steps of:

measuring absorption at more than one wavelength in the region 600–2600 nm at the process line and producing absorption signals (or mathematical functions eg derivatives thereof) by the spectrometer in accordance therewith;

accessing the databanks of the computer in accordance with the absorption signals (or functions thereof);

comparing, by the computer, the absorption signals (or functions thereof) to the signals (or functions thereof) of the standard materials stored in the databanks;

choosing at least one standard based on the comparing, said standard having the smallest average value of the absolute difference at each wavelength i between the signal for the absorption (or function thereof) for the material and the signal (or function thereof) for the standards, optionally with averaging of said properties or yields when more than one standard is chosen) and controlling said process in accordance with the outputted property/yield, or in accordance with the outputted standard to ensure that standard $S_{mc}$ is the one with the smallest average value.

The benefits of invention allow improvements in modelling or control of processes involving modelling with the following areas, identification and classification of novel products, simultaneous estimation of all of P properties on a sample without the need for generating P different models, or simultaneous control of all the properties and with the option of automatic upgrading of the model, the method being self learning or adjusting. The method of the invention overcomes the difficulties with the classical regressional approach, in particular avoiding all difficulties with numerical stability of the models, allowing easy and rapid identification and classification of a sample of a product analyzed by spectral recognition and then instant conclusions as to whether the sample is known or unknown, allowing simultaneous determination of many properties. In the case of blends the method can be used to determine whether the property of the blend is simply additive or synergetic in relation to a blend components; the latter is particularly useful for different blend indices and the indices considered.

The method also allows an extension of the field of application of the method without the need to rewrite the model, apart from the need to integrate the new samples which are inside or outside the previous field of validity of the method. This possibility of automatic learning, which is not possessed by traditional regression techniques, is a decisive advantage in the framework of continuous inline industrial control processes, because it allows the return of the industrial plant operations to the model in a certain and rapid manner in a minimum time and with all the properties considered in the model. In contrast classical regression methods would necessitate the redevelopment of all the models, which is long and laborious without being able to guarantee the result of the new model obtained, because a new validation period is necessary, in addition during the redevelopment of the model any commercial use e.g. in a refinery of the model is very limited. Furthermore, the method of invention allows equally the easy extension to a number of properties, which are simply incorporated into the known bank.

This remarkable possibility is true not only for control of processes with conventional properties or with determination of those conventional properties such as physical chemical and/or rheological properties, but also for complex ones (such as octane number). Also it is possible to quantify by the process the response or susceptibility to lead of automobile fuels as well as the response to additives such as nitrates, of fuels used in diesel engines. The methods of the invention equally allow application of the models from one apparatus to another and from one spectral region to another, where conventional regressive method cannot give satisfactory solutions. This apparatus portability is made possible by the fact that the differences between different spectra are the same in one apparatus as another, for the same type of spectrometer being considered (e.g. network scatter, Fourier transform, accousto optical system AOTS, diode array etc). This portability between spectral regions depends on the fact that as the spectral regions are intercorrelated, the relations between the spectra are maintained between one another.

The invention is illustrated in the following Examples in which the Minimal Index is calculated according to the Minimal Index Procedure described above. Mathematically the steps concerned are as follows.

For each couple of standard samples i, j, the Proximity Index $i_{ij}$ is determined from the NIR spectra by use of equation 1, 2 or 3 and the properties are measured. For each Proximity Index is calculated the absolute difference $EP_{ij}$ between the properties of the samples. The Minimal Index for property P is obtained from the average $(EM_pL)$ of $EP_{ij}$ for different values of L when $L \geq ij$. Thus the $EM_p(L)=1/K \Sigma_i \Sigma_j EP_{ij}$ for each of K samples for which $i_{ij} \leq L$.

$EMp(L)+t\sigma(M)$ is plotted against the proximity index and in addition there is plotted the reproducibility of the standard method at a given level of confidence (usually 95%), as defined in the Minimal Index Procedure above. The intercept of the curve from EMpL and the reproducibility give the upper limit i.e. the Minimal Index.

For the Examples the data is expressed in Tables in a form as shown below in For each Proximity Index is calculated the absolute difference $EP_{ij}$ between the which the data is as follows.

| | | Absorption | | | |
|---|---|---|---|---|---|
| | Weighting | Un-known | Esti-mated | Standard A | Standard B |
| Proximity Index Wavelength λ | | | | | |
| $cm^{-1}$  nm | | | | | |
| Property 1 | | | | | |
| Property j | | | | | |
| Property m | | | | | |

The wavelengths chosen are shown in columns 1 and 2.

Column 3 gives the weight loading associated with each wavelength for the proximity index for the standards; 1 denotes no loading.

Column 4 shows for the unknown sample the absorption at the various wavelengths and at the bottom the properties of that sample determined by standard methods.

Column 5 shows for the unknown sample the estimated values of the properties and the absorptions using the method of the invention based on the properties and absorptions of the chosen standards.

Columns 6, 7 etc show the values of the absorptions and properties for the standards chosen from the bank. Line 2 gives the value of the proximity index between the unknown sample and each of the chosen standards.

EXAMPLE 1

Determination of Octane Number and other Properties of a Motor Fuel

The NIR spectra between 4800 and 4000 $cm^{-1}$ of a superfuel ID and a number of standard superfuels of known properties were measured. The base line was taken at 4780 $cm^{-1}$ though similar results would be obtained with baseline drawn between 2 or more points. The absorbances were normalized.

By the Minimal Index Procedure described above, with use of equation 2 and non weighting of the absorbences the Minimal Index (MI) was calculated to be $1 \times 10^{-4}$. Following reference to the bank of data on superfuels and use of Procedure 1, 3 standard samples were found with a proximity index with respect to the superfuel of less than M1. The properties of these standards are shown in Table 1. From the properties of the standard samples, octane numbers (RON and MON), vapour pressure (hpa) volatility, percentage distilled at 70° C. and at 100° C., gum content (in mg/ml), and content of sulphur, benzene (vol %) and MTBE were calculated for the superfuel by taking the arithmetic mean of the values for the 3 chosen standards. The estimated results are compared with the measured results.

All the properties were obtained from the single NIR measurement on the unknown superfuel and without any regression calculations, and with an accuracy in agreement with the reproducibilities of the reference methods. Other properties can be determined in a similar way.

EXAMPLE 2

(a) Production of an Unleaded Mixed Fuel from 6 Components

A target SUPER98 superfuel of the properties given in column 3 of Table 2a1, was to be obtained by mixing the remains of a tank of finished gasoline with 5 components, butane, hydrogenated steamcracked gasoline HEN, isomerate ISOM, reformate (REF) and MTBE. NIR absorptions at 4800–4000 cm$^{-1}$ measured with a Fourier Transform spectrometer were measured, with a base line taken at 4780 cm$^{-1}$ and absorbances normalized. Results are in Table 2a1.

Mathematic calculations were done with a computer to mix the spectra and properties of the 6 components to reproduce a finished product.

5% MTBE (on target fuel) (i.e. 4.76% in the final mixture) was "added" mathematically to a spectrum of the target fuel to give a mixture whose NIR spectrum was noted. The Minimal Index was 1×10$^{-4}$ determined as described above from the finished gasoline. 3 standards 2A, 2B and 2C were found with proximity indices with respect to the mixture, without weighting, and hence by averaging the properties of the standards the properties of the mixture were obtained. Table 2a.2 shows the spectrum of the mixture, the 3 standards and the estimation for the mixture as well as the properties of the standards and the estimated figures). The process was repeated with addition of each of the other 4 components to the spectrum of gasoline target.

On the basis of the figures obtained, the blending index for each property was found according to the linear formula $$IP(mix)=[(1+\alpha)\times P(mix)-P(ref)]/\alpha$$

where

IP (mix) is the blending index for the ingredient in the mixture in relation to property P α is the percentage of ingredient in the mixture P (mix) is the property of the mixture (ingredient+ gasoline) added) estimated by the process.

P (ref) is the property of the reference target gasoline.

The blending index for addition of MTBE is shown in Table 2a3.

In order to obey the linearity law here, it is necessary to limit the additions to not more than a quarter of the minimum to maximum range of the constituent studied in the industrial mixtures. However for concentration less than 20% such as for these oxygenated compounds, addition of 5% is acceptable.

The process with MTBE added to the gasoline was repeated with the other 4 components (and on the basis of linearity in the blending as with MTBE) to obtain blending indices for them as well (see Table 2a3). Then with the blending indices for each property for each ingredient, one can calculate the relative volume fractions needed to give the desired properties for the Superfuel 98 and hence the blending order. The 6 components were then mixed in the desired proportions and then properties of the mixture tested and compared to those estimated by the method of the invention from the components present (see Results in Table 2a4). In the estimation of the products and the comparison with the bank of standards, the Minimum Index was 1×10$^{-4}$. 3 standards 2D, 2E, 2F were found with suitable proximity indices from which the properties of the superfuel were estimated by averaging as described in Procedure 1. There was good agreement between the properties obtained via the blending order, those measured on the fuel made and those estimated by the method of the invention. The differences are very small and in the area of reproducibility of the standard methods.

EXAMPLE 2b

Production of a 5 component leaded Superfuel mixture

A target superfuel of the SUPER 97 type with 0.15 g/l of lead tetraethyl and having as specification an RON of 97, had an NIR spectrum as in Col 3 of Table 2b1 below and other properties as given in col 3 of Table 2b1 below. There were available 4 components (HEN, ISOM, REF and an FCC cat cracker gasoline) and the remains of a tank of finished refined gasoline for making the target fuel. The NIR spectra of these 5 components were measured as in Ex. 2. The results are in Table 2b1.

As in Ex. 2a, mathematical calculations were done with a computer to obtain the spectra and properties of 5 components to reproduce a finished product. Proximity indices with respect to standard samples were calculated based on normalized absorbencies which were not weighted. The method of the invention was used to find appropriate standards, using the procedure of artificial mixtures as described in Procedure 3 and equation 8 above in which v was 1 and with a Min. Index of 2×10$^{-4}$, the latter having been calculated for standard fuel mixtures as described above.

Table 2b2 describes the results of addition of 5% of the FCC gasoline to a reference Super 97 gasoline target as well as the 3 standards 2G, 2H, 2J found by the method of this invention, from which the estimated properties were found. The same procedure was performed with the other components.

The blending indices were found in the same way as for Ex. 2a, with the results for FCC gasoline in Table 2b3 and for the other components in the same way. The spectral blending index (for the linear area) is obtained for each property as shown in Table 2b3. A blending order was also calculated, as in Ex. 2a, the results being in Table 2b3.

The process of Ex 2a was repeated but with the above components and a Minimal Index of 2×10$^{-4}$. The results are in Table 2b4. 3 standards 2K, 2L, 2M were found with appropriate proximity indices, which allowed the properties of the product to be estimated by averaging. Again good agreements is seen between the properties estimated from the blending order and those measured on the product made, and also between the same properties measured and those measured by the process. The differences seen are very small and in the area of reproducibility of the standard methods. Other properties can be obtained in a similar way.

EXAMPLE 3

Determination of cetane index and other properties of a gas oil

The properties of an unknown gas oil 3A were desired. The method of this invention was applied with respect to a bank of known standard gas oils with known NIR spectra. The NIR spectra were obtained by F T spectrometer in the 4800–4000 cm$^{-1}$ region [with 4780 cm$^{-1}$ baseline and were normalized] The proximity indices were calculated on the basis of Equation 2, and the Minimal Index was 2.5×10$^{-6}$ (estimated from standard gas oil data as described above). The bank of standards was sufficiently dense for there to be found 2 standards 3B and 3C inside the sphere with proximity index less than 2.5×10$^{-6}$. Table 3.1 gives the details of the spectra and properties of the unknown oil A, and the standards and the estimated spectrum and properties, obtained by averaging. All the properties were obtained with an accuracy in agreement with the limits of reproducibility of the reference methods. Other properties can be obtained in a similar way.

EXAMPLE 4

On line prediction, based on NIR spectra on a mixture of crude oils fed to an atmosphere distillation unit, of yields and properties of the different distillation cuts such as gasoline (38–95° C.) benzine (95–149° C.) naphtha (149–175° C., jet fuel (175–232° C.) light gas oil (232–242° C.) heavy gas oil (342–369° C.) and atmospheric residue (bp). 369° C.).

An atmospheric distillation unit in a refinery was fed with a charge 4C which was a mixture in wt % of the following crudes, RUMASHKINO 81%, Iranian Heavy 18%, Iranian light 1%.

Yields of various distillation cuts were desired, the boiling ranges being given above, as well as key properties of each cut as described in Table 4.1, NIR spectra were measured as in Ex 1 on the crude oil. Min. Index was determined from NIR spectra on standard crude oil (as described above) and was $2.6 \times 10^{-6}$. The method of the invention was applied using Procedure 3 and equation 8, in which v was 1, to the bank which was sufficiently dense for 2 standards 4A and 4B to be found with small enough proximity indices. These standards contained (wt %) (for 4A) Romashkino 52% Iranian Heavy 29%. Arabian Heavy 11%, Kuwait 4%, Arabian light 2% and Iranian light 2%) and (for 4B) Iranian Heavy 78%, Romashkino 21% and Arabian Heavy 1%. The data in Table 4.1 shows the observed properties as well as the yields of the cuts and their properties. The results obtained by this procedure were extremely satisfactory, the differences observed being in accordance with standard methods of measurement. Other properties can be obtained in a similar way.

The yields and properties of the distillation cuts remarkably were obtained directly on the basis of the NIR spectra of the feed and in line without regressional type calculations.

EXAMPLE 5
Determination in line of the properties of a mixture of crude oils Other properties of the charge mixture of crude oils of Ex 4 were sought, based on the NIR spectra determined as in Ex 4. The method of the invention was applied as in Ex 1 with the Minimal Index in all cases being $2.6 \times 10^{-6}$. Two standard crude oils 4A and 4B were found in the bank by using Equation 2. The results are shown in Table 5.1. Other properties can be obtained in a similar way.

Here too the method demonstrates its capacity to predict all types of properties without any regression type of calculation requiring fastidious calculations. The results generally, as in the other Example, were in accordance with the results obtained by the reference methods, the deviations being found in the limits of reproducibility of the same methods.

EXAMPLE 6
Determination of the Properties of a feed to a reformer

A feed 6D to a reformer unit was analysed by the method of the invention as described in Example 1 with the NIR spectra recorded at 2000–2500 nm, the absorbancies normalised and not weighted. The NIR spectrum was compared by the method of Procedure 3 and equation 8 (wherein v is 1) with a Minimum Indexof $2 \times 10^{-4}$, which had been previously calculated as described abvoe from NIR spectra on standard reformer feeds. Three standards 6A, 6B and 6C from the reference feed bank were found with small enough proximity indices; details of the spectra of the feed and the standards are given in Table 6.1, together with 5 properties estimated for the feed by averaging the corresponding values of those standards. The actual properties of the feed were measured for comparison; the measurements were by traditional methods (gas chromatography and density), the former necessitating laboratory determination for several hours, compared to the present NIR process which gave the same results in a few minutes and on line (real time in the unit) and with better reproducibility.

The process allows the obtaining of a result with remarkable economy while avoiding having to produce 5 regressive models. The differences between the 5 properties as estimated and as measured experimentally are in agreement with the reproducibility of the known reference methods, name 1.5% for gas chromatography form chemical compositions and 2% o for density. The method can be equally applied for other properties such as ASTM distillation temperature curve for the feed.

EXAMPLE 7
Determination of the properties of a feed to an FCC unit, as well as the yield and properties of the products obtained The NIR spectrum of the above feed 7D was measured at 4800–4000 $cm^{-1}$, with base line at 4780 $cm^{-1}$, normalisation of the spectrum and no weighting. The procedure 3 was used with equation 8, with v=1, and the Min. Index of $2.5 \times 10^{-6}$ the latter having been previously calculated as described above from NIR spectra on standard FCC feeds of known properties.

The properties of the feed charge 7D sought were listed in Table 7.1 and included factors characterising the charge to the FCC unit, such as KUOP, crackability and cokability. The KUOP or Watson factor is defined as i $KUOP = \sqrt[3]{V\theta}/density60/60$ where θ is boiling point on a Rankin scale (Absolute Fahrenheit scale) and density 60/60 is the density of the feed at 60° F. compared to that of water at 60° F.

The cracking unit operated under the following conditions: riser inlet temperature 250° C., riser outlet temperature 525° C., MHSV (Mass Hourly Space Velocity) 78 kg/h per kg, C/O ratio 6.6, activity of catalyst 65 (in Microactivity Test).

The cracking gave a gasoline cut defined by ASTM distillation with initial point of 38° C. and 90% distilled at 190° C. and a residue defined by ASTM distillation with 10% distilling at 385° C.

By application of Procedure 3 to the bank of samples of FCC feeds 2 standards were found namely 7A, 7B and the properties and yields estimated as shown in Table 7.1. The results were all in line with the accuracy based on the reference methods, as well as in line with the properties and yields actually meansured. Other properties of the charge or products can be estimated in a similar way.

EXAMPLE 8
On line determination of properties of the feed to a gasoline Hydrogenation unit.

The gasolines obtained from steam cracking units have the inconvenience of containing non negligible amounts of unsaturated dienic compounds, which have the effect of inducing and encouraging formation of gums which are undesirable in motor fuel. These gasolines are therefore selectively hydrogenated to eliminated the dienes without at the same time hydrogenating other unsaturated compounds present in the gasoline such as monoolefins and aromatics. The control over these dienes is therefore essential not only for the final quality of the fuel (principly RON and MON) but also for the hydrogen consumption of the hydrogenation unit.

Units for Hydrogenating gasolines from steamcrackers are generally coupled to a downstream distillation unit to separate a gasoline from a light cut (95% distillation by about 75° C.) and one from a heavy cut (initial point about 95° C.), before extraction of the benzene in the core cut and recycle of the extraction residue from that cut called raffinate.

It was desired to determine by the process of the invention the properties of the gasoline from the steam cracker, which was a feed to a gasoline hydrogenation unit. NIR spectra were obtained on the feed on line at 1000–1600 nm using a scatter dispersion spectrometer. The absorbences were normallised, but the data was not weighted for use in Equation 8, in which v was 1 and $^i$min was $2.5 \times 10^{-5}$ (the latter having been determined from NIR spectra on similar feeds of known properties). 5 standards 8A–8E were found in the search using Procedure 3, and the properties of the feed calculated therefrom by averaging were all in agreement with the measured properties of the feed. The results were shown in Table 8.1.

In addition the chemical composition of the feed was obtained with great particularity allowing a distinction to be made for example between cyclic and non cyclic olefins as well as benzene and mono and di substituted aromatics. Equally by the process potential yields were obtained of the distillation cuts after the selective hydrogenation of the gasoline. All the properties were obtained with great accuracy within the limits of the experimental reproducibility for that kind of property.

Other properties can be determined such as Octane Indices for the different cuts or temperatures of ASTM distillation curves for the gasoline.

EXAMPLE 9

Method for use when the density of standards in the bank is sufficient

The MON level for a reformate 9A was sought. The NIR spectrum was measured at 4800–4000 cm$^{-1}$ with a base line at 4780 cm$^{-1}$, the spectra were normalised. With reference to NIR spectra on reformates of known properties the Minimal Index was found by calculation as described above to be $2 \times 10^{-5}$. The proximity indices of reformate 9A and known standards were determined by Procedure 1. The results were as given in Table 9.1. 5 standards 9B–F were found from the reformate bank with proximity indices low in relation to the reformate 9A, but insufficiently low to be less than Minimal Index, as the density of the bank was too small. It was thus not possible to calculate the properties with the accuracy desired. Procedure 1 using Equation 1 was replaced by Procedure 2 using Equations 4–7, with in Equation 4 values of Cj between $-0.3$ and $+1.3$, in order to increase the density of "standards" in the bank by providing new synthetic mixtures.

Tables 9.2 and 9.3 show the results obtained, showing in Column 3 the absorbancies and properties for the "standards" (MC1, MC2) obtained by this densification, and with small enough proximity indices. Col. 4 and subsequent columns give the absorbances properties of the standards 9B, 9D and 9G in the reformate bank used to generate the new "standards". Line 2 in these Tables show for each standard the fraction retained in the mixture to generate the new "standards". This fraction can be negative, but comprises between $-0.3$ (or $-0.4$) and $+1.3$ (in Eq. 4).

Using the data on MC1 and MC2 as "standards", the properties of the reformate 9A were calculated by averaging (as shown in Table 9.4). The calculated MON of reformate 9A accords well with the experimentally measured figure, and is inside the limits of reproducibility of the standard method. The process can be used in a similar way for other properties.

The method of the invention equally allows immediate automatic upgrading of the bank by automatic integration of the new samples. The process with the proximity indices allows consideration as a standard of all the novel "standards" introduced into the bank. This property is remarkable because it allows very rapid determination of properties in the case of novel products not recognised in the bank and then the gaining of precious time in the adjustment of operating conditions for the manufacturing unit.

Table 9.5 shows that a novel "sample" measured immediately after incorporation of the above unrecognised sample 9A in the databank, now used as a standard, is recognised and is perfectly calculated for the totality of its properties and without any modification nor intervention on the used models. It is important to note the superiority of the procedure over classical regressional models. The latter are incapable of predicting properties of samples not included within their application range or predict them with a non acceptable error, and therefore would need to be reactivated by the necessity to remake the model (one for each property) and this without guarantee of success, and with the commercial plant functioning blind during the recalibration period.

TABLE 1.1

Determination of Octane Indices and other Properties in an automobile fuel

|  |  | Weighting | 1D Measured | 1D Estimated | 1A | 1B | 1C |
|---|---|---|---|---|---|---|---|
| Proximity Index |  |  |  | 0.000027526 | 0.000067452 | 0.000072577 | 0.000096807 |
| Wavelength |  |  |  |  |  |  |  |
| λ (cm-1) | λ (nm) |  |  |  |  |  |  |
| 4720 | 2119 | 1 | 0.0021031 | 0.0021115 | 0.0021985 | 0.0020678 | 0.0020683 |
| 4670 | 2141 | 1 | 0.01696 | 0.016887 | 0.017029 | 0.016831 | 0.016801 |
| 4640 | 2155 | 1 | 0.016172 | 0.016464 | 0.017171 | 0.015695 | 0.016527 |
| 4615 | 2167 | 1 | 0.023426 | 0.022955 | 0.022671 | 0.022765 | 0.023429 |
| 4585 | 2181 | 1 | 0.014407 | 0.014379 | 0.014241 | 0.014863 | 0.014034 |
| 4485 | 2230 | 1 | 0.011377 | 0.011472 | 0.011516 | 0.011788 | 0.011112 |
| 4460 | 2242 | 1 | 0.015794 | 0.015825 | 0.015718 | 0.015331 | 0.016428 |
| 4385 | 2281 | 1 | 0.092392 | 0.090762 | 0.09071 | 0.092874 | 0.088701 |
| 4332 | 2308 | 1 | 0.127 | 0.12402 | 0.12292 | 0.1241 | 0.12505 |
| 4305 | 2323 | 1 | 0.10482 | 0.10678 | 0.1021 | 0.10946 | 0.10879 |
| 4260 | 2347 | 1 | 0.10001 | 0.099412 | 0.098621 | 0.095524 | 0.10409 |
| 4210 | 2375 | 1 | 0.065489 | 0.06726 | 0.067463 | 0.066664 | 0.067653 |
| 4170 | 2398 | 1 | 0.063954 | 0.06449 | 0.066434 | 0.064491 | 0.062546 |

TABLE 1.1-continued

| | | | | | | | |
|---|---|---|---|---|---|---|---|
| 4135 | 2418 | 1 | 0.066992 | 0.067348 | 0.065523 | 0.067075 | 0.069445 |
| 4105 | 2436 | 1 | 0.066911 | 0.066291 | 0.066551 | 0.064987 | 0.067336 |
| 4060 | 2463 | 1 | 0.10946 | 0.11196 | 0.11349 | 0.11337 | 0.10903 |
| 4040 | 2475 | 1 | 0.10273 | 0.10157 | 0.10564 | 0.10211 | 0.096959 |
| RON clear | | | 99.4 | 99.2 | 99 | 99.3 | 99.4 |
| MON Clear | | | 88.4 | 88.2 | 88 | 88.1 | 88.4 |
| TV hpa | | | 700 | 705.0 | 710 | 715 | 690 |
| Volatility | | | 980 | 975.0 | 983 | 967 | 975 |
| % Dist 100° C. | | | 58 | 54.7 | 54 | 58 | 52 |
| % Dist 70° C. | | | 36.8 | 37 | 39 | 37 | 35 |
| Resin | | | 1.4 | 1.6 | 1.2 | 1.7 | 1.8 |
| % Sulphur | | | 0.038 | 0.043 | 0.035 | 0.045 | 0.048 |
| Benzene % Vol | | | 0.7 | 0.8 | 0.6 | 0.85 | 0.9 |
| MTBE | | | 5.6 | 5.8 | 4.7 | 6.3 | 6.5 |

TABLE 2a.1

NIR Spectra of Unleaded mixed fuel and base fuel and additives

| $\lambda$ (cm−1) | $\lambda$ (nm) | SUPER FUEL | BASE FUEL | BUTANE | HEN | ISOM | MTBE | REF |
|---|---|---|---|---|---|---|---|---|
| 4720 | 2119 | 0.0013833 | 0.0013286 | 0.00036614 | 0.0048746 | 0.00045176 | 0.00039505 | 0.0017899 |
| 4670 | 2141 | 0.015401 | 0.015698 | 0.00059139 | 0.035929 | 0.0018107 | 0.00079685 | 0.02742 |
| 4640 | 2155 | 0.014458 | 0.014786 | 0.0015483 | 0.03355 | 0.0020854 | 0.0019907 | 0.026581 |
| 4615 | 2167 | 0.021629 | 0.02193 | 0.002432 | 0.048472 | 0.0033767 | 0.0033645 | 0.035613 |
| 4585 | 2181 | 0.013173 | 0.013556 | 0.0039046 | 0.026822 | 0.0032492 | 0.0043356 | 0.026327 |
| 4485 | 2230 | 0.010699 | 0.010705 | 0.013766 | 0.01651 | 0.0057573 | 0.013241 | 0.012712 |
| 4460 | 2242 | 0.015318 | 0.015646 | 0.016717 | 0.018858 | 0.010108 | 0.027911 | 0.0181 |
| 4385 | 2281 | 0.094023 | 0.094638 | 0.10437 | 0.081125 | 0.095255 | 0.13276 | 0.084676 |
| 4332 | 2308 | 0.12974 | 0.13083 | 0.14701 | 0.094876 | 0.1474 | 0.18122 | 0.11297 |
| 4305 | 2323 | 0.10626 | 0.10476 | 0.12279 | 0.093425 | 0.11981 | 0.063885 | 0.10927 |
| 4260 | 2347 | 0.10094 | 0.098881 | 0.11439 | 0.088133 | 0.11705 | 0.074657 | 0.090487 |
| 4210 | 2375 | 0.065672 | 0.065902 | 0.074313 | 0.054295 | 0.072316 | 0.091152 | 0.058007 |
| 4170 | 2398 | 0.065289 | 0.065063 | 0.057805 | 0.049811 | 0.074797 | 0.095725 | 0.05451 |
| 4135 | 2418 | 0.069147 | 0.068664 | 0.079862 | 0.046235 | 0.085847 | 0.083448 | 0.049256 |
| 4105 | 2436 | 0.068641 | 0.067702 | 0.089697 | 0.050826 | 0.082082 | 0.06768 | 0.053229 |
| 4060 | 2463 | 0.10677 | 0.10794 | 0.0875 | 0.12437 | 0.099989 | 0.076993 | 0.12989 |
| 4040 | 2475 | 0.10145 | 0.10197 | 0.083674 | 0.13189 | 0.079524 | 0.081235 | 0.10917 |
| RON clear | | 99.1 | | | | | | |
| MON clear | | 88.2 | | | | | | |
| Vapour Pressure | | 731.74 | | | | | | |
| Volatilite | | 985 | | | | | | |
| % Dist 100° C. | | 49.93 | | | | | | |
| % Dist 70° C. | | 34.4 | | | | | | |

TABLE 2a.2

Effect of addition of MTBE on the Super Fuel

| | | Weighting | Mixture + 5% MTBE Exp. | Estimated | 2A | 2B | 2C |
|---|---|---|---|---|---|---|---|
| Proximity Index | | | | 0.000019069 | 0.00004957 | 0.000060618 | 0.000068613 |
| $\lambda$ (cm−1) | $\lambda$ (nm) | | | | | | |
| 4720 | 2119 | 1 | 0.0013362 | 0.0012761 | 0.0012748 | 0.0012691 | 0.0012845 |
| 4670 | 2141 | 1 | 0.014705 | 0.014562 | 0.014384 | 0.014083 | 0.015218 |
| 4640 | 2155 | 1 | 0.013864 | 0.013804 | 0.014523 | 0.013567 | 0.013323 |
| 4615 | 2167 | 1 | 0.020759 | 0.02143 | 0.021489 | 0.021104 | 0.021698 |
| 4585 | 2181 | 1 | 0.012752 | 0.01255 | 0.012204 | 0.01312 | 0.012327 |
| 4485 | 2230 | 1 | 0.01082 | 0.010514 | 0.01041 | 0.01042 | 0.010712 |
| 4460 | 2242 | 1 | 0.015917 | 0.015584 | 0.016158 | 0.015226 | 0.015368 |
| 4385 | 2281 | 1 | 0.095868 | 0.096666 | 0.096107 | 0.09918 | 0.094711 |
| 4332 | 2308 | 1 | 0.13219 | 0.13256 | 0.1298 | 0.12971 | 0.13817 |
| 4305 | 2323 | 1 | 0.10425 | 0.10443 | 0.10689 | 0.10497 | 0.10142 |
| 4260 | 2347 | 1 | 0.099691 | 0.10039 | 0.10436 | 0.098324 | 0.098495 |
| 4210 | 2375 | 1 | 0.066885 | 0.066455 | 0.066544 | 0.065782 | 0.067039 |
| 4170 | 2398 | 1 | 0.066738 | 0.067485 | 0.065091 | 0.069061 | 0.068303 |
| 4135 | 2418 | 1 | 0.069828 | 0.071186 | 0.069457 | 0.07235 | 0.07175 |
| 4105 | 2436 | 1 | 0.068596 | 0.066773 | 0.065937 | 0.06768 | 0.0667 |
| 4060 | 2463 | 1 | 0.10535 | 0.10236 | 0.10385 | 0.101 | 0.10222 |
| 4040 | 2475 | 1 | 0.10049 | 0.10197 | 0.10152 | 0.10314 | 0.10126 |

TABLE 2a.2-continued

|  | Reference SUPER98 |  |  |  |  |
|---|---|---|---|---|---|
| RON clear | 99.1 | 99.6 | 99.7 | 99.5 | 99.5 |
| MON clear | 88.2 | 88.7 | 88.9 | 88.5 | 88.7 |
| Vapour Pressure | 731.74 | 718.8 | 711.2 | 720.0 | 725.2 |
| Volatility | 985 | 972.3 | 970.0 | 979.2 | 967.6 |
| % Dist 100° C. | 49.93 | 52.3 | 52.0 | 54.0 | 50.8 |
| % Dist 70° C. | 34.4 | 35.8 | 36.3 | 35.4 | 35.8 |

TABLE 2a.3

Blending Indices and Blending Order

|  | (blending order) | Base Fuel | Butane | HEN | ISOM | MTBE | REF |
|---|---|---|---|---|---|---|---|
| Volume Fraction |  | 19.30% | 4.10% | 31.70% | 32.10% | 5.60% | 7.2% |
| RON clear | 99.4 | 100.2 | 97.5 | 103.6 | 93.0 | 109.6 | 100.7 |
| MON clear | 88.2 | 88.0 | 88.5 | 88.0 | 86.7 | 98.7 | 88.42 |
| Vapour Pressure | 709.1 | 767.0 | 4700.0 | 98.7 | 923.0 | 460 | 208.2 |
| Volatility | 972.4 | 975.0 | 5000.0 | 212.0 | 1430.0 | 718.3 | 177.3 |
| % Dist 100° C. | 54.9 | 50.2 | 200.0 | −5.0 | 97.5 | 99.7 | 24 |
| % Dist 70° C. | 37.8 | 31.3 | 142.8 | −12.9 | 84.2 | 63.8 | −8.3 |

TABLE 2a.4

Comparison of the result obtained via the blending order and those of the product obtained

|  |  |  | Product | | | | |
|---|---|---|---|---|---|---|---|
|  | | Weight | Made | Estimated | 2D | 2E | 2F |
| Proximity Index | | | | 0.000027526 | 0.000067452 | 0.000072577 | 0.000096807 |
| λ (cm−1) | λ (nm) | | | | | | |
| 4720 | 2119 | 1 | 0.0021031 | 0.0021115 | 0.0021985 | 0.0020678 | 0.0020683 |
| 4670 | 2141 | 1 | 0.01696 | 0.016887 | 0.017029 | 0.016831 | 0.016801 |
| 4640 | 2155 | 1 | 0.016172 | 0.016464 | 0.017171 | 0.015695 | 0.016527 |
| 4615 | 2167 | 1 | 0.023426 | 0.022955 | 0.022671 | 0.022765 | 0.023429 |
| 4585 | 2181 | 1 | 0.014407 | 0.014379 | 0.014241 | 0.014863 | 0.014034 |
| 4485 | 2230 | 1 | 0.011377 | 0.011472 | 0.011516 | 0.011788 | 0.011112 |
| 4460 | 2242 | 1 | 0.015794 | 0.015825 | 0.015718 | 0.015331 | 0.016428 |
| 4385 | 2281 | 1 | 0.092392 | 0.090762 | 0.09071 | 0.092874 | 0.088701 |
| 4332 | 2308 | 1 | 0.127 | 0.12402 | 0.12292 | 0.1241 | 0.12505 |
| 4305 | 2323 | 1 | 0.10482 | 0.10678 | 0.1021 | 0.10946 | 0.10879 |
| 4260 | 2347 | 1 | 0.10001 | 0.099412 | 0.098621 | 0.095524 | 0.10409 |
| 4210 | 2375 | 1 | 0.065489 | 0.06726 | 0.067463 | 0.066664 | 0.067653 |
| 4170 | 2398 | 1 | 0.063954 | 0.06449 | 0.066434 | 0.064491 | 0.062546 |
| 4135 | 2418 | 1 | 0.066992 | 0.067348 | 0.065523 | 0.067075 | 0.069445 |
| 4105 | 2436 | 1 | 0.066911 | 0.066291 | 0.066551 | 0.064987 | 0.067336 |
| 4060 | 2463 | 1 | 0.10946 | 0.11196 | 0.11349 | 0.11337 | 0.10903 |
| 4040 | 2475 | 1 | 0.10273 | 0.10157 | 0.10564 | 0.10211 | 0.096959 |
|  |  | (blending order) | Measured standards | | | | |
| RON clear |  | 99.4 | 99.4 | 99.2 | 99 | 99.3 | 99.4 |
| MON clear |  | 88.2 | 88.4 | 88.2 | 88 | 88.1 | 88.4 |
| Vapour Pressure |  | 709.1 | 700 | 705.0 | 710 | 715 | 690 |
| Volatility |  | 972.4 | 980 | 975.0 | 983 | 967 | 975 |
| % Dist 100° C. |  | 54.9 | 58 | 54.7 | 54 | 58 | 52 |
| % Dist 70° C. |  | 37.8 | 36.8 | 37 | 39 | 37 | 35 |

TABLE 2b.1

NMR spectrum of Target Super Fuel, and base stocks available

| $\lambda$ (cm-1) | $\lambda$ (nm) | Target | Gasoline | FCC | HEN | ISOM | REF |
|---|---|---|---|---|---|---|---|
| 4720 | 2119 | 0.0014234 | 0.0012695 | 0.0029238 | 0.0045838 | 0.0004093 | 0.001657 |
| 4670 | 2141 | 0.0092828 | 0.0090594 | 0.0059667 | 0.037011 | 0.0020427 | 0.024449 |
| 4640 | 2155 | 0.0092599 | 0.00908 | 0.0068202 | 0.033868 | 0.0021945 | 0.023848 |
| 4615 | 2167 | 0.013236 | 0.012989 | 0.0092342 | 0.046361 | 0.0035967 | 0.032231 |
| 4585 | 2181 | 0.0098247 | 0.0096662 | 0.0077879 | 0.028857 | 0.0033395 | 0.023754 |
| 4485 | 2230 | 0.010777 | 0.010379 | 0.014512 | 0.015486 | 0.0058411 | 0.012233 |
| 4460 | 2242 | 0.014409 | 0.014075 | 0.016828 | 0.018119 | 0.0102 | 0.017515 |
| 4385 | 2281 | 0.093329 | 0.093268 | 0.095498 | 0.078888 | 0.095201 | 0.085595 |
| 4332 | 2308 | 0.14045 | 0.1408 | 0.1543 | 0.092697 | 0.14681 | 0.11852 |
| 4305 | 2323 | 0.12096 | 0.12085 | 0.13213 | 0.091686 | 0.11947 | 0.11078 |
| 4260 | 2347 | 0.11073 | 0.11062 | 0.11559 | 0.086428 | 0.11763 | 0.093562 |
| 4210 | 2375 | 0.068913 | 0.069012 | 0.073406 | 0.052861 | 0.072136 | 0.060461 |
| 4170 | 2398 | 0.069683 | 0.069948 | 0.073798 | 0.049022 | 0.075191 | 0.05775 |
| 4135 | 2418 | 0.071227 | 0.071736 | 0.067143 | 0.045477 | 0.085471 | 0.05259 |
| 4105 | 2436 | 0.070003 | 0.070819 | 0.065003 | 0.050963 | 0.082203 | 0.056176 |
| 4060 | 2463 | 0.10201 | 0.10186 | 0.089357 | 0.13909 | 0.099705 | 0.1243 |
| 4040 | 2475 | 0.084489 | 0.08458 | 0.0697 | 0.1286 | 0.079381 | 0.10458 |
| RON clear | | 97.9 | | | | | |
| MON clear | | 86.2 | | | | | |
| Vapour Pressure | | 596 | | | | | |
| Volatility | | 905.4 | | | | | |
| % Dist 100° C. | | 62.54 | | | | | |
| % Dist 70° C. | | 42.24 | | | | | |

TABLE 2b.2

Effect of addition of 5% FCC gasoline on Super 97 Product

| | | | Mixture | | | | |
|---|---|---|---|---|---|---|---|
| | | Weight | Actual | Estimated | 2G | 2H | 2J |
| Proximity Index | | | | 3.41E-05 | 5.77E-05 | 6.53E-05 | 7.88E-05 |
| Wavelength | | | | | | | |
| $\lambda$ (cm-1) | $\lambda$ (nm) | | | | | | |
| 4720 | 2119 | 1 | 0.001495 | 0.001416 | 0.001411 | 0.001414 | 0.001421 |
| 4670 | 2141 | 1 | 0.009125 | 0.008837 | 0.008658 | 0.008768 | 0.009085 |
| 4640 | 2155 | 1 | 0.009144 | 0.008948 | 0.009016 | 0.008955 | 0.008874 |
| 4615 | 2167 | 1 | 0.013045 | 0.012691 | 0.012631 | 0.013035 | 0.012407 |
| 4585 | 2181 | 1 | 0.009728 | 0.009605 | 0.009454 | 0.009682 | 0.009679 |
| 4485 | 2230 | 1 | 0.010955 | 0.010851 | 0.010639 | 0.010909 | 0.011005 |
| 4460 | 2242 | 1 | 0.014524 | 0.014847 | 0.01487 | 0.014917 | 0.014754 |
| 4385 | 2281 | 1 | 0.093432 | 0.094816 | 0.094259 | 0.096722 | 0.093466 |
| 4332 | 2308 | 1 | 0.14111 | 0.14368 | 0.14703 | 0.13759 | 0.1464 |
| 4305 | 2323 | 1 | 0.12149 | 0.12506 | 0.12261 | 0.12658 | 0.12598 |
| 4260 | 2347 | 1 | 0.11096 | 0.11021 | 0.11119 | 0.11141 | 0.10805 |
| 4210 | 2375 | 1 | 0.069127 | 0.06648 | 0.066676 | 0.065499 | 0.067266 |
| 4170 | 2398 | 1 | 0.069879 | 0.068946 | 0.067881 | 0.069493 | 0.069464 |
| 4135 | 2418 | 1 | 0.071032 | 0.070704 | 0.069102 | 0.072032 | 0.070979 |
| 4105 | 2436 | 1 | 0.069765 | 0.069612 | 0.071611 | 0.069153 | 0.068074 |
| 4060 | 2463 | 1 | 0.1014 | 0.1015 | 0.10061 | 0.101 | 0.10289 |
| 4040 | 2475 | 1 | 0.083785 | 0.081801 | 0.082343 | 0.082854 | 0.080207 |
| | | Reference SUPER97 | | | | | |
| RON clear | | 97.9 | | 97.6 | 97.7 | 97.5 | 97.6 |
| MON clear | | 86.2 | | 85.9 | 86.1 | 85.7 | 85.9 |
| Vapour Pressure | | 596 | | 586.1 | 590.0 | 584.2 | 584.2 |
| Volatility | | 905.4 | | 892.2 | 901.0 | 887.5 | 888.0 |
| % Dist 100° C. | | 62.54 | | 62.3 | 62.8 | 62.6 | 61.4 |
| % Dist 70° C. | | 42.24 | | 41.7 | 42.5 | 41.7 | 40.9 |

In this Table 3.41E-05 means $3.41 \times 10^{-5}$

TABLE 2b.3

Blending Indices and Blending order

|  | (blending order) | Gasoline | FCC | HEN | ISOM | REF |
|---|---|---|---|---|---|---|
| Volume Fraction |  | 12.93% | 31.85% | 8.46% | 37.55% | 9.20% |
| RON clear | 97.7 | 97.9 | 91.6 | 101.1 | 101.5 | 100. |
| MON clear | 86.3 | 86.4 | 79.9 | 83.5 | 92 | 87.9 |
| Vapour Pressure | 589.9 | 648.0 | 388.1 | 137.7 | 930.0 | 235.0 |
| Volatility | 952.7 | 968.5 | 628.2 | 274.2 | 1559.0 | 204.7 |
| % Dist 100° C. | 65.5 | 63.2 | 57.5 | 6.3 | 96.0 | 26.4 |
| % Dist 70° C. | 45.4 | 43.1 | 30.9 | −10.7 | 83.3 | −4.3 |

TABLE 2b.4

Comparison between the results from the blending order and the product obtained

|  |  |  | Product |  |  |  |  |
|---|---|---|---|---|---|---|---|
|  |  | Weight | Measured | Estimated | 2K | 2L | 2M |
| Proximity Index |  |  |  | 8.41E−05 | 5.36E−05 | 0.000159 | 0.000199 |
| λ (cm−1) | λ (nm) |  |  |  |  |  |  |
| 4720 | 2119 | 1 | 0.001742 | 0.001809 | 0.001775 | 0.001851 | 0.001802 |
| 4670 | 2141 | 1 | 0.009508 | 0.009166 | 0.009131 | 0.009262 | 0.009104 |
| 4640 | 2155 | 1 | 0.008698 | 0.00926 | 0.009326 | 0.009695 | 0.008759 |
| 4615 | 2167 | 1 | 0.012758 | 0.013206 | 0.012772 | 0.013574 | 0.01327 |
| 4585 | 2181 | 1 | 0.009725 | 0.009549 | 0.009242 | 0.009921 | 0.009484 |
| 4485 | 2230 | 1 | 0.010459 | 0.010438 | 0.010486 | 0.010336 | 0.010493 |
| 4460 | 2242 | 1 | 0.014142 | 0.014252 | 0.014878 | 0.013896 | 0.013982 |
| 4385 | 2281 | 1 | 0.090899 | 0.093317 | 0.092897 | 0.09338 | 0.093676 |
| 4332 | 2308 | 1 | 0.13685 | 0.13974 | 0.13652 | 0.13589 | 0.14683 |
| 4305 | 2323 | 1 | 0.11596 | 0.12103 | 0.1195 | 0.1248 | 0.11879 |
| 4260 | 2347 | 1 | 0.11499 | 0.1128 | 0.11271 | 0.11216 | 0.11352 |
| 4210 | 2375 | 1 | 0.071524 | 0.068713 | 0.071255 | 0.068318 | 0.066566 |
| 4170 | 2398 | 1 | 0.070662 | 0.070304 | 0.069855 | 0.069388 | 0.071669 |
| 4135 | 2418 | 1 | 0.072077 | 0.071069 | 0.070001 | 0.07464 | 0.068566 |
| 4105 | 2436 | 1 | 0.069448 | 0.071756 | 0.073371 | 0.071076 | 0.070822 |
| 4060 | 2463 | 1 | 0.10444 | 0.10095 | 0.10163 | 0.098515 | 0.10269 |
| 4040 | 2475 | 1 | 0.086116 | 0.08264 | 0.084647 | 0.083297 | 0.079975 |
|  |  | (blending order) | Measured standards |  |  |  |  |
| RON clear |  | 97.7 | 97.5 | 97.7 | 97.8 | 97.5 | 97.7 |
| MON clear |  | 86.3 | 86.4 | 86.2 | 86 | 86.1 | 86.5 |
| Vapour Pressure |  | 589.9 | 595 | 598.0 | 596 | 600 | 598 |
| Volatility |  | 952.7 | 949 | 956.7 | 955 | 960 | 955 |
| % Dist 100° C. |  | 65.5 | 62 | 63.0 | 66 | 63 | 60 |
| % Dist 70° C. |  | 45.4 | 47 | 44.2 | 42 | 46.5 | 44 |

TABLE 3.1

Determination of cetane index and other properties of a gas oil

|  |  |  | Gas Oil A |  |  |  |
|---|---|---|---|---|---|---|
|  |  | Weight | Measured | Estimated | 3B | 3C |
| Proximity Index |  |  |  | 1.71E−06 | 1.39E−06 | 2.23E−06 |
| λ (cm−1) | λ (nm) |  |  |  |  |  |
| 4720 | 2118.6 | 1 | 0.000120383 | 0.000126618 | 0.000139825 | 0.000113411 |
| 4672 | 2140.4 | 1 | 0.001962853 | 0.002013913 | 0.002015876 | 0.002011949 |
| 4640 | 2155.2 | 1 | 0.003434747 | 0.003415109 | 0.003438675 | 0.003391543 |
| 4616 | 2166.4 | 1 | 0.004544314 | 0.004490799 | 0.004476561 | 0.004505037 |
| 4584 | 2181.5 | 1 | 0.004729896 | 0.0046754 | 0.00463465 | 0.004716149 |
| 4484 | 2230.2 | 1 | 0.007119883 | 0.006932337 | 0.006908771 | 0.006955903 |
| 4460 | 2242.2 | 1 | 0.010349409 | 0.010133388 | 0.010064653 | 0.010202122 |
| 4384 | 2281 | 1 | 0.074606084 | 0.074925207 | 0.074930117 | 0.074920298 |
| 4332 | 2308.4 | 1 | 0.158677852 | 0.157745031 | 0.15799051 | 0.157499551 |
| 4304 | 2323.4 | 1 | 0.101824835 | 0.102266697 | 0.102217602 | 0.102315793 |

TABLE 3.1-continued

| | | | | | | |
|---|---|---|---|---|---|---|
| 4260 | 2347.4 | 1 | 0.131871507 | 0.131331453 | 0.131380548 | 0.131282357 |
| 4208 | 2376.4 | 1 | 0.088627865 | 0.088637684 | 0.08855913 | 0.088716237 |
| 4168 | 2399.2 | 1 | 0.092899205 | 0.093012126 | 0.093105408 | 0.092918844 |
| 4132 | 2420.1 | 1 | 0.084503812 | 0.08475911 | 0.084827844 | 0.084690376 |
| 4104 | 2436.6 | 1 | 0.081106377 | 0.081297851 | 0.081361676 | 0.081234027 |
| 4060 | 2463.1 | 1 | 0.08642837 | 0.086487285 | 0.086487285 | 0.086487285 |
| 4040 | 2475.2 | 1 | 0.067192608 | 0.06740372 | 0.067418449 | 0.067388991 |
| Cetane Index | | | 52 | 52.5 | 53.3 | 51.7 |
| Cetane Number | | | 55.3 | 52.75 | 52.1 | 53.4 |
| Density 15° C. | | | 0.8434 | 0.84085 | 0.8385 | 0.8432 |
| Flash Point | | | 62 | 57.5 | 60 | 55 |
| % Sulphur | | | 0.29 | 0.25 | 0.23 | 0.27 |
| Cloud Point | | | 5.1 | 5.5 | 5 | 6 |
| Filtrability | | | 1 | 0.5 | 1 | 0 |
| Viscosity 40° C. | | | 3.1 | 3.7 | 3.7 | 3.7 |

TABLE 4.1

Determination of yields and properties of cuts from distillation of mixture of crude feed oils

| | | | Charse 4C | | | |
|---|---|---|---|---|---|---|
| | | Weight | Measured | Estimated | 4A | 4B |
| Proximity Index | | | | 9.98E−07 | 1.21E−06 | 1.33E−06 |
| λ (cm−1) | λ (nm) | | | | | |
| 4672 | 2140.4 | 1 | 0.001777942 | 0.001748627 | 0.001771733 | 0.00172552 |
| 4640 | 2155.2 | 1 | 0.003139917 | 0.003211964 | 0.003256211 | 0.003167717 |
| 4616 | 2166.4 | 1 | 0.00377911 | 0.003827795 | 0.003835639 | 0.003819952 |
| 4584 | 2181.5 | 1 | 0.003794844 | 0.003797791 | 0.003829737 | 0.003765845 |
| 4484 | 2230.2 | 1 | 0.006094959 | 0.00614454 | 0.006272386 | 0.006016694 |
| 4460 | 2242.2 | 1 | 0.009258476 | 0.009155818 | 0.009276757 | 0.009034879 |
| 4384 | 2281 | 1 | 0.078089814 | 0.077898738 | 0.077667019 | 0.078130457 |
| 4332 | 2308.4 | 1 | 0.15773336 | 0.157794497 | 0.157793411 | 0.157795584 |
| 4304 | 2323.4 | 1 | 0.104631107 | 0.1045241 | 0.104179066 | 0.104869135 |
| 4260 | 2347.4 | 1 | 0.130690546 | 0.130249322 | 0.130445176 | 0.130053468 |
| 4208 | 2376.4 | 1 | 0.087815393 | 0.087751054 | 0.087838988 | 0.08766312 |
| 4172 | 2396.9 | 1 | 0.091208037 | 0.090879399 | 0.090878774 | 0.090880025 |
| 4132 | 2420.1 | 1 | 0.084648925 | 0.084706329 | 0.08465164 | 0.084761019 |
| 4104 | 2436.6 | 1 | 0.0824855 | 0.082364989 | 0.082389016 | 0.082340962 |
| 4060 | 2463.1 | 1 | 0.087068028 | 0.087578898 | 0.087475 | 0.087682795 |
| 4040 | 2475.2 | 1 | 0.067784043 | 0.068366138 | 0.068439449 | 0.068292827 |
| Density 15° C. | | | 0.8663 | 0.86555 | 0.8646 | 0.8665 |
| % Gasoline | | | 7.4 | 7.4 | 7.4 | 7.4 |
| % Benzine | | | 7.6 | 7.2 | 7.3 | 7.2 |
| % Naphta | | | 4.3 | 4.5 | 4.5 | 4.5 |
| % Petrol | | | 8.5 | 8.5 | 8.6 | 8.4 |
| % light gas oil LGO | | | 18.9 | 18.8 | 19.2 | 18.5 |
| % Heavy gas oil | | | 4.5 | 4.5 | 4.6 | 4.4 |
| % Residue RAT | | | 49 | 49.2 | 48.6 | 49.8 |
| % Paraffines Naphta | | | 52.2 | 52.1 | 53.1 | 51.2 |
| Flash Point Petrol | | | 59.2 | 59.5 | 59.8 | 59.3 |
| Cloud point LGO | | | −8.1 | −8.1 | −8.8 | −7.5 |
| % Sulphur RAT | | | 2.8 | 2.8 | 2.8 | 2.9 |
| Viscosity 100° C. RAT | | | 53.16 | 52.72 | 48.53 | 56.91 |

TABLE 5.1

On line determination of properties of a mixture of crude oils

| | | | Mixture 4C | | | |
|---|---|---|---|---|---|---|
| | | Weight | Measured | Estimated | 4A | 4B |
| Proximity Index | | | | 1.04E−06 | 1.27E−06 | 1.35E−06 |
| λ (cm−1) | λ (nm) | | | | | |
| 4672 | 2140.4 | 1 | 0.001777942 | 0.001747949 | 0.001771058 | 0.00172484 |
| 4640 | 2155.2 | 1 | 0.003139917 | 0.00321072 | 0.003254971 | 0.003166468 |

TABLE 5.1-continued

| | | | | | | |
|---|---|---|---|---|---|---|
| 4616 | 2166.4 | 1 | 0.00377911 | 0.003826312 | 0.003834179 | 0.003818445 |
| 4584 | 2181.5 | 1 | 0.003794844 | 0.003796319 | 0.003828279 | 0.00376436 |
| 4484 | 2230.2 | 1 | 0.006094959 | 0.006142161 | 0.006269999 | 0.006014322 |
| 4460 | 2242.2 | 1 | 0.009258476 | 0.009152272 | 0.009273227 | 0.009031317 |
| 4384 | 2281 | 1 | 0.078089814 | 0.077868554 | 0.077637461 | 0.078099647 |
| 4332 | 2308.4 | 1 | 0.15773336 | 0.15773336 | 0.15773336 | 0.15773336 |
| 4304 | 2323.4 | 1 | 0.104631107 | 0.1044836 | 0.104139419 | 0.104827782 |
| 4260 | 2347.4 | 1 | 0.130690546 | 0.130198858 | 0.130395533 | 0.130002183 |
| 4208 | 2376.4 | 1 | 0.087815393 | 0.087717055 | 0.087805559 | 0.087628552 |
| 4172 | 2396.9 | 1 | 0.091208037 | 0.090844188 | 0.090844188 | 0.090844188 |
| 4132 | 2420.1 | 1 | 0.084648925 | 0.08467351 | 0.084619424 | 0.084727595 |
| 4104 | 2436.6 | 1 | 0.0824855 | 0.082333077 | 0.082357661 | 0.082308493 |
| 4060 | 2463.1 | 1 | 0.087068028 | 0.087544965 | 0.08744171 | 0.087648219 |
| 4040 | 2475.2 | 1 | 0.067784043 | 0.06833965 | 0.068413403 | 0.068265897 |
| Density | | | 0.8663 | 0.86555 | 0.8646 | 0.8665 |
| % Sulphur | | | 1.6 | 1.65 | 1.6 | 1.7 |
| Viscosity 100° C. | | | 2.27 | 2.265 | 2.36 | 2.17 |
| % Conradson Carbon | | | 4.8 | 5 | 4.8 | 5.1 |
| % Paraffin content | | | 5 | 4.95 | 4.9 | 5 |

TABLE 6.1

Determination of the Properties of a reformer feed

| | | Feed 6D | | | | |
|---|---|---|---|---|---|---|
| | Weight | Measured | Estimated | 6A | 6B | 6C |
| Proximity Index | | | | 5.7E-4 | 8.2E-5 | 9.7E-5 |
| λ (nm) | | | | | | |
| 2210 | 1 | 0.04624 | 0.04659897 | 0.04648 | 0.04671 | 0.04659 |
| 2260 | 1 | 0.18118 | 0.18154437 | 0.18233 | 0.18132 | 0.18085 |
| 2266 | 1 | 0.25391 | 0.25482278 | 0.25605 | 0.25439 | 0.25386 |
| 2276 | 1 | 0.33866 | 0.33942652 | 0.3412 | 0.33844 | 0.33857 |
| 2286 | 1 | 0.33776 | 0.33747772 | 0.3395 | 0.33634 | 0.33652 |
| 2307 | 1 | 0.54602 | 0.54558172 | 0.54286 | 0.54922 | 0.54375 |
| 2328 | 1 | 0.38819 | 0.38770261 | 0.38812 | 0.38791 | 0.38685 |
| 2344 | 1 | 0.4557 | 0.4561672 | 0.45568 | 0.45592 | 0.45717 |
| 2376 | 1 | 0.31751 | 0.31727184 | 0.31483 | 0.32067 | 0.31543 |
| 2397 | 1 | 0.33674 | 0.33644352 | 0.33466 | 0.33858 | 0.33561 |
| 2408 | 1 | 0.31787 | 0.31746329 | 0.31737 | 0.31904 | 0.31525 |
| 2418 | 1 | 0.32524 | 0.32334235 | 0.3244 | 0.32341 | 0.32186 |
| 2437 | 1 | 0.34758 | 0.34790932 | 0.34915 | 0.34543 | 0.34996 |
| 2457 | 1 | 0.38142 | 0.38057046 | 0.3793 | 0.38076 | 0.38195 |
| % Linear Saturated | | 33.0 | 32.6 | 32.5 | 32.4 | 32.9 |
| % Isoparaffins | | 30.1 | 30.8 | 31.4 | 31.1 | 29.9 |
| % Naphthenes | | 29.3 | 29.2 | 29.2 | 28.5 | 30 |
| % Aromatics | | 7.6 | 7.4 | 6.9 | 8 | 7.2 |
| Density | | 0.7151 | 0.7158 | 0.7152 | 0.7167 | 0.7155 |

TABLE 7.1

Determination of Properties of feed to FCC reactor and yields and properties of products

| | | | Feed 7D | | | |
|---|---|---|---|---|---|---|
| | | Weight | Measured | Estimated | 7A | 7B |
| Proximity Index | | | | 1.10E-06 | 1.28E-06 | 1.30E-06 |
| λ (cm-1) | λ (nm) | | | | | |
| 4720 | 2118.6 | 1 | 0.00024017 | 0.000283004 | 0.000238346 | 0.000327662 |
| 4672 | 2140.4 | 1 | 0.002238801 | 0.002010364 | 0.001890879 | 0.00212985 |
| 4640 | 2155.2 | 1 | 0.004237234 | 0.003903227 | 0.003874117 | 0.003932336 |
| 4612 | 2168.3 | 1 | 0.005237444 | 0.004972667 | 0.004866233 | 0.005079102 |
| 4584 | 2181.5 | 1 | 0.005332797 | 0.005055095 | 0.005031089 | 0.005079102 |
| 4484 | 2230.2 | 1 | 0.007970887 | 0.007756354 | 0.007744263 | 0.007768446 |

TABLE 7.1-continued

| | | | | | | |
|---|---|---|---|---|---|---|
| 4460 | 2242.2 | 1 | 0.011303264 | 0.011210967 | 0.011212199 | 0.011209736 |
| 4384 | 2281 | 1 | 0.072994455 | 0.07273491 | 0.07292398 | 0.072545839 |
| 4332 | 2308.4 | 1 | 0.152067643 | 0.152159348 | 0.151945649 | 0.152373047 |
| 4304 | 2323.4 | 1 | 0.100517606 | 0.100397569 | 0.100601923 | 0.100193214 |
| 4260 | 2347.4 | 1 | 0.131209247 | 0.131514201 | 0.131487607 | 0.131540794 |
| 4212 | 2374.2 | 1 | 0.091618024 | 0.091623192 | 0.091564633 | 0.091681751 |
| 4168 | 2399.2 | 1 | 0.094011773 | 0.094322962 | 0.09427582 | 0.094370104 |
| 4132 | 2420.1 | 1 | 0.086184908 | 0.086675314 | 0.086678538 | 0.08667209 |
| 4104 | 2436.6 | 1 | 0.081457005 | 0.081916022 | 0.081981133 | 0.081850912 |
| 4060 | 2463.1 | 1 | 0.084267922 | 0.084318052 | 0.084444043 | 0.08419206 |
| 4040 | 2475.2 | 1 | 0.06911082 | 0.069146752 | 0.069239547 | 0.069053957 |
| Density | | | 0.926 | 0.9225 | 0.922 | 0.923 |
| % Sulphur | | | 1.97 | 1.85 | 1.83 | 1.87 |
| Aniline Point | | | 83.5 | 83.2 | 78.2 | 88.2 |
| Viscosity 100° C. | | | 8.8 | 9.1 | 8.7 | 9.5 |
| Temp. 50% distilled | | | 461 | 464 | 457 | 471 |
| KUOP | | | 11.8 | 11.85 | 11.8 | 11.9 |
| Mol. Weight | | | 450.6 | 449.95 | 434.5 | 465.4 |
| % Aromatic Carbon | | | 21.8 | 21.2 | 21.6 | 20.9 |
| CRACKABILITY | | | 2.47 | 2.57 | 2.55 | 2.59 |
| COKABILITY | | | 1.01 | 1.00 | 0.99 | 1.01 |
| GASOIL INDEX | | | 1.55 | 1.515 | 1.54 | 1.49 |
| GASOLINE INDEX | | | 0.99 | 0.985 | 0.99 | 0.98 |
| Gasoline Yield (%) | | | 45 | 44.5 | 43 | 46 |
| Residue Yield (%) | | | 12 | 11.25 | 13 | 9.5 |
| RON Clear Gasoline | | | 92.7 | 92.4 | 92.4 | 92.4 |

TABLE 8.1

On line Determination of properties of feed to hydrogenation unit for gasoline

| | | Weight | Feed 8F | 8A | 8B | 8C | 8D | 8E |
|---|---|---|---|---|---|---|---|---|
| | Prox. Index | | Measured | Estimated 0.0000042 | 0.0000034 | 0.0000047 | 0.0000114 | 0.0000130 | 0.0000222 |
| λ (cm −1) | λ (nm) | | | | | | | | |
| 8949 | 1117.5 | 1 | 0.006443 | 0.0064568 | 0.006082 | 0.00695 | 0.006137 | 0.006508 | 0.006607 |
| 8795 | 1137 | 1 | 0.036107 | 0.035343 | 0.035282 | 0.035954 | 0.035428 | 0.035343 | 0.034706 |
| 8780 | 1139 | 1 | 0.039287 | 0.0385 | 0.038591 | 0.039092 | 0.038516 | 0.038491 | 0.037812 |
| 8764 | 1141 | 1 | 0.040899 | 0.040123 | 0.040341 | 0.040719 | 0.040019 | 0.040077 | 0.03946 |
| 8737 | 1144.5 | 1 | 0.039495 | 0.038904 | 0.039152 | 0.039435 | 0.038641 | 0.038923 | 0.038369 |
| 8688 | 1151 | 1 | 0.027962 | 0.027745 | 0.027983 | 0.028106 | 0.027187 | 0.027774 | 0.027677 |
| 8673 | 1153 | 1 | 0.024452 | 0.024293 | 0.024501 | 0.024563 | 0.023745 | 0.024321 | 0.024335 |
| 8651 | 1156 | 1 | 0.020612 | 0.020536 | 0.02067 | 0.020691 | 0.020084 | 0.020603 | 0.020633 |
| 8621 | 1160 | 1 | 0.018274 | 0.018286 | 0.018339 | 0.018306 | 0.018049 | 0.018386 | 0.018352 |
| 8576 | 1166 | 1 | 0.01793 | 0.018054 | 0.018108 | 0.017858 | 0.018142 | 0.01814 | 0.01802 |
| 8565 | 1167.5 | 1 | 0.018035 | 0.018177 | 0.018257 | 0.017927 | 0.018321 | 0.018248 | 0.018134 |
| 8525 | 1173 | 1 | 0.018845 | 0.01903 | 0.019164 | 0.018622 | 0.019256 | 0.019091 | 0.019015 |
| 8496 | 1177 | 1 | 0.020612 | 0.020832 | 0.020937 | 0.020371 | 0.021058 | 0.02094 | 0.020854 |
| 8446 | 1184 | 1 | 0.0274 | 0.027769 | 0.027682 | 0.027136 | 0.028172 | 0.028072 | 0.027781 |
| 8418 | 1188 | 1 | 0.031615 | 0.032149 | 0.031906 | 0.031481 | 0.032626 | 0.032571 | 0.032159 |
| 8389 | 1192 | 1 | 0.033492 | 0.034102 | 0.033845 | 0.033563 | 0.034457 | 0.034442 | 0.034203 |
| 8347 | 1198 | 1 | 0.031083 | 0031498 | 0.031409 | 0.031279 | 0.031529 | 0.031487 | 0.031786 |
| 8326 | 1201 | 1 | 0.028905 | 0.029171 | 0.029085 | 0.02908 | 0.029138 | 0.028993 | 0.02956 |
| 8313 | 1203 | 1 | 0.027531 | 0.027733 | 0.027583 | 0.027724 | 0.027708 | 0.027492 | 0.02816 |
| 8285 | 1207 | 1 | 0.024969 | 0.0251 | 0.02483 | 0.025172 | 0.025132 | 0.024829 | 0.025537 |
| 8264 | 1210 | 1 | 0.022844 | 0022933 | 0.022677 | 0.022977 | 0.023009 | 0.02266 | 0.023343 |
| 8203 | 1219 | 1 | 0.015306 | 0.015327 | 0.015374 | 0.015223 | 0.015542 | 0.015009 | 0.015488 |
| λ (cm −1) | λ (nm) | | | | | | | | |
| 8140 | 1228.5 | 1 | 0.00894 | 0.0089636 | 0.009101 | 0.008868 | 0.009078 | 0.008757 | 0.009014 |
| 8065 | 1240 | 1 | 0.004327 | 0.0043406 | 0.004467 | 0.00427 | 0.004393 | 0.00421 | 0.004363 |
| 7758 | 1289 | 1 | 0.000897 | 0.0009398 | 0.000895 | 0.00094 | 0.000918 | 0.001025 | 0.000921 |
| 8117 | 1232 | 1 | 0.005349 | 0.0053616 | 0.005304 | 0.005591 | 0.005209 | 0.005491 | 0.005213 |
| 7424 | 1347 | 1 | 0.00869 | 0.008592 | 0.008554 | 0.008798 | 0.008447 | 0.008701 | 0.00846 |
| 7396 | 1352 | 1 | 0.012209 | 0.012095 | 0.012056 | 0.012119 | 0.01192 | 0.012289 | 0.012093 |
| 7380 | 1355 | 1 | 0.015806 | 0.015784 | 0.015674 | 0.015614 | 0.015688 | 0.016136 | 0.01581 |
| 7356 | 1359.5 | 1 | 0.022613 | 0.022831 | 0.022633 | 0.022499 | 0.022915 | 0.023452 | 0.022656 |
| 7348 | 1361 | 1 | 0.024681 | 0.024929 | 0.024753 | 0.024623 | 0.025033 | 0.025538 | 0.024698 |
| 7339 | 1362.5 | 1 | 0.026435 | 0.026707 | 0.026552 | 0.026428 | 0.026818 | 0.027301 | 0.026438 |
| 7321 | 1366 | 1 | 0.029615 | 0.029773 | 0.02975 | 0.02954 | 0.029849 | 0030217 | 0.029509 |
| 7273 | 1375 | 1 | 0.038104 | 0.038252 | 0.038215 | 0.037747 | 0.038738 | 0.038781 | 0.037777 |
| 7254 | 1378.5 | 1 | 0.042097 | 0.042361 | 0.042333 | 0.041789 | 0.042904 | 0.04293 | 0.041847 |
| 7241 | 1381 | 1 | 0.044261 | 0.044511 | 0.044521 | 0.043951 | 0.044955 | 0.045039 | 0.044087 |

TABLE 8.1-continued

On line Determination of properties of feed to hydrogenation unit for gasoline

| | | Weight | Feed 8F | | 8A | 8B | 8C | 8D | 8E |
|---|---|---|---|---|---|---|---|---|---|
| | Prox. Index | | Measured | Estimated 0.0000042 | 0.0000034 | 0.0000047 | 0.0000114 | 0.0000130 | 0.0000222 |
| 7231 | 1383 | 1 | 0.04541 | 0.045556 | 0.045625 | 0.045014 | 0.045882 | 0.045992 | 0.045269 |
| 7199 | 1389 | 1 | 0.04833 | 0.048276 | 0.048333 | 0.04766 | 0.048684 | 0.04862 | 0.048084 |
| 7184 | 1392 | 1 | 0.049461 | 0.049347 | 0.049442 | 0.048812 | 0.049816 | 0.049597 | 0.04907 |
| 7161 | 1396.5 | 1 | 0.049514 | 0.049304 | 0.049526 | 0.049149 | 0.049522 | 0.049216 | 0.049109 |
| 7151 | 1398.5 | 1 | 0.04893 | 0.046706 | 0.048937 | 0.048708 | 0.048735 | 0.048454 | 0.048697 |
| 7117 | 1405 | 1 | 0.0471 | 0.04703 | 0.047083 | 0.046965 | 0.046646 | 0.046455 | 0.048003 |
| 7105 | 1407.5 | 1 | 0.046793 | 0.046839 | 0.046789 | 0.046579 | 0.046484 | 0.046242 | 0.0481 |
| 7087 | 1411 | 1 | 0.045855 | 0.046047 | 0.045894 | 0.045586 | 0.045829 | 0.045454 | 0.047474 |
| λ (cm −1) | λ (nm) | | | | | | | | |
| 7070 | 1414.5 | 1 | 0.043481 | 0.043682 | 0.043573 | 0.04322 | 0.043476 | 0.043002 | 0.045138 |
| 7018 | 1425 | 1 | 0.036493 | 0.036481 | 0.036252 | 0.036396 | 0.036261 | 0.035933 | 0.037564 |
| 6991 | 1430.5 | 1 | 0.037461 | 0.037372 | 0.037024 | 0.0375 | 0.037441 | 0.03717 | 0.037724 |
| 6974 | 1434 | 1 | 0.037514 | 0.037391 | 0.037162 | 0.037605 | 0.03762 | 0.037269 | 0.037298 |
| 6971 | 1434.5 | 1 | 0.037387 | 0.037261 | 0.03706 | 0.037486 | 0.037496 | 0.037135 | 0.037127 |
| 6930 | 1443 | 1 | 0.032307 | 0.032112 | 0.032218 | 0.032451 | 0.032217 | 0.031884 | 0.03179 |
| 6849 | 1460 | 1 | 0.022126 | 0.021897 | 0.022177 | 0.022295 | 0.021806 | 0.021642 | 0.021565 |
| 6824 | 1465.5 | 1 | 0.021591 | 0.021377 | 0.021682 | 0.021745 | 0.02138 | 0.021154 | 0.020925 |
| 6752 | 1481 | 1 | 0.018013 | 0.01796 | 0.018203 | 0.018411 | 0.017735 | 0.017774 | 0.017678 |
| 6720 | 1488 | 1 | 0.016098 | 0.016058 | 0.016257 | 0.016607 | 0.015759 | 0.015855 | 0.015811 |
| 6693 | 1494 | 1 | 0.014581 | 0.014542 | 0.014741 | 0.015042 | 0.01436 | 0.01435 | 0.014215 |
| 6614 | 1512 | 1 | 0.010568 | 0.01045 | 0.010546 | 0.011075 | 0.010321 | 0.010193 | 0.010114 |
| 6566 | 1523 | 1 | 0.007881 | 0.007794 | 0.007827 | 0.008432 | 0.007533 | 0.007562 | 0.007616 |
| 6536 | 1530 | 1 | 0.007116 | 0.007114 | 0.00711 | 0.007727 | 0.006783 | 0.006993 | 0.006957 |
| 6481 | 1543 | 1 | 0.005233 | 0.0052664 | 0.005299 | 0.005895 | 0.004821 | 0.005154 | 0.005163 |
| | | | | Estimated | | | | | |
| % Linear Saturated | | | 8.73 | 8.96 | 7.73 | 7.98 | 10.65 | 8.86 | 9.59 |
| % Isoparaffins | | | 6.83 | 7.35 | 6.51 | 6.62 | 8.8 | 8.26 | 6.56 |
| % Naphthenes | | | 5.83 | 5.73 | 6.38 | 6.93 | 5.56 | 4.87 | 4.95 |
| % Linear Olefins | | | 11.33 | 11.92 | 12.41 | 12.09 | 10.49 | 11.33 | 13.28 |
| % Cyclic Olefins | | | 12.79 | 12.77 | 12.99 | 13.68 | 12.94 | 11.81 | 12.44 |
| % Benzene | | | 22.46 | 21.74 | 21.35 | 21.38 | 23.34 | 21.53 | 21.1 |
| % Toluene | | | 13.72 | 13.63 | 13.71 | 13.51 | 13.55 | 13.18 | 14.18 |
| % Xylene | | | 5.08 | 6.74 | 5.97 | 5.57 | 4.89 | 11.36 | 5.9 |
| % Alkyl benzene | | | 5.96 | 5.94 | 5.98 | 5.6 | 5.11 | 6.84 | 6.16 |
| % Dienes | | | 16.44 | 15.90 | 17.67 | 17.94 | 14.83 | 13.57 | 15.47 |
| DENSITY | | | 0.8124 | 0.8066 | 0.8133 | 0.8097 | 0.8012 | 0.803 | 0.8058 |
| Yield light cut | | | 25.7 | 26.7 | 24.6 | 25.1 | 28.5 | 27.5 | 27.8 |
| Yield heavy cut | | | 40.3 | 39.4 | 41.7 | 41.2 | 35.7 | 39.7 | 38.7 |
| Yield raffinate | | | 13.7 | 13.3 | 13.5 | 13.4 | 13.7 | 12.4 | 13.5 |
| Yield benzene | | | 20.3 | 20.6 | 20.2 | 20.3 | 22.1 | 20.4 | 20.0 |

TABLE 9.1

Determination of MON of a reformate

| | | Weight | Reformate 9A | 9B | 9C | 9D | 9E | 9F |
|---|---|---|---|---|---|---|---|---|
| Proximity Index | | | Measured | Estimated 0.000058424 | 0.00006398 | 0.00006638 | 0.00018149 | 0.00018529 | 0.00019385 |
| λ (cm −1) | λ (nm) | | | | | | | |
| 4720 | 2119 | 1 | 0.0010981 | ?? | 0.0012043 | 0.0012359 | 0.00076051 | 0.0010861 | 0.00091553 |
| 4670 | 2141 | 1 | 0.017744 | ?? | 0.018971 | 0.01653 | 0.014737 | 0.01558 | 0.015581 |
| 4640 | 2155 | 1 | 0.018144 | ?? | 0.019076 | 0.016358 | 0.014281 | 0.0159 | 0.015344 |
| 4615 | 2167 | 1 | 0.024297 | ?? | 0.025324 | 0.021903 | 0.019435 | 0.023414 | 0.021006 |
| 4585 | 2181 | 1 | 0.020515 | ?? | 0.020612 | 0.017869 | 0.016021 | 0.016114 | 0.016429 |
| 4485 | 2230 | 1 | 0.012619 | ?? | 0.011885 | 0.011415 | 0.010242 | 0.01136 | 0.010529 |
| 4460 | 2242 | 1 | 0.018197 | ?? | 0.017086 | 0.016221 | 0.015362 | 0.016719 | 0.015344 |
| 4385 | 2281 | 1 | 0.092064 | ?? | 0.089813 | 0.090082 | 0.09165 | 0.094457 | 0.088586 |
| 4332 | 2308 | 1 | 0.12886 | ?? | 0.12812 | 0.13172 | 0.12815 | 0.1269 | 0.13463 |
| 4305 | 2323 | 1 | 0.11882 | ?? | 0.11606 | 0.11689 | 0.1205 | 0.12271 | 0.11448 |
| 4260 | 2347 | 1 | 0.098322 | ?? | 0.09716 | 0.10023 | 0.099018 | 0.09946 | 0.10223 |
| 4210 | 2375 | 1 | 0.064577 | ?? | 0.063284 | 0.065124 | 0.066654 | 0.065915 | 0.06736 |
| 4170 | 2398 | 1 | 0.061405 | ?? | 0.060439 | 0.063425 | 0.067026 | 0.065132 | 0.065986 |
| 4135 | 2418 | 1 | 0.059296 | ?? | 0.058485 | 0.061794 | 0.065184 | 0.063244 | 0.06268 |
| 4105 | 2436 | 1 | 0.06198 | ?? | 0.061975 | 0.064438 | 0.066333 | 0.062871 | 0.066088 |

TABLE 9.1-continued

Determination of MON of a reformate

| | Weight | | Reformate 9A | 9B | 9C | 9D | 9E | 9F |
|---|---|---|---|---|---|---|---|---|
| | | Measured | Estimated | | | | | |
| Proximity Index | | | 0.000058424 | 0.00006398 | 0.00006638 | 0.00018149 | 0.00018529 | 0.00019385 |
| 4060 | 2463 | 1 | 0.11037 | ?? | 0.11622 | 0.1131 | 0.11289 | 0.10222 | 0.1122 |
| 4040 | 2475 | 1 | 0.091698 | ?? | 0.094281 | 0.091661 | 0.091751 | 0.096914 | 0.090604 |
| MON | | 0 | 88 | ?? | 88.3 | 86.2 | 87.2 | 89.2 | 82.4 |

TABLE 9.2

"Sample" MC1 obtained by densification

| | | MC1 | 9B | 9D | 9G |
|---|---|---|---|---|---|
| Fraction in Mixture | | | 0.889 | −0.276 | 0.387 |
| λ (cm −1) | λ (nm) | | | | |
| 4720 | 2119 | 0.001175932 | 0.0012043 | 0.00076051 | 0.00081253 |
| 4670 | 2141 | 0.017365599 | 0.018971 | 0.014737 | 0.011765 |
| 4640 | 2155 | 0.017767782 | 0.019076 | 0.014281 | 0.012239 |
| 4615 | 2167 | 0.024118931 | 0.025324 | 0.019435 | 0.01796 |
| 4585 | 2181 | 0.019041012 | 0.020612 | 0.016021 | 0.013237 |
| 4485 | 2230 | 0.011987639 | 0.011885 | 0.010242 | 0.010952 |
| 4460 | 2242 | 0.017122848 | 0.017086 | 0.015362 | 0.015912 |
| 4385 | 2281 | 0.091829933 | 0.089813 | 0.09165 | 0.096098 |
| 4332 | 2308 | 0.1300549 | 0.12812 | 0.12815 | 0.13281 |
| 4305 | 2323 | 0.11911918 | 0.11606 | 0.1205 | 0.12682 |
| 4260 | 2347 | 0.09859607 | 0.09716 | 0.099018 | 0.10194 |
| 4210 | 2375 | 0.064520009 | 0.063284 | 0.066654 | 0.068709 |
| 4170 | 2398 | 0.061986802 | 0.060439 | 0.067026 | 0.068963 |
| 4135 | 2418 | 0.060186195 | 0.058485 | 0.065184 | 0.06749 |
| 4105 | 2436 | 0.062468569 | 0.061975 | 0.066333 | 0.066187 |
| 4060 | 2463 | 0.110237982 | 0.11622 | 0.11289 | 0.098096 |
| 4040 | 2475 | 0.093415832 | 0.094281 | 0.091751 | 0.090004 |
| MON00 | | 88.4 | 88.3 | 87.2 | 87.6 |

TABLE 9.3

"Sample" MC1 obtained by densification

| | | MC2 | 9B | 9C | 9D |
|---|---|---|---|---|---|
| Fraction in Mixture | | | 1.162 | 0.24 | −0.402 |
| λ (cm −1) | λ (nm) | | | | |
| 4720 | 2119 | 0.001178718 | 0.0012043 | 0.00035436 | 0.00076051 |
| 4670 | 2141 | 0.017275892 | 0.018971 | 0.0048161 | 0.014737 |
| 4640 | 2155 | 0.01792139 | 0.019076 | 0.0062335 | 0.014281 |
| 4615 | 2167 | 0.023747506 | 0.025324 | 0.0088912 | 0.019435 |
| 4585 | 2181 | 0.019544078 | 0.020612 | 0.0084724 | 0.016021 |
| 4485 | 2230 | 0.011946806 | 0.011885 | 0.0093905 | 0.010242 |
| 4460 | 2242 | 0.017153608 | 0.017086 | 0.01448 | 0.015362 |
| 4385 | 2281 | 0.091428926 | 0.089813 | 0.099623 | 0.09165 |
| 4332 | 2308 | 0.13153274 | 0.12812 | 0.14239 | 0.12815 |
| 4305 | 2323 | 0.11829752 | 0.11606 | 0.13282 | 0.1205 |
| 4260 | 2347 | 0.098798684 | 0.09716 | 0.1071 | 0.099018 |
| 4210 | 2375 | 0.06434942 | 0.063284 | 0.073368 | 0.066654 |
| 4170 | 2398 | 0.061427506 | 0.060439 | 0.075591 | 0.067026 |
| 4135 | 2418 | 0.059908962 | 0.058485 | 0.075639 | 0.065184 |
| 4105 | 2436 | 0.062810524 | 0.061975 | 0.072756 | 0.066333 |
| 4060 | 2463 | 0.11139522 | 0.11622 | 0.090539 | 0.11289 |
| 4040 | 2475 | 0.09128022 | 0.094281 | 0.07754 | 0.091751 |
| MON00 | | 88.2 | 88.3 | 86 | 87.2 |

TABLE 9.5

Recognition of new sample by auto adjustment

|  | Weight | Measured | Estimated | 9A |
|---|---|---|---|---|
| Proximity Index |  |  | 0.000012235 | 0.000012235 |
| λ (cm −1) | λ (nm) |  |  |  |
| 4720 | 2119 | 1 | 0.0010702 | 0.0010981 | 0.0010981 |
| 4670 | 2141 | 1 | 0.0171 | 0.017744 | 0.017744 |
| 4640 | 2155 | 1 | 0.017768 | 0.018144 | 0.018144 |
| 4615 | 2167 | 1 | 0.024103 | 0.024297 | 0.024297 |
| 4585 | 2181 | 1 | 0.020269 | 0.020515 | 0.020515 |
| 4485 | 2230 | 1 | 0.012224 | 0.012619 | 0.012619 |
| 4460 | 2242 | 1 | 0.018338 | 0.018197 | 0.018197 |
| 4385 | 2281 | 1 | 0.091998 | 0.092064 | 0.092064 |
| 4332 | 2308 | 1 | 0.1306 | 0.12886 | 0.12886 |
| 4305 | 2323 | 1 | 0.11841 | 0.11882 | 0.11882 |
| 4260 | 2347 | 1 | 0.098802 | 0.098322 | 0.098322 |
| 4210 | 2375 | 1 | 0.06262 | 0.064577 | 0.064577 |
| 4170 | 2398 | 1 | 0.060234 | 0.061405 | 0.061405 |
| 4135 | 2418 | 1 | 0.059762 | 0.059296 | 0.059296 |
| 4105 | 2436 | 1 | 0062527 | 0.06198 | 0.06198 |
| 4060 | 2463 | 1 | 0.11151 | 0.11037 | 0.11037 |
| 4040 | 2475 | 1 | 0.092677 | 0.091698 | 0.091698 |
| MON00 |  |  | 87.9 | 88 | 88 |

EXAMPLE 10

On line Determination of the Properties of Polybutenes in a Polyisobutene Plant.

It is desired to control the properties of polybutenes made during their manufacture in order to adapt immediately the operating conditions to any changes in any product.

They were made by polymerisation of isobutene with an Bronsted acid catalyst to form a crude product from which distillation removes gaseous hydrocarbons and light polymeric products, and leaves heavy polyisobutene.

During the manufacture, the absorbances of heavy polyisobutene (Ref 10A) were measured with an NIR spectrometer in the wavelength region 6000–8850 $cm^{-1}$. The spectrometer had been installed on line in a plant with the aid of a fast side loop situated in the line carrying the heavy polymer remaining after the distillation. An analyser attached to the spectrometer sent within 2 minutes to the controller of the plant a measure of the properties which had been obtained on the basis of the NIR spectrum measured on the above products and estimated using the method of the invention as follows.

The method chosen to treat the NIR spectrum involved a discrete selection of wavelengths chosen on the basis of chemical and/or statistical criteria, the chosen wavelength being between 6079 and 8803 $cm,^{-1}$. The absorbances were normalised according to procedure (2).

For a series of standard polyisobutene products, for which the NIR spectra were known, the Minimum Proximity Index was obtained by the method above to be $5 \times 10^{-6}$, this Index was not weighted. The proximity indices, between the absorbances of the standards in the bank and those of the unknown from the plant (normalised as above) were calculated and 5 standards 10B–10F were found with proximity indices<Min. Prox. Index.

By averaging the values of each property of those 5 standards it was possible to calculate the corresponding properties sought for the unknown for controlling the plant from knowing the viscosity at 100° C., the number average molecular weight (MN), size of the distribution of molecular weights obtained by gel permeation chromatography (called LGPC) as well as the content of butene-1 (BUT-1).

Other properties may also be determined such as density or inflammability point in a similar way.

Table 10.1 shows the results, from which it is clear that the calculated properties (in col 5) were all in agreement with those measured on the unknown by standard methods and were within the limits of reproducibility of those methods for use in the polyisobutene area (on the basis of a 95% probability in any measurement) namely 0.7% for viscosity (ASTM D445), 8.5° C. for inflammability point (ASTM D93-80), 5% for number average Molecular Weight and 3% for Molecular Weight distribution (both by Gel Permeation Chromatography), 10% for unsaturation (NMR) and for butene-1 (IR) and 1% for maleinisation index.

EXAMPLE 11

Determination of Properties of Low Molecular Weight Polyisobutene

The properties of a low molecular weight polyisobutene (11A) were determined in order to control its manufacturing unit as in Example 10. The method adopted was as in Example 10 with the absorbances of the polyisobutene measured as before in the 6000–8850 $cm^{-1}$ wavelength range with the aid of the NIR spectrometer installed on the residue line from the distillation unit.

The properties for determination were the viscosity at 100° C., the number average molecular weight, the LGPC (as in Ex. 10), the content of butene-1, the inflammability point (IP) and the degree of unsaturation expressed in groups/liter, and the maleinisation index (PlBSA). The unsaturations were of the types VIN, TRII, TRI2, TRI2cis, TRl2trans, TRlTotal and TETRA as defined above. The maleinisation index is particularly important for control of plants to make polyisobutenes as it is of great value to purchasers of low polyisobutenes.

The NIR spectra of a series of standard polyisobutenes whose properties were measured by reference techniques, were determined and from the bank obtained the Minimal Index was determined at $9 \times 10^{-5}$, via the unweighted proximity indices. The density of standards in the Bank was sufficiently high for there to be 5 standards 11B–11F inside the sphere with proximity indices with respect to the unknown less than the Minimal Index. By averaging the data from these standards, the properties of the unknown were determined. The results are shown in Table 11.1. Here also the properties of the polyisobutene from the plant calculated from the standards were all within the limits of reproducibility of the standard methods. Thus continuously and with total reliability, the quality of product from the plant can thus be obtained and can be maintained taking account of the process dynamics.

Other properties of the low molecular weight polyisobutene may be obtained in a similar way.

EXAMPLE 12

Determination of the Properties of a Polyethylene to Control its Manufacture

Ethylene was polymerised with a chromium catalyst in a plant to produce polyethylene, whose properties of density and fluidity index/Melt Index (measured according to the IF2 standard method) (called grade) were to control its market specification. The product 12A, in the form of a powder, required rapid measurement of these properties to correct the plant operating conditions to ensure manufacture of a polymer of constant quality.

The NIR spectra of a series of standard polyethylenes were determined by means of a Fourier Transform NIR spectrometer in the 5500–8400 $cm^{-1}$ region, as well as their densities and fluidity indices to obtain a bank of standards. The absorbances of the spectra were normalised as described above, to ensure better known numerical stability for the data. The Minimal Proximity Index was calculated from the unweighted proximity indices of the standards (according to Eq. 2) and by means of the technique of Eq. 8 in which v was 1.1, the proximity index to the product 12A was chosen to 0.025.

The proximity indices between the unknown polyethylenes 12A from the plant and the standards were calculated according to Eq. 2, and three standards 12B, 12C and 12D were found with small enough proximity indices. From the properties of these standards 12B–D by averaging, the properties of the unknown product 12A were obtained in less than 1 minute, allowing immediate reaction to all variations in the production operation. The results are shown in Table 12.1, and are in perfect agreement with the properties determined by reference methods, and within their reproducibilities, namely 1% for density and 14% for grade.

The method may be applied in the same way to the determination of other properties, for example percentage of comonomer in an ethylene copolymerisation, the degree of conversion of the reaction or the content of volatiles, as well as to other types of polymerisations to polyethylene such as ones with Ziegler Natta catalysts.

EXAMPLE 13
Control of Polyisobutene Production

Figure 3:
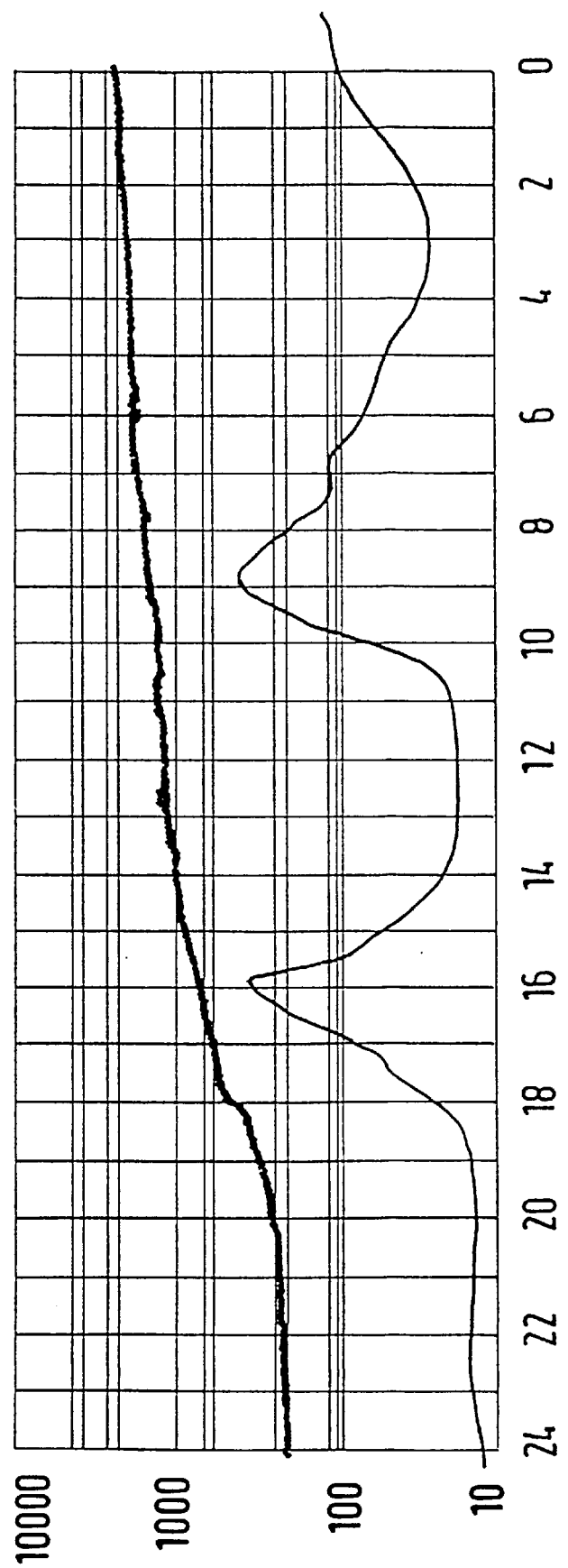

Polyisobutene production was monitored as described in Example 11 over a period of 24 hrs with a read out throughout of the calculated viscosity of the product heavy polymer. FIG. 3 shows this read out from the computer analysing the NIR data with viscosity expressed in centistokes as ordinate and time in hours as abcissa reading from right to left; together with a copy of the spectrum (with linear ordinate range from 0–0.5 absorbance unit and 950 to 1650 nm abcissa measuring from left to right) of the product at the start of the 24 hr period when its properties were as follows: viscosity 2538 cps, Flash Pt 197° C., Mn 2267, Mol Wt Distrib. 1.93, % vinylidene 3.364, TRITOT 60.03, TRI2c 12.63, TRI2t 36.69% butene-1 2.65. Over this 24 hr period the viscosity changed significantly. The calculations to enable this to be followed continuously were possible by the method of this invention involving the remarkable property of the process of "automatic densification" and autoadjustment of the standards, with avoidance of the recalibrations and fastidious and uncertain remodellings of regressional methods. This aspect of the present method is described further below.

For many process operations involving on line analysis of product leaving the reactor, there may be only a few standards involving NIR absorbances on these products of known analysis or properties.

For a polyisobutene pilot plant, the absorbances of the standards for the products, were measured with an FTIR spectrometer between 6400–9000 $cm^{-1}$ and the properties were the percentages of constituents leaving the reactor as measured by distillation (i.e. the heavy and light fractions); these parameters were measured because they represent the most interesting to follow for the progress of the reaction, though others could also be used as well or instead if desired. The Minimal Index was calculated from the proximity indices of the standards (according to Eq. 3) weighted here by the accuracy factor in absorptions at each wavelength chosen; the proximity index as with respect to the unknown was fixed by Procedure 3 at $3 \times 10^{-3}$. Because of the low population of standards in the band with proximity indices with respect to an unknown polyisobutene 13A from the unit within this level, no standards were found and hence no values can be directly estimated for the properties (shown as a question mark in col. 5 of Table 13.1 hereafter with the rest of the absorbances of the unknown and those of 3 nearby standards 13B, 13C and 13D.

The densification process of procedure 2 was thus invoked in order to increase the bank of known standards. Tables 13.2 and 13.3 (in col. 3) show the results obtained for "standards" MC1 and MC2 respectively determined by calculation and located with small enough proximity indices of process Eq. 3. Col. 4 and later columns give the absorbances and properties of the existing standards of the bank used to generate novel "standards" namely 13B, 13C and 13E (for MC1) and 13B, 13D and 13E (for MC2). Col 2 gives for each of the novel standards the fraction from the known standards used in the mixture to generate the new ones. This fraction can be negative or positive but can be applied as in Eq. 4.

Based on the new "standards" MC1 and MC2 (with Proximity Indices with respect to the unknown of $2.7 \times 10^{-3}$ and $2.6 \times 10^{-3}$ respectively), the properties of the unknown 13A were then calculated, by use of arithmetic averaging with results as shown in Table 13.4. The weight percentage of the 2 polymeric components in product 13A were well compatible with the measured values from the distillation in the light of the errors in the reproducibility of the latter.

The above process enables immediate auto adjustment of the bank by automatic incorporation of the novel "standards" as though they were originally measured ones. Thus property is remarkable as it enables determination of properties of products hitherto unknown in the bank and to gain precious time in the adjustment of operating conditions on the plant to take account of changes.

This autoadjustment process was used in a process whose results were as given in Table 13.5 below, which shows that the novel "standard" measured immediately after incorporation of the "standard" unrecognised in the bank is now recognised and can be used to calculate well all the properties and without any modification nor intervention from existing models. This operation is better than that of classical regressional models, which are incapable of predicting the properties of samples not included in the trial area or of predicting them with a non acceptable error; these regression techniques would require for use the preparation of new models for each property and without guarantee of success and the production unit using the new model would be operating blind during the recalibration period.

EXAMPLE 14
Determination of the Properties of a Polyethylene Glycol

A polyalkoxylenated product had been made discontinuously by polymerisation in the liquid phase of one or more epoxides specifically ethylene oxide with an organic compound possessing at least one active hydrogen atom, such as an alcohol specifically butanol. The values of the properties of the product during the process had hitherto been regularly evaluated in the laboratory by standard methods during the production in order to determine the necessary amounts of epoxide. However, the times to obtain the analytical results were generally prohibitive in terms of the amounts of epoxide consumed and quality of product obtained during non optimum operations.

The method of the present invention was applied to this process. A band of standards for polyethylenoxylated butanols covering the field between low ones (Mol. Wt about 200) up to high ones (Mol. Wt. of the order of 9000) was generated incorporating the properties of a number of these compounds as well as their spectra, determined in the 4000–8400 $cm^{-1}$ wavelength region with an FT NIR spectrometer. The properties considered were the hydroxyl index (fundamental for the conduct/progress of the reaction) as well as the viscosity measured at 100° C. and the molecular weight.

The bank of data was applied by the method of the invention to the production of a polyethylenoxylated butanol of Molecular Weight of about 8000 (PEG 8000). From the standards with spectra normalised per Eq. 3 the Minimal Index was calculated at $1.2 \times 10^{-4}$. The Proximity Indices between the unknown PEG 8000 and the standards were calculated (using Eq. 2) and four standards 14A, 14B, 14C and 14D were found with Proximity Index values less than Minimal Index. From the properties of these standards, the properties of the unknown PEG 8000 were calculated by averaging with (as shown in Table 14.1) excellent results for all which were obtained in less than 1 minute, enabling maintenance or immediate correction of the level of ethylene oxide used in order to maintain the final quality of the products. Furthermore the differences obtained between the results obtained by the above calculations and by standard methods were all inside the limits of reproducibility of those reference methods, namely 0.7% for the viscosity (by ASTM D445) and 5.8% and 3.6% respectively for the hydroxyl index below and above 100 (ASTM D4274). The Molecular Weight was obtained directly from the hydroxyl index with the same reproducibility values.

Other properties of the polyethylene oxylated butanol may be obtained in a similar way.

TABLE 10

On line Determination of the Properties of a High MW Polyisobutene

| | | Wt | 10A | | 10B | 10C | 10D | 10E | 10F |
|---|---|---|---|---|---|---|---|---|---|
| | Prox. Index | | Measured | Estimated | 2.28E-07 | 2.41E-07 | 3.17E-07 | 4.99E-07 | 5.05E-07 |
| Wavelength | | | | | | | | | |
| $\lambda$ (cm −1) | $\lambda$ (nm) | | | | | | | | |
| 6079 | 1645 | 1 | 0.034526 | 0.0345348 | 0.03445 | 0.034579 | 0.034566 | 0.034566 | 0.034513 |
| 6109 | 1637 | 1 | 0.033387 | 0.0334816 | 0.033343 | 0.033452 | 0.033511 | 0.033514 | 0.033588 |
| 6165 | 1622 | 1 | 0.031521 | 0.0316246 | 0.031567 | 0.031568 | 0.031642 | 0.031691 | 0.031655 |
| 6200 | 1613 | 1 | 0.029482 | 0.0295274 | 0.029529 | 0.029419 | 0.029577 | 0.029578 | 0.029534 |
| 6215 | 1609 | 1 | 0.028092 | 0.0281402 | 0.028072 | 0.028047 | 0.028148 | 0.028212 | 0.028222 |
| 6262 | 1597 | 1 | 0.022757 | 0.0227916 | 0.022708 | 0.02274 | 0.02287 | 0.022827 | 0.022813 |
| 6418 | 1558 | 1 | 0.009918 | 0.0099332 | 0.009884 | 0.009823 | 0.010043 | 0.009945 | 0.009971 |
| 6532 | 1531 | 1 | 0.008198 | 0.0082184 | 0.008228 | 0.008124 | 0.008355 | 0.008288 | 0.008097 |
| 6649 | 1504 | 1 | 0.013928 | 0.0139594 | 0.013956 | 0.013878 | 0.01398 | 0.014021 | 0.013962 |
| 6698 | 1493 | 1 | 0.018189 | 0.0181368 | 0.018174 | 0.018078 | 0.018188 | 0.018186 | 0.018058 |
| 6821 | 1466 | 1 | 0.023312 | 0.0233096 | 0.023296 | 0.023313 | 0.02329 | 0.02332 | 0.023329 |
| 6901 | 1449 | 1 | 0.03066 | 0.03061 | 0.030665 | 0.030627 | 0.030622 | 0.03062 | 0.030516 |
| 6925 | 1444 | 1 | 0.032947 | 0.0329416 | 0.032984 | 0.032945 | 0.032842 | 0.032927 | 0.03301 |
| 6964 | 1436 | 1 | 0.034095 | 0.0340834 | 0.034175 | 0.034129 | 0.03404 | 0.034121 | 0.033952 |
| 6998 | 1429 | 1 | 0.033036 | 0.0330732 | 0.033113 | 0.033051 | 0.033061 | 0.033057 | 0.033084 |
| 7052 | 1418 | 1 | 0.037285 | 0.0373202 | 0.037367 | 0.037376 | 0.03725 | 0.037374 | 0.037234 |
| 7062 | 1416 | 1 | 0.038945 | 0.0389808 | 0.039025 | 0.039019 | 0.038891 | 0.038957 | 0.039012 |
| 7092 | 1410 | 1 | 0.042821 | 0.0429034 | 0.042882 | 0.042993 | 0.042821 | 0.042866 | 0.042955 |
| 7148 | 1399 | 1 | 0.050224 | 0.0501864 | 0.050162 | 0.050204 | 0.05023 | 0.050197 | 0.050139 |
| 7158 | 1397 | 1 | 0.05171 | 0.0516546 | 0.051583 | 0.051672 | 0.051573 | 0.051668 | 0.051777 |
| 7199 | 1389 | 1 | 0.055328 | 0.0552568 | 0.055321 | 0.055251 | 0.055274 | 0.055195 | 0.055243 |
| 7220 | 1385 | 1 | 0.055837 | 0.055829 | 0.55823 | 0.055857 | 0.055805 | 0.055755 | 0.055905 |
| 7231 | 1383 | 1 | 0.05578 | 0.0557724 | 0.055758 | 0.055782 | 0.055802 | 0.055606 | 0.055914 |
| 7262 | 1377 | 1 | 0.053775 | 0.053733 | 0.053785 | 0.053713 | 0.0538 | 0.053595 | 0.053772 |
| 7294 | 1371 | 1 | 0.048604 | 0.0484784 | 0.048495 | 0.048516 | 0.048501 | 0.048403 | 0.048477 |
| 7331 | 1364 | 1 | 0.040558 | 0.0405078 | 0.040492 | 0.040581 | 0.040499 | 0.040494 | 0.040473 |
| 7348 | 1361 | 1 | 0.036912 | 0.0368442 | 0.036891 | 0.036937 | 0.036791 | 0.036849 | 0.036753 |
| 7375 | 1356 | 1 | 0.028832 | 0.028823 | 0.028885 | 0.028916 | 0.028736 | 0.028825 | 0.028753 |
| 7402 | 1351 | 1 | 0.01934 | 0.0193446 | 0.019389 | 0.019411 | 0.019293 | 0.019343 | 0.019287 |
| 7899 | 1266 | 1 | 0.002143 | 0.0020506 | 0.002127 | 0.002037 | 0.002131 | 0.002039 | 0.001919 |
| 8000 | 1250 | 1 | 0.006563 | 0.00066608 | 0.00675 | 0.006643 | 0.006601 | 0.006705 | 0.006605 |
| 8097 | 1235 | 1 | 0.017014 | 0.0170314 | 0.016928 | 0.017022 | 0.01693 | 0.017118 | 0.017159 |
| 8197 | 1220 | 1 | 0.033957 | 0.033925 | 0.033887 | 0.033884 | 0.033837 | 0.034041 | 0.033976 |
| 8217 | 1217 | 1 | 0.037243 | 0.0373344 | 0.037337 | 0.037276 | 0.037258 | 0.037459 | 0.037342 |
| 8251 | 1212 | 1 | 0.043473 | 0.043491 | 0.043447 | 0.043397 | 0.043469 | 0.043609 | 0.043533 |
| 8278 | 1208 | 1 | 0.048882 | 0.0488738 | 0.048886 | 0.048835 | 0.048753 | 0.049003 | 0.048892 |
| 8333 | 1200 | 1 | 0.080806 | 0.080871 | 0.080945 | 0.080719 | 0.080878 | 0.080894 | 0.080919 |
| 8361 | 1196 | 1 | 0.0924 | 0.0924876 | 0.092499 | 0.092582 | 0.092447 | 0.092511 | 0.092399 |
| 8375 | 1194 | 1 | 0.091802 | 0.0918924 | 0.092499 | 0.091891 | 0.091957 | 0.091803 | 0.091918 |
| 8382 | 1193 | 1 | 0.090957 | 0.090951 | 0.090973 | 0.090952 | 0.090913 | 0.090875 | 0.091042 |
| 8403 | 1190 | 1 | 0.088076 | 0.0879942 | 0.087981 | 0.088052 | 0.0881 | 0.087893 | 0.087945 |
| 8418 | 1188 | 1 | 0.086503 | 0.0865104 | 0.086496 | 0.086468 | 0.086638 | 0.086372 | 0.086578 |
| 8503 | 1176 | 1 | 0.068153 | 0.0681298 | 0.068144 | 0.068087 | 0.06819 | 0.068083 | 0.068145 |
| 8540 | 1171 | 1 | 0.058772 | 0.0587116 | 0.058757 | 0.058746 | 0.058828 | 0.058655 | 0.058572 |

TABLE 10-continued

On line Determination of the Properties of a High MW Polyisobutene

| | | Wt | 10A | | 10B | 10C | 10D | 10E | 10F |
|---|---|---|---|---|---|---|---|---|---|
| | Prox. Index | | Measured | Estimated | 2.28E-07 | 2.41E-07 | 3.17E-07 | 4.99E-07 | 5.05E-07 |
| 8598 | 1163 | 1 | 0.043961 | 0.0439804 | 0.043948 | 0.043992 | 0.043996 | 0.043947 | 0.044019 |
| 8658 | 1155 | 1 | 0.035651 | 000355848 | 0.035646 | 0.035571 | 0.03557 | 0.035569 | 0.035568 |
| 8703 | 1149 | 1 | 0.031642 | 0.0315346 | 0.03152 | 0.031638 | 0.031491 | 0.013545 | 0.031479 |
| 8726 | 1146 | 1 | 0.02824 | 0.028269 | 0.028194 | 0.02837 | 0.028297 | 0.028232 | 0.028252 |
| 8803 | 1136 | 1 | 0.013764 | 0.0137152 | 0.013641 | 0.013837 | 0.013715 | 0.013645 | 0.013738 |
| | VISCOSITY | | 4717 | 4708.2 | 4669 | 4783 | 5005 | 4484 | 4600 |
| | MN | | 2991 | 3031.4 | 3026 | 3016 | 3214 | 2930 | 2971 |
| | LGPC | | 1.81 | 1.812 | 1.80 | 1.82 | 1.78 | 1.84 | 1.82 |
| | BUT-1 | | 1.68 | 1.6298 | 1.62 | 1.4 | 1.669 | 1.66 | 1.8 |

In this Table 1.56E-07 means $1.56 \times 10^{-7}$

TABLE 11.1

On line Determination of the Properties of a Polyisobutene of Low Mol. Wt.

| | | Wt | 11A | | 11B | 11C | 11D | 11E | 11F |
|---|---|---|---|---|---|---|---|---|---|
| | Prox. Index | | Measured | Estimated 4.34E-07 | 2.28E-07 | 8.65E-07 | 9.18E-07 | 1.07E-06 | 1.68E-06 |

Wavelength

| $\lambda$ (cm −1) | $\lambda$ (nm) | | | | | | | | |
|---|---|---|---|---|---|---|---|---|---|
| 6079 | 1645 | 1 | 0.03487 | 0.0350224 | 0.034809 | 0.035165 | 0.034927 | 0.03502 | 0.035191 |
| 6109 | 1637 | 1 | 0.033505 | 0.0336706 | 0.033428 | 0.033829 | 0.033536 | 0.033725 | 0.033835 |
| 6165 | 1622 | 1 | 0.029642 | 0.0296054 | 0.029588 | 0.029806 | 0.029475 | 0.029625 | 0.029553 |
| 6200 | 1613 | 1 | 0.026851 | 0.02668 | 0.026667 | 0.026958 | 0.026525 | 0.026706 | 0.026544 |
| 6215 | 1609 | 1 | 0.025316 | 0.025199 | 0.025198 | 0.025414 | 0.025055 | 0.025241 | 0.025087 |
| 6262 | 1597 | 1 | 0.020251 | 0.0201638 | 0.020177 | 0.020325 | 0.020046 | 0.020202 | 0.020069 |
| 6418 | 1558 | 1 | 0.008942 | 0.00905 | 0.009014 | 0.009098 | 0.009048 | 0.009074 | 0.009016 |
| 6532 | 1531 | 1 | 0.007916 | 0.0080262 | 0.007969 | 0.008029 | 0.008046 | 0.008052 | 0.008035 |
| 6649 | 1504 | 1 | 0.014038 | 0.0141226 | 0.014057 | 0.014102 | 0.014121 | 0.014208 | 0.014125 |
| 6698 | 1493 | 1 | 0.01827 | 0.0183048 | 0.018253 | 0.01832 | 0.018273 | 0.018369 | 0.018309 |
| 6821 | 1466 | 1 | 0.023637 | 0.0236526 | 0.023648 | 0.023639 | 0.023669 | 0.023643 | 0.023665 |
| 6901 | 1449 | 1 | 0.030691 | 0.0307184 | 0.030767 | 0.030664 | 0.030755 | 0.030708 | 0.030698 |
| 6925 | 1444 | 1 | 0.033186 | 0.0331576 | 0.033188 | 0.033115 | 0.033189 | 0.033208 | 0.033088 |
| 6964 | 1436 | 1 | 0.035052 | 0.0350774 | 0 0351 | 0.034983 | 0.035168 | 0.035051 | 0.035085 |
| 6998 | 1429 | 1 | 0.034516 | 0.0345532 | 0.034541 | 0.034482 | 0.034606 | 0.0345 | 0.034637 |
| 7052 | 1418 | 1 | 0.039698 | 0.0396944 | 0.039673 | 0.039522 | 0.039765 | 0.039724 | 0.039788 |
| 7062 | 1416 | 1 | 0.041541 | 0.0415304 | 0.041504 | 0.041347 | 0.041604 | 0.041588 | 0.041609 |
| 7092 | 1410 | 1 | 0.045553 | 0.0455666 | 0.045523 | 0.045335 | 0.045654 | 0.045617 | 0.045714 |
| 7148 | 1399 | 1 | 0.052377 | 0.052487 | 0.052493 | 0.052322 | 0.052627 | 0.052425 | 0.052568 |
| 7158 | 1397 | 1 | 0.053934 | 0.0539828 | 0.05400S | 0.053795 | 0.054148 | 0.053874 | 0.054092 |
| 7199 | 1389 | 1 | 0.056865 | 0.0569614 | 0.05701 | 0.056767 | 0.057037 | 0.056838 | 0.057155 |
| 7220 | 1385 | 1 | 0.056997 | 0.056996 | 0.057043 | 0.056965 | 0.057052 | 0.056858 | 0.057062 |
| 7231 | 1383 | 1 | 0.056741 | 0.0566584 | 0.056674 | 0.056626 | 0.056695 | 0.056527 | 0.05677 |
| 7262 | 1377 | 1 | 0.053595 | 0.0535546 | 0.053611 | 0.053499 | 0.053576 | 0.053515 | 0.053572 |
| 7294 | 1371 | 1 | 0.047392 | 0.0473396 | 0.047407 | 0.047357 | 0.047322 | 0.047342 | 0.04727 |
| 7331 | 1364 | 1 | 0.039219 | 0.039141 | 0.039245 | 0.039188 | 0.039132 | 0.039186 | 0.038954 |
| 7348 | 1361 | 1 | 0.035369 | 0.0352522 | 0.035363 | 0.03534 | 0.035213 | 0.035285 | 0.03506 |
| 7375 | 1356 | 1 | 0.026707 | 0.026597 | 0.07671 | 0.026679 | 0.02654 | 0.02663 | 0.026426 |
| 7402 | 1351 | 1 | 0.017328 | 0.017232 | 0.017357 | 0.017328 | 0.017195 | 0.017258 | 0.017022 |
| 7899 | 1266 | 1 | 0.002464 | 0.0024364 | 0.06244 | 0.002455 | 0.002472 | 0.002381 | 0.002444 |
| 8000 | 1250 | 1 | 0.007208 | 0.007183 | 0.00719 | 0.00714 | 0.007244 | 0.007126 | 0.007215 |
| 8097 | 1235 | 1 | 0.017338 | 0.0172718 | 0.017276 | 0.01724 | 0.017281 | 0.017216 | 0.017346 |
| 8197 | 1220 | 1 | 0.035357 | 0.0352076 | 0.035245 | 0.035151 | 0.035316 | 0.034991 | 0.035336 |
| 8217 | 1217 | 1 | 0.039433 | 0.0393774 | 0.039449 | 0.039195 | 0.03959 | 0.039126 | 0.039527 |
| 8251 | 1212 | 1 | 0.047005 | 0.0468886 | 0.046848 | 0.046753 | 0.047075 | 0.046638 | 0.047129 |
| 8278 | 1206 | 1 | 0.05312 | 0.0530672 | 0.053062 | 0.052878 | 0.053291 | 0.052931 | 0.053174 |
| 8333 | 1200 | 1 | 0.081058 | 0.0809726 | 0.081013 | 0.080977 | 0.080954 | 0.081039 | 0.08088 |
| 8361 | 1196 | 1 | 0.093478 | 0.093531 | 0.093501 | 0.093565 | 0.093469 | 0.093651 | 0.093469 |
| 8375 | 1194 | 1 | 0.094014 | 0.0941538 | 0.094091 | 0.094159 | 0.09414 | 0.094226 | 0.094153 |
| 8382 | 1193 | 1 | 0.093212 | 0.09345 | 0.093337 | 0.093337 | 0.093457 | 0.093559 | 0.09356 |
| 8403 | 1190 | 1 | 0.08976 | 0.0899258 | 0.089806 | 0.039808 | 0.089953 | 0.089966 | 0.090096 |
| 8418 | 1188 | 1 | 0.08678 | 0.0869658 | 0.086901 | 0.086907 | 0.086959 | 0.087037 | 0.087125 |
| 8503 | 1176 | 1 | 0.06419 | 0.0641896 | 0.064217 | 6.064345 | 0.064015 | 0.064341 | 0.06403 |

TABLE 11.1-continued

On line Determination of the Properties of a Polyisobutene of Low Mol. Wt.

| | | Wt | 11A | | 11B | 11C | 11D | 11E | 11F |
|---|---|---|---|---|---|---|---|---|---|
| | Prox. Index | | Measured | Estimated 4.34E-07 | 2.28E-07 | 8.65E-07 | 9.18E-07 | 1.07E-06 | 1.68E-06 |
| Wavelength | | | | | | | | | |
| λ (cm −1) | λ (nm) | | | | | | | | |
| 8540 | 1171 | 1 | 0.054912 | 0.0548696 | 0.054942 | 0.055027 | 0.054736 | 0.055017 | 0.054626 |
| 8598 | 1163 | 1 | 0.040824 | 0.0408046 | 0.04087 | 0.040884 | 0.040724 | 0.040918 | 0.040627 |
| 8658 | 1155 | 1 | 0.03355 | 0.0335614 | 0.033553 | 0.033718 | 0.033461 | 0.033613 | 0.033462 |
| 8703 | 1149 | 1 | 0.029161 | 0.0291404 | 0.029156 | 0.029278 | 0.029022 | 0.029172 | 0.029074 |
| 8726 | 1146 | 1 | 0.025375 | 0.025314 | 0.025338 | 0.02541 | 0.025223 | 0.025394 | 0.025205 |
| 8803 | 1136 | 1 | 0.011761 | 0.0116668 | 0.011764 | 0.011772 | 0.011618 | 0.011658 | 0.011522 |
| | Viscosity | | 225 | 224.6 | 221 | 237 | 213 | 209 | 243 |
| | MN | | 946 | 923 | 926 | 930 | 914 | 902 | 943 |
| | LGPC | | 1.59 | 1.594 | 1.58 | 1.63 | 1.55 | 1.62 | 1.59 |
| | VIN | | 0.02 | 0.0216 | 0.017 | 0.025 | 0.018 | 0.021 | 0.027 |
| | TRI1 | | 0.012 | 0.0112 | 0.01 | 0.009 | 0.01 | 0.017 | 0.01 |
| | TRI2 | | 0.41 | 0.407 | 0.411 | 0.405 | 0.425 | 0.414 | 0.38 |
| | TRI2c | | 0.112 | 0.1156 | 0.115 | 0.111 | 0.121 | 0.121 | 0.11 |
| | TRI2t | | 0.298 | 0.2914 | 0.296 | 0.294 | 0.304 | 0.293 | 0.27 |
| | TRItot | | 0.578 | 0.5766 | 0.586 | 0.557 | 0.594 | 0.598 | 0.548 |
| | TETRA | | 0.163 | 0.1686 | 0.159 | 0.177 | 0.17 | 0.17 | 0.167 |
| | BUT-1 | | 7.0 | 7.3 | 7.2 | 7.2 | 7.5 | 7.13 | 7.47 |
| | Flash Point | | 171 | 170 | 170 | 172 | 168 | 165 | 175 |
| | PIBSA | | 99 | 99.2 | 99.5 | 98.6 | 98.4 | 99.3 | 100.1 |

TABLE 12.1

Determination of the Properties of a Polyethylene to Control its Manufacture

| | | Wt | 12A | | 12B | 12C | 12D | 12E | 12F |
|---|---|---|---|---|---|---|---|---|---|
| | Prox. Index | | Measured | Estimated 0.0042626 | 0.0072895 | 0.0095186 | 0.012812 | 0.017956 | 0.020326 |
| Wavelength | | | | | | | | | |
| λ (cm −1) | λ (nm) | | | | | | | | |
| 5520 | 1812 | 1 | 2.9479 | 2.96034 | 2.9491 | 2.9576 | 2.9467 | 2.99 | 2.9583 |
| 5532 | 1808 | 1 | 2.9677 | 2.98038 | 2.9708 | 2.978 | 2.9663 | 3.0081 | 2.9787 |
| 5544 | 1804 | 1 | 2.9663 | 2.97482 | 2.9668 | 2.9721 | 2.96 | 3.0018 | 2.9734 |
| 5556 | 1600 | 1 | 2.9003 | 2.90612 | 2.898 | 2.9034 | 2.891 | 2.9307 | 2.9075 |
| 5566 | 1796 | 1 | 2.7954 | 2.8019 | 2.7949 | 2.7996 | 2.7872 | 2.8221 | 2.8071 |
| 5580 | 1792 | 1 | 2.7574 | 2.76272 | 2.7576 | 2.7579 | 2.7484 | 2.7806 | 2.7691 |
| 5592 | 1768 | 1 | 2.8275 | 2.83096 | 2.827 | 2.8257 | 2.8166 | 2.848 | 2.8375 |
| 5604 | 1784 | 1 | 2.9641 | 2.96714 | 2.9628 | 2.9637 | 2.9534 | 2.9834 | 2.9724 |
| 5616 | 1781 | 1 | 3.1253 | 3.12946 | 3.1245 | 3.1266 | 3.1188 | 3.1432 | 3.1342 |
| 5628 | 1777 | 1 | 3.4014 | 3.40732 | 3.4035 | 3.4037 | 3.3982 | 3.4176 | 3.4136 |
| 5640 | 1773 | 1 | 3.9219 | 3.9267 | 3.9225 | 3.9257 | 3.9216 | 3.9356 | 3.9281 |
| 5700 | 1754 | 1 | 3.271 | 3.2721 | 3.2677 | 3.2734 | 3.2756 | 3.2707 | 3.2731 |
| 5712 | 1751 | 1 | 3.5186 | 3.5218 | 3.5101 | 3.5287 | 3.5403 | 3.519 | 3.5109 |
| 5724 | 1747 | 1 | 3.967 | 3.9723 | 3.958 | 3.9822 | 3.9968 | 3.9724 | 3.9521 |
| 5736 | 1743 | 1 | 4.5291 | 4.5327 | 4.5232 | 4.5424 | 4.5574 | 4.5313 | 4.5092 |
| 5748 | 1740 | 1 | 5.4361 | 5.431 | 5.4283 | 5.4432 | 5.4697 | 5.4195 | 5.3943 |
| 5760 | 1736 | 1 | 6.2954 | 6.28316 | 6.2855 | 6.2961 | 6.3339 | 6.274 | 6.2263 |
| 5772 | 1733 | 1 | 6.1311 | 6.11846 | 6.1275 | 6.1305 | 6.1556 | 6.1092 | 6.0695 |
| 5784 | 1729 | 1 | 5.3685 | 5.36016 | 5.3687 | 5.3736 | 5.3895 | 5.3388 | 5.3302 |
| 5796 | 1725 | 1 | 4.7353 | 4.73128 | 4.7371 | 4.7434 | 4.7547 | 4.7058 | 4.7154 |
| 5808 | 1722 | 1 | 4.2184 | 4.21624 | 4.2189 | 4.22 | 4.2259 | 4.1997 | 4.2167 |
| 5820 | 1718 | 1 | 3.7382 | 3.7354 | 3.7383 | 3.7317 | 3.7329 | 3.7265 | 3.7476 |
| 5832 | 1715 | 1 | 3.2482 | 3.24516 | 3.252 | 3.2379 | 3.2325 | 3.2378 | 3.2656 |
| 5844 | 1711 | 1 | 2.7005 | 2.69712 | 2.7088 | 2.6865 | 2.6767 | 2.6865 | 2.7271 |
| 5856 | 1708 | 1 | 2.1677 | 2.16416 | 2.1782 | 2.1539 | 2.1453 | 2.1464 | 2.197 |
| 5868 | 1704 | 1 | 1.7811 | 1.777 | 1.7899 | 1.7685 | 1.7611 | 1.7578 | 1.8077 |
| 5880 | 1701 | 1 | 1.543 | 1.53756 | 1.549 | 1.5317 | 1.5247 | 1.5187 | 1.5637 |

TABLE 12.1-continued

Determination of the Properties of a Polyethylene to Control its Manufacture

| Prox. Index | Wt | Measured | 12A Estimated 0.0042626 | 12B 0.0072895 | 12C 0.0095186 | 12D 0.012812 | 12E 0.017956 | 12F 0.020326 |
|---|---|---|---|---|---|---|---|---|

Wavelength

| $\lambda$ (cm −1) | $\lambda$ (nm) | | | | | | | | |
|---|---|---|---|---|---|---|---|---|---|
| 5892 | 1697 | 1 | 1.386 | 1.37964 | 1.3902 | 1.3751 | 1.3678 | 1.362 | 1.4031 |
| 5904 | 1694 | 1 | 1.2531 | 1.24688 | 1.256 | 1.2422 | 1.2334 | 1.2363 | 1.2665 |
| 5916 | 1690 | 1 | 1.1365 | 1.1301 | 1.135 | 1.1265 | 1.1181 | 1.1269 | 1.144 |
| 8040 | 1244 | 1 | 2.017 | 2.00228 | 2.007 | 1.9968 | 1.9988 | 2.0068 | 2.002 |
| 8052 | 1242 | 1 | 2.1798 | 2.16904 | 2.1741 | 2.1633 | 2.1689 | 2.1757 | 2.1632 |
| 8064 | 1240 | 1 | 2.3554 | 2.3495 | 2.3502 | 2.3435 | 2.3506 | 2.3583 | 2.3449 |
| 8076 | 1238 | 1 | 2.5542 | 2.54602 | 2.5463 | 2.5412 | 2.5411 | 2.5583 | 2.5432 |
| 8088 | 1236 | 1 | 2.77 | 2.7631 | 2.764 | 2.7595 | 2.7549 | 2.778 | 2.7591 |
| 8100 | 1235 | 1 | 3.0086 | 3.00852 | 3.006 | 3.01 | 3.0001 | 3.0222 | 3.0043 |
| 8112 | 1233 | 1 | 3.2815 | 3.28462 | 3.281 | 3.2858 | 3.2755 | 3.2932 | 3.2876 |
| 8124 | 1231 | 1 | 3.5883 | 3.59138 | 3.5901 | 3.5889 | 3.5827 | 3.5958 | 3.5994 |
| 8136 | 1229 | 1 | 3.9312 | 3.932 | 3.9335 | 3.9321 | 3.9259 | 3.9335 | 3.935 |
| 8148 | 1227 | 1 | 4.3057 | 4.30886 | 4.3138 | 4.3117 | 4.3029 | 4.3088 | 4.3071 |
| 8160 | 1225 | 1 | 4.6904 | 4.70348 | 4.7083 | 4.7085 | 4.6972 | 4.7021 | 4.7013 |
| 8172 | 1224 | 1 | 5.0567 | 5.0748 | 5.0806 | 5.085 | 5.0706 | 5.0702 | 5.0676 |
| 8184 | 1222 | 1 | 5.3584 | 5.37704 | 5.3885 | 5.3897 | 5.3754 | 5.3703 | 5.3613 |
| 8196 | 1220 | 1 | 5.5454 | 5.56502 | 5.5766 | 5.5765 | 5.5653 | 5.5602 | 5.5465 |
| 8208 | 1218 | 1 | 5.5949 | 5.61744 | 5.6243 | 5.6316 | 5.6174 | 5.6161 | 5.5978 |
| 8304 | 1204 | 1 | 3.9622 | 3.97292 | 3.9776 | 3.9785 | 3.9664 | 3.9677 | 3.9744 |
| 8316 | 1203 | 1 | 3.7097 | 3.71178 | 3.7158 | 3.7128 | 3.7071 | 3.7087 | 3.7145 |
| 8328 | 1201 | 1 | 3.452 | 3.44774 | 3.4551 | 3.4456 | 3.4421 | 3.445 | 3.4509 |
| 8340 | 1199 | 1 | 3.1855 | 3.18512 | 3.1931 | 3.1844 | 3.1794 | 3.1793 | 3.1894 |
| 8352 | 1197 | 1 | 2.9428 | 2.94286 | 2.9445 | 2.9422 | 2.9419 | 2.9321 | 2.9536 |
| 8364 | 1196 | 1 | 2.7439 | 2.74022 | 2.7361 | 2.7369 | 2.7463 | 2.727 | 2.7548 |
| 8376 | 1194 | 1 | 2.6033 | 2.60352 | 2.5999 | 2.603 | 2.6104 | 2.5913 | 2.613 |
| 8388 | 1192 | 1 | 2.5465 | 2.55012 | 2.5457 | 2.553 | 2.5529 | 2.5426 | 2.5564 |
| 8400 | 1190 | 1 | 2.54 | 2.53978 | 2.5322 | 2.5348 | 2.5421 | 2.5409 | 2.5489 |
| 8412 | 1189 | 1 | 2.4926 | 2.48966 | 2.4825 | 2.4746 | 2.4951 | 2.497 | 2.4991 |
| 8424 | 1187 | 1 | 2.3635 | 2.35776 | 2.3517 | 2.343 | 2.3666 | 2.3639 | 2.3636 |
| 8436 | 1185 | 1 | 2.1984 | 2.1897 | 2.1797 | 2.1783 | 2.2041 | 2.1911 | 2.1953 |
| 8448 | 1184 | 1 | 2.047 | 2.03806 | 2.0245 | 2.0367 | 2.0514 | 2.0337 | 2.044 |
| 8460 | 1182 | 1 | 1.9027 | 1.89284 | 1.8818 | 1.8996 | 1.9027 | 1.8872 | 1.8929 |
| 8472 | 1180 | 1 | 1.7662 | 1.75796 | 1.7562 | 1.7615 | 1.7655 | 1.7557 | 1.7509 |
| 8484 | 1179 | 1 | 1.6745 | 1.66826 | 1.6685 | 1.6682 | 1.6732 | 1.6694 | 1.662 |
| 8496 | 1177 | 1 | 1.6317 | 1.61862 | 1.6109 | 1.6228 | 1.6257 | 1.618 | 1.6157 |
| grade | | | 4.4 | 4.3 | 4.2 | 4.4 | 4.1 | 4.3 | 4.6 |
| density | | | 0.953 | 0.952 | 0.952 | 0.953 | 0.952 | 0.952 | 0.951 |

TABLE 13.1

Determination of Percentages of Products leaving the Reactor

| Prox. Index | Wt | Measured | 13A Estimated 0.02713 | 13B 0.074338 | 13C 0.11208 | 13D 0.16551 |
|---|---|---|---|---|---|---|

Wavelength

| $\lambda$ (cm −1) | $\lambda$ (nm) | | | | | | |
|---|---|---|---|---|---|---|---|
| 6460 | 1548 | 0.0046638 | 0.9506 | | 0.9167 | 0.8792 | 0.9062 |
| 6620 | 1511 | 0.013811 | 1.6348 | ?? | 1.5997 | 1.5768 | 1.5894 |
| 6652 | 1503 | 0.010524 | 1.7998 | ?? | 1.7841 | 1.7564 | 1.7742 |
| 6711 | 1490 | 0.015252 | 2.2127 | ?? | 2.1896 | 2.1635 | 2.1819 |
| 6730 | 1486 | 0.017726 | 2.3151 | ?? | 2.2957 | 2.2755 | 2.2865 |
| 6796 | 1471 | 0.0051909 | 2.8005 | ?? | 2.7882 | 2.7608 | 2.7702 |
| 6824 | 1465 | 0.0024562 | 2.8892 | ?? | 2.8978 | 2.8678 | 2.8806 |
| 6996 | 1429 | 0.10627 | 3.7694 | ?? | 3.7794 | 3.7851 | 3.8055 |
| 7028 | 1423 | 0.3675 | 4.8996 | ?? | 4.8146 | 4.9265 | 4.9319 |
| 7076 | 1413 | 0.18801 | 3.9273 | ?? | 3.9644 | 3.9211 | 3.9504 |
| 7150 | 1399 | 0.14604 | 4.1671 | ?? | 4.1628 | 4.1702 | 4.2177 |
| 7215 | 1386 | 0.27199 | 2.6157 | ?? | 2.6289 | 2.5755 | 2.638 |
| 7263 | 1377 | 0.40707 | 3.1178 | ?? | 3.1596 | 3.0514 | 3.0678 |
| 7344 | 1362 | 0.33437 | 1.6553 | ?? | 1.7027 | 1.5795 | 1.598 |

TABLE 13.1-continued

Determination of Percentages of Products leaving the Reactor

| | Wt Prox. Index | Measured | 13A Estimated 0.02713 | 13B 0.074338 | 13C 0.11208 | 13D 0.16551 |
|---|---|---|---|---|---|---|
| 7465 | 1340 | 0.025072 | 0.4511 | ?? | 0.4291 | 0.3898 | 0.3988 |
| 7504 | 1333 | 0.33793 | 0.72 | ?? | 0.7664 | 0.6542 | 0.6631 |
| 8100 | 1235 | 0.79137 | 3.0971 | ?? | 3.0875 | 3.1733 | 3.2087 |
| 8250 | 1212 | 2.5858 | 6.5167 | ?? | 6.4577 | 6.689 | 6.7332 |
| 8332 | 1200 | 0.99957 | 7.0388 | ?? | 6.9601 | 7.1546 | 7.1455 |
| 8434 | 1186 | 0.52305 | 6.3714 | ?? | 6.5339 | 6.3954 | 6.3456 |
| 8592 | 1164 | 1.9117 | 4.3131 | ?? | 4.4163 | 4.2975 | 4.2704 |
| 8660 | 1155 | 0.65567 | 3.8575 | ?? | 3.7572 | 3.7107 | 3.7241 |
| 8710 | 1148 | 0.59466 | 5.0015 | ?? | 5.0538 | 5.0873 | 5.0805 |
| 8767 | 1141 | 0.61289 | 5.4292 | ?? | 5.3749 | 5.5012 | 5.4754 |
| 8796 | 1137 | 0.70638 | 5.5988 | ?? | 5.5164 | 5.6277 | 5.5518 |
| 8815 | 1134 | 0.58808 | 4.6706 | ?? | 4.5946 | 4.6884 | 4.6 |
| 8841 | 1131 | 0.34646 | 3.4155 | ?? | 3.3726 | 3.4198 | 3.3602 |
| 8860 | 1129 | 0.25736 | 2.8157 | ?? | 2.7751 | 2.8008 | 2.7556 |
| 8936 | 1119 | 0.19692 | 1.203 | ?? | 1.2403 | 1.1788 | 1.1695 |
| 8955 | 1117 | 0.17434 | 0.9454 | ?? | 0.9796 | 0.9423 | 0.9195 |
| Light Fraction | | | 12.85 | ?? | 16.99 | 12.24 | 12.39 |
| Heavy Fraction | | | 42.71 | ?? | 36.19 | 41.94 | 40.78 |

TABLE 13.2

New "Standard" MC1 obtained by Densification

| | | MC1 | 13B | 13E | 13C |
|---|---|---|---|---|---|
| Fraction in the Mixture | | | 0,888 | 0,277 | −0,165 |
| λ (cm-1) | λ (nm) | | | | |
| 6460 | 1548 | 0,94283 | 0,9167 | 0,9887 | 0,8792 |
| 6620 | 1511 | 1,632 | 1,5997 | 1,7026 | 1,5768 |
| 6652 | 1503 | 1,8099 | 1,7841 | 1,8607 | 1,7564 |
| 6711 | 1490 | 2,2102 | 2,1896 | 2,2483 | 2,1635 |
| 6730 | 1486 | 2,3157 | 2,2957 | 2,356 | 2,2755 |
| 6796 | 1471 | 2,7984 | 2,7882 | 2,8087 | 2,7608 |
| 6824 | 1465 | 2,9 | 2,8978 | 2,8877 | 2,8678 |
| 6996 | 1429 | 3,7874 | 3,7794 | 3,8116 | 3,7851 |
| 7028 | 1423 | 4,8919 | 4,8146 | 5,1604 | 4,9265 |
| 7076 | 1413 | 3,9441 | 3,9644 | 3,8653 | 3,9211 |
| 7150 | 1399 | 4,1768 | 4,1628 | 4,2177 | 4,1702 |
| 7215 | 1386 | 2,61 | 2,6289 | 2,5287 | 2,5755 |
| 7263 | 1377 | 3,1169 | 3,1596 | 2,9409 | 3,0514 |
| 7344 | 1362 | 1,6447 | 1,7027 | 1,4198 | 1,5795 |
| 7465 | 1340 | 0,43655 | 0,4291 | 0,4326 | 0,3898 |
| 7504 | 1333 | 0,70392 | 0,7664 | 0,474 | 0,6542 |
| 8100 | 1235 | 3,0909 | 3,0875 | 3,1509 | 3,1733 |
| 8250 | 1212 | 6,5248 | 6,4577 | 6,8378 | 6,689 |
| 8332 | 1200 | 7,0355 | 6,9601 | 7,3483 | 7,1546 |
| 8434 | 1186 | 6,4076 | 6,5339 | 5,9953 | 6,3954 |
| 8592 | 1164 | 4,3058 | 4,4163 | 3,9466 | 4,2975 |
| 8660 | 1155 | 3,6516 | 3,7572 | 3,3484 | 3,7107 |
| 8710 | 1148 | 4,9879 | 5,0538 | 4,8357 | 5,0873 |
| 8767 | 1141 | 5,4021 | 5,3749 | 5,5484 | 5,5012 |
| 8796 | 1137 | 5,5708 | 5,5164 | 5,7792 | 5,6277 |
| 8815 | 1134 | 4,6591 | 4,5946 | 4,8835 | 4,6884 |
| 8841 | 1131 | 3,4302 | 3,3726 | 3,6088 | 3,4198 |
| 8860 | 1129 | 2,8374 | 2,7751 | 3,0153 | 2,8008 |
| 8936 | 1119 | 1,2122 | 1,2403 | 1,1023 | 1,1788 |
| 8955 | 1117 | 0,96257 | 0,9796 | 0,8959 | 0,9423 |
| Light Fraction | | | 13,12 | 16,99 | 0,17 | 12,24 |
| Heavy Fraction | | | 42,11 | 36,19 | 60,98 | 41,94 |

TABLE 13.3

New "Standard" MC2 obtained by Densification

| | | MC2 | 13B | 13D | 13E |
|---|---|---|---|---|---|
| Fraction in the Mixture | | | 0,877 | −0,136 | 0,259 |
| Wavelength | | | | | |
| λ (cm-1) | λ (nm) | | | | |
| 6460 | 1548 | 0,93678 | 0,9167 | 0,9062 | 0,9887 |
| 6620 | 1511 | 1,6278 | 1,5997 | 1,5894 | 1,7026 |
| 6652 | 1503 | 1,8053 | 1,7841 | 1,7742 | 1,8607 |
| 6711 | 1490 | 2,2059 | 2,1896 | 2,1819 | 2,2483 |
| 6730 | 1486 | 2,3126 | 2,2957 | 2,2865 | 2,356 |
| 6796 | 1471 | 2,796 | 2,7882 | 2,7702 | 2,8087 |
| 6824 | 1465 | 2,8975 | 2,8978 | 2,8806 | 2,8877 |
| 6996 | 1429 | 3,7842 | 3,7794 | 3,8055 | 3,8116 |
| 7028 | 1423 | 4,8882 | 4,8146 | 4,9319 | 5,1604 |
| 7076 | 1413 | 3,9406 | 3,9644 | 3,9504 | 3,8653 |
| 7150 | 1399 | 4,1696 | 4,1628 | 4,2177 | 4,2177 |
| 7215 | 1386 | 2,6017 | 2,6289 | 2,638 | 2,5287 |
| 7263 | 1377 | 3,1154 | 3,1596 | 3,0678 | 2,9409 |
| 7344 | 1362 | 1,6437 | 1,7027 | 1,598 | 1,4198 |
| 7465 | 1340 | 0,43413 | 0,4291 | 0,3988 | 0,4326 |
| 7504 | 1333 | 0,70472 | 0,7664 | 0,6631 | 0,474 |
| 8100 | 1235 | 3,0874 | 3,0875 | 3,2087 | 3,1509 |
| 8250 | 1212 | 6,5187 | 6,4577 | 6,7332 | 6,8378 |
| 8332 | 1200 | 7,0354 | 6,9601 | 7,1455 | 7,3483 |
| 8434 | 1186 | 6,42 | 6,5339 | 6,3456 | 5,9953 |
| 8592 | 1164 | 4,3145 | 4,4163 | 4,2704 | 3,9466 |
| 8660 | 1155 | 3,6558 | 3,7572 | 3,7241 | 3,3484 |
| 8710 | 1148 | 4,9937 | 5,0538 | 5,0805 | 4,8357 |
| 8767 | 1141 | 5,4062 | 5,3749 | 5,4754 | 5,5484 |
| 8796 | 1137 | 5,5797 | 5,5164 | 5,5518 | 5,7792 |
| 8815 | 1134 | 4,6687 | 4,5946 | 4,6 | 4,8835 |
| 8841 | 1131 | 3,4355 | 3,3726 | 3,3602 | 3,6088 |
| 8860 | 1129 | 2,84 | 2,7751 | 2,7556 | 3,0153 |
| 8936 | 1119 | 1,2142 | 1,2403 | 1,1695 | 1,1023 |
| 8955 | 1117 | 0,9661 | 0,9796 | 0,9195 | 0,8959 |
| Light Fraction | | | 13,26 | 16,99 | 12,39 | 0,17 |
| Heavy Fraction | | | 41,99 | 36,19 | 40,78 | 60,98 |

TABLE 13.4

Determination of Percentages of Product leaving Reactor based on New "Standards"

| | | Wt | 13A | | 13B | MC1 | MC2 |
|---|---|---|---|---|---|---|---|
| | | | Measured | Estimated | | | |
| | Prox. Index | | | 0.0025577 | 0.0027389 | 0.0026436 | |

Wavelength

| λ (cm −1) | λ (nm) | | | | | | |
|---|---|---|---|---|---|---|---|
| 6460 | 1548 | 0.0046638 | 0.9506 | 0.9398 | 0.94283 | 0.93678 | |
| 6620 | 1511 | 0.013811 | 1.6348 | 1.6299 | 1.632 | 1.6278 | |
| 6652 | 1503 | 0.010524 | 1.7998 | 1.8076 | 1.8099 | 1.8053 | |
| 6711 | 1490 | 0.015252 | 2.2127 | 2.208 | 2.2102 | 2.2059 | |
| 6730 | 1486 | 0.017726 | 2.3151 | 2.3142 | 2.3157 | 2.3126 | |
| 6796 | 1471 | 0.0051909 | 2.8005 | 2.7972 | 2.7984 | 2.796 | |
| 6824 | 1465 | 0.0024562 | 2.8892 | 2.8987 | 2.9 | 2.8975 | |
| 6996 | 1429 | 0.10627 | 3.7694 | 3.7858 | 3.7874 | 3.7842 | |
| 7028 | 1423 | 0.3675 | 4.8996 | 4.8901 | 4.8919 | 4.8882 | |
| 7076 | 1413 | 0.18801 | 3.9273 | 3.9424 | 3.9441 | 3.9406 | |
| 7150 | 1399 | 0.14604 | 4.1671 | 4.1732 | 4.1768 | 4.1696 | |
| 7215 | 1386 | 0.27199 | 2.6157 | 2.6058 | 2.61 | 2.6017 | |
| 7263 | 1377 | 0.40707 | 3.1178 | 3.1162 | 3.1169 | 3.1154 | |
| 7344 | 1362 | 0.33437 | 1.6553 | 1.6442 | 1.6447 | 1.6437 | |
| 7465 | 1340 | 0.025072 | 0.4511 | 0.43534 | 0.43655 | 0.43413 | |
| 7504 | 1333 | 0.33793 | 0.72 | 0.70432 | 0.70392 | 0.70472 | |
| 8100 | 1235 | 0.79137 | 3.0971 | 3.0892 | 3.0909 | 3.0874 | |
| 8250 | 1212 | 2.5858 | 6.5167 | 6.5218 | 6.5248 | 6.5187 | |
| 8332 | 1200 | 0.99957 | 7.0388 | 7.0355 | 7.0355 | 7.0354 | |
| 8434 | 1186 | 0.52305 | 6.3714 | 6.4138 | 6.4076 | 6.42 | |
| 8592 | 1164 | 1.9117 | 4.3131 | 4.3101 | 4.3058 | 4.3145 | |
| 8660 | 1155 | 0.65567 | 3.6575 | 3.6537 | 3.6516 | 3.6558 | |
| 8710 | 1148 | 0.59466 | 5.0015 | 4.9908 | 4.9879 | 4.9937 | |
| 8767 | 1141 | 0.61289 | 5.4292 | 5.4041 | 5.4021 | 5.4062 | |
| 8796 | 1137 | 0.70638 | 5.5988 | 5.5752 | 5.5708 | 5.5797 | |
| 8815 | 1134 | 0.58803 | 4.6706 | 4.6639 | 4.6591 | 4.6687 | |
| 8841 | 1131 | 0.34646 | 3.4155 | 3.4329 | 3.4302 | 3.4355 | |
| 8860 | 1129 | 0.25736 | 2.8157 | 2.8387 | 2.8374 | 2.84 | |
| 8936 | 1119 | 0.19692 | 1.203 | 1.2132 | 1.2122 | 1.2142 | |
| 8955 | 1117 | 0.17434 | 0.9454 | 0.96433 | 0.96257 | 0.9661 | |
| Light Fraction | | | 12.85 | 13.19 | 13.12 | 13.26 | |
| Heavy Fraction | | | 42.71 | 42.05 | 42.11 | 41.99 | |

TABLE 13.5

Immediate use of new "Standard" by Autoadjustment

| | | Wt | 13F | | 13A |
|---|---|---|---|---|---|
| | | | Measured | Estimated | pib 13 |
| Prox. index | | | | 0,0020232 | 0,0020232 |

Wavelength

| λ (cm-1) | λ (nm) | | | | |
|---|---|---|---|---|---|
| 6460 | 1548 | 0,0046638 | 0,94974 | 0,9506 | 0,9506 |
| 6620 | 1511 | 0,013811 | 1,6313 | 1,6348 | 1,6348 |
| 6652 | 1503 | 0,010524 | 1,8058 | 1,7998 | 1,7998 |
| 6711 | 1490 | 0,015252 | 2,2127 | 2,2127 | 2,2127 |
| 6730 | 1486 | 0,017726 | 2,3113 | 2,3151 | 2,3151 |
| 6796 | 1471 | 0,0051909 | 2,7958 | 2,8005 | 2,8005 |
| 6824 | 1465 | 0,0024562 | 2,8874 | 2,8892 | 2,8892 |
| 6996 | 1429 | 0,10627 | 3,7659 | 3,7694 | 3,7694 |
| 7028 | 1423 | 0,3675 | 4,9065 | 4,8996 | 4,8996 |
| 7076 | 1413 | 0,18801 | 3,918 | 3,9273 | 3,9273 |
| 7150 | 1399 | 0,14604 | 4,1745 | 4,1671 | 4,1671 |
| 7215 | 1386 | 0,27199 | 2,6134 | 2,6157 | 2,6157 |
| 7263 | 1377 | 0,40707 | 3,1197 | 3,1178 | 3,1178 |
| 7344 | 1362 | 0,33437 | 1,654 | 1,6553 | 1,6553 |
| 7465 | 1340 | 0,025072 | 0,4501 | 0,4511 | 0,4511 |
| 7504 | 1333 | 0,33793 | 0,72137 | 0,72 | 0,72 |
| 8100 | 1235 | 0,79137 | 3,0929 | 3,0971 | 3,0971 |
| 8250 | 1212 | 2,5858 | 6,5384 | 6,5167 | 6,5167 |
| 8332 | 1200 | 0,99957 | 7,0344 | 7,0388 | 7,0388 |
| 8434 | 1186 | 0,52305 | 6,3814 | 6,3714 | 6,3714 |
| 8592 | 1164 | 1,9117 | 4,3249 | 4,3131 | 4,3131 |
| 8660 | 1155 | 0,65567 | 3,6709 | 3,6575 | 3,6575 |
| 8710 | 1148 | 0,59466 | 4,9942 | 5,0015 | 5,0015 |
| 8767 | 1141 | 0,61289 | 5,4319 | 5,4292 | 5,4292 |
| 8796 | 1137 | 0,70638 | 5,5822 | 5,5988 | 5,5988 |
| 8815 | 1134 | 0,58808 | 4,6679 | 4,6706 | 4,6706 |
| 8841 | 1131 | 0,34646 | 3,4061 | 3,4155 | 3,4155 |
| 8860 | 1129 | 0,25736 | 2,8072 | 2,8157 | 2,8157 |
| 8936 | 1119 | 0,19692 | 1,2042 | 1,203 | 1,203 |
| 8955 | 1117 | 0,17434 | 0,94588 | 0,9454 | 0,9454 |
| Light Fraction | | | 12,55 | 12,85 | 12,85 |
| Heavy Fraction | | | 43,35 | 42,71 | 42,71 |

TABLE 14.1

Determination of Properties of a PEG to control a Production Unit

| | | Wt | 14A | | 14B | 14C | 14D | 14E |
|---|---|---|---|---|---|---|---|---|
| | Prox. | | Measured | Estimated 0.00006519 | 0.00000977 | 0.00007494 | 0.00010457 | 0.00011574 |
| Index | | | | | | | | |
| Wavelength | | | | | | | | |
| λ (cm −1) | λ (nm) | | | | | | | |
| 4164 | 2402 | 1 | 0.12662 | 0.121605 | 0.12559 | 0.1212 | 0.12117 | 0.11846 |
| 4308 | 2321 | 1 | 0.24254 | 0.2387275 | 0.24285 | 0.23781 | 0.23696 | 0.23729 |
| 4524 | 2210 | 1 | 0.054854 | 0.0567045 | 0.054802 | 0.056171 | 0.057599 | 0.058246 |
| 4836 | 2068 | 1 | 0.048031 | 0.0485855 | 0.048451 | 0.048238 | 0.048588 | 0.049065 |
| 5172 | 1933 | 1 | 0.059102 | 0.06188575 | 0.061585 | 0.061986 | 0.064102 | 0.05987 |
| 5436 | 1840 | 1 | 0.056088 | 0.0555625 | 0.056049 | 0.0555 | 0.055054 | 0.055647 |
| 5544 | 1804 | 1 | 0.068293 | 0.06745175 | 0.067773 | 0.066995 | 0.067073 | 0.067966 |
| 5748 | 1740 | 1 | 0.10824 | 0.107665 | 0.10872 | 0.10703 | 0.10673 | 0.10818 |
| 5856 | 1708 | 1 | 0.037196 | 0.0374255 | 0.037003 | 0.037603 | 0.037295 | 0.037801 |
| 6624 | 1510 | 1 | 0.014687 | 0.015498 | 0.014728 | 0.016063 | 0.01551 | 0.015691 |
| 6684 | 1496 | 1 | 0.019234 | 0.01960475 | 0.019068 | 0.019792 | 0.019826 | 0.019733 |
| 6720 | 1488 | 1 | 0.020139 | 0.02084475 | 0.020349 | 0.021013 | 0.020942 | 0.021075 |
| 6792 | 1472 | 1 | 0.022751 | 0.023453 | 0.022848 | 0.023636 | 0.023758 | 0.02357 |
| 6972 | 1434 | 1 | 0.030389 | 0.03078325 | 0.030175 | 0.030929 | 0.03119 | 0.030839 |
| 7092 | 1410 | 1 | 0.021148 | 0.02166525 | 0.021221 | 0.022095 | 0.021621 | 0.021724 |
| 7116 | 1405 | 1 | 0.021822 | 0.02246175 | 0.02158 | 0.022824 | 0.02273 | 0.022713 |
| 7920 | 1263 | 1 | 0.004193 | 0.00522035 | 0.0042156 | 0.0057718 | 0.0054551 | 0.0054389 |
| 8172 | 1224 | 1 | 0.03318 | 0.0330015 | 0.032074 | 0.032927 | 0.032945 | 0.03406 |
| 8352 | 1197 | 1 | 0.011492 | 0.0118575 | 0.010926 | 0.012427 | 0.011449 | 0.012628 |
| Hydroxyl Index | | | 13.1 | 13.1 | 13.1 | 13 | 13.2 | 13.15 |
| Viscosity | | | 701 | 704 | 703 | 710 | 708 | 695 |
| Molec. Weight | | | 8560 | 8612.5 | 8400 | 8370 | 8450 | 9230 |

EXAMPLES 15
Determination of the Properties of a Base Oil

The NIR spectrum of a base oil D which was a 500 neutral oil was measured between 4800 and 4000 cm$^{-1}$ with normalisation of the absorbances, [the base line being taken at 4780 cm$^{-1}$]. NIR spectra were recorded for a series of standard base oils of known properties. By the Minimal Index Procedure described above, with use of Equation 2, and non weighting of the absorbancies, the Minimal Index was calculated to be 5×10$^{-7}$. Following reference to the bank of data on the standard base oils, 3 standards 15A, 15B and 15C were found with the proximity index with respect to oil D less than 5×10$^{-7}$. The properties of those standards and their spectra are shown in Table 15.1. By averaging the properties of the standard samples, various properties were obtained for the oil D. The Table 15 shows the estimated properties as well as measured properties of oil D for comparison.

All the properties were determined in a single analysis and without any regressional type calculations and with a degree of precision in line with the reproducibility of the reference methods.

Other properties of D can be determined in a similar way.

EXAMPLE 16
Determination of the properties of a Process Oil

The method of Example 15 was repeated with a process Oil Reference 16D of "Enerthene" type which was a mixture of neutral base oil and aromatic-containing vacuum distillate extract. From a bank of standard process oils of this type, Minimal Index was found by the Minimal Index Procedure to be 5×10$^{-7}$, providing a sphere of identity. 3 standard oils 16A, 16B and 16C were found with proximity indices with respect to 16D less than the Minimal Index and hence inside that sphere. The properties of oils 16A, 16B, 16C and their spectra and the spectrum of 16D are given in Table 16.1. By arithmetic mean averaging of the properties of 16A, 16B and 16C, the properties of 16D were estimated, and these together with the measured properties of 16D are given also in Table 16.1.

The single analysis gave all the properties without regression calculation and with an accuracy in line with the reproducibility of the reference methods. Other properties can be determined in a similar way.

In Table 16.1, the expression 4.20 E-04 means 4.2×10$^{-4}$ and PCA means Polycyclic Aromatic hydrocarbon.

EXAMPLE 17
Determination of the Properties of a Crude Paraffin

The method of Example 15 was repeated with a crude paraffin (a "slack" wax), which was a mixture of paraffin wax and base oil called Gatsche D. From a bank of standard crude paraffins and their properties and spectra, the Minimal Index was found to be 5×10$^{-5}$, by the Minimal Index Procedure. 3 standard crude paraffins Gatsche 17A, 17B and 17C were found with proximity indices with respect to 17D inside the sphere of identity. The properties of paraffins 17A, 17B, 17C and their spectra, and the spectrum of 17D are given in Table 17.1. By arithmetic means averaging of the properties of 17A, 17B and 17C the properties of 17D were estimated, and these together with the measured properties of 17D are given also in Table 17.1. The properties determined were density, viscosity at 100° C. and oil content. The determination of the oil content of crude paraffin according to the above procedure is particularly remarkable because no on line process capable of measuring this is known today.

All the properties were determined in a single analysis without any regression type calculation and with an accuracy in line with the reproducibility of the reference methods. Other properties of D can be determined in a similar way.

EXAMPLE 18

In a modification of the process of Example 2a, the 6 components were then mixed in the desired proportions, the mixing controlled by the method of the invention applied to the spectra from the components present (see Results in Table 2a4). In the comparison with the bank of standards, the Minimum Index was $1\times10^{-4}$, 3 standards 2D, 2E, 2F were found with suitable proximity indices for which standards the average value of the properties corresponded to $V_c$, the desired value of the property of the target fuel. The blending process was controlled to maintain the 3 standards 2D, 2E, 1F as those with the suitable proximity indices and hence keep substantially constant the properties of the superfuel. For double checking the properties of the blend made and the properties estimated by averaging those from the standards 2D, 2E and 2F were compared; the differences are very small and in the area of reproducibility of the standard methods.

EXAMPLE 19

In a modification of the process of Example 4, the conditions in the distillation unit were maintained in order to keep the 2 standards 4A and 4B as those with small enough proximity indices and hence to keep the properties and yields of the products substantially constant. To double check the process, the properties of standards, estimated (averaged) yields, properties of the products and actual yields were compared, the differences observed being in accordance with standard methods of measurement.

EXAMPLE 20

In a modification of the process of Example 7, the cracking process was controlled to keep these 2 standards 7A and 7B as those with the smallest proximity indices. To cross check the yields of products were determined experimentally and also estimated by averaging from the standards. The properties and yields estimated as shown in Table 7.1. The results were all in line with the accuracy based on the reference methods, as well as in line with the properties and yields actually measured.

EXAMPLE 21

In a modification of the process of Example 10, the plant was controlled to keep the 5 standards 10B–F those with the lowest proximity indices. Checking of the process was performed, by averaging the values of each property of those 5 standards in order to calculate the properties for the product namely the viscosity at 100° C., the number average molecular weight (MN), size of the distribution of molecular weights obtained by gel permeation chromatography (called LGPC) as well as the content of butene-1 (BUT-1).

EXAMPLE 22

In a modification of the process of Example 11, the operating process was controlled to keep the 5 standards 11B–F the ones with lowest proximity indices. To check, the properties of the product were determined, and were all within the limits of reproducibility of the standard methods.

EXAMPLE 23

In a modification of the process of Example 12, the polymerisation process was controlled to keep the 3 standards 12B–D as those with the smallest proximity indices and hence to keep the properties of the product substantially constant.

EXAMPLE 24

In a modification of the process of Example 14, the process was controlled to keep the 4 standards 14A–D, those with proximity indices less than the Minimal Index and hence to maintain the properties of the product.

EXAMPLE 25

In a modification of the process of Example 16, the mixing process was controlled to keep the standards 16A–C the ones with the lowest proximity indices with respect to the product oil and hence to maintain its properties.

TABLE 15.1

| | | | | | | |
|---|---|---|---|---|---|---|
| | | \multicolumn{5}{c}{Determination of the properties of Base Oil} | | | | |
| Proximity Index | Loading | Oil D Measured | Oil D Estimated | Oil 15A $8.8 \times 10^{-8}$ | Oil 15B $4 \times 10^{-8}$ | Oil 15C $4.6 \times 10^{-7}$ |
| Wavelength | | | | | | |
| $\lambda$(cm −1) $\lambda$(nm) | | | | | | |
| 4632 2158 | 1 | 4.9000000E-04 | 5.0333333E-04 | 5.1000000E-04 | 5.0000000E-04 | 5.0000000E-04 |
| 4624 2162 | 1 | 5.7000000E-04 | 5.8000000E-04 | 5.9000000E-04 | 5.9000000E-04 | 5.6000000E-04 |
| 4616 2166 | 1 | 6.1000000E-04 | 6.2000000E-04 | 6.3000000E-04 | 6.1000000E-04 | 6.2000000E-04 |
| 4600 2173 | 1 | 7.8000000E-04 | 7.7000000E-04 | 7.8000000E-04 | 7.6000000E-04 | 7.7000000E-04 |
| 4592 2177 | 1 | 8.4000000E-04 | 8.4000000E-04 | 8.5000000E-04 | 8.3000000E-04 | 8.4000000E-04 |
| 4576 2185 | 1 | 8.5000000E-04 | 8.4666667E-04 | 8.4000000E-04 | 8.5000000E-04 | 8.5000000E-04 |
| 4568 2189 | 1 | 8.1000000E-04 | 8.0333333E-04 | 8.0000000E-04 | 8.1000000E-04 | 8.0000000E-04 |
| 4560 2192 | 1 | 8.6000000E-04 | 8.7333333E-04 | 8.8000000E-04 | 8.8000000E-04 | 8.6000000E-04 |
| 4540 2202 | 1 | 9.3000000E-04 | 9.2333333E-04 | 9.2000000E-04 | 9.2000000E-04 | 9.3000000E-04 |
| 4504 2220 | 1 | 1.2800000E-03 | 1.2933333E-03 | 1.2900000E-03 | 1.3000000E-03 | 1.2900000E-03 |
| 4472 2236 | 1 | 1.9900000E-03 | 2.0000000E-03 | 2.0000000E-03 | 2.0000000E-03 | 2.0000000E-03 |
| 4440 2252 | 1 | 4.2300000E-03 | 4.2433333E-03 | 4.2500000E-03 | 4.2500000E-03 | 4.2300000E-03 |
| 4432 2256 | 1 | 5.5300000E-03 | 5.5233333E-03 | 5.5300000E-03 | 5.5500000E-03 | 5.4900000E-03 |
| 4424 2260 | 1 | 7.4300000E-03 | 7.4266667E-03 | 7.4300000E-03 | 7.4500000E-03 | 7.4000000E-03 |
| 4416 2264 | 1 | 9.7800000E-03 | 9.7900000E-03 | 9.8000000E-03 | 9.8200000E-03 | 9.7500000E-03 |
| 4408 2268 | 1 | 1.2690000E-02 | 1.2693333E-02 | 1.2710000E-02 | 1.2730000E-02 | 1.2640000E-02 |

TABLE 15.1-continued

Determination of the properties of Base Oil

| Proximity Index | Loading | Oil D Measured | Oil D Estimated | Oil 15A 8.8 × 10⁻⁸ | Oil 15B 4 × 10⁻⁸ | Oil 15C 4.6 × 10⁻⁷ |
|---|---|---|---|---|---|---|
| 4400 2272 | 1 | 1.5840000E-02 | 1.5810000E-02 | 1.5810000E-02 | 1.5870000E-02 | 1.5750000E-02 |
| 4392 2276 | 1 | 1.7970000E-02 | 1.7940000E-02 | 1.7960000E-02 | 1.7970000E-02 | 1.7890000E-02 |
| 4382 2282 | 1 | 1.9140000E-02 | 1.9126667E-02 | 1.9150000E-02 | 1.9140000E-02 | 1.9090000E-02 |
| 4376 2285 | 1 | 1.9700000E-02 | 1.9696667E-02 | 1.9730000E-02 | 1.9720000E-02 | 1.9640900E-02 |
| 4368 2289 | 1 | 2.0450000E-02 | 2.0460000E-02 | 2.0480000E-02 | 2.0460000E-02 | 2.0440000E-02 |
| 4352 2297 | 1 | 2.6140000E-02 | 2.6106667E-02 | 2.6130000E-02 | 2.6130000E-02 | 2.6060000E-02 |
| 4344 2302 | 1 | 3.2330000E-02 | 3.2136667E-02 | 3.2300000E-02 | 3.2330000E-02 | 3.2320000E-02 |
| 4330 2309 | 1 | 4.3200000E-02 | 4.3226667E-02 | 4.3290000E-02 | 4.3170000E-02 | 4.3220000E-02 |
| 4320 2314 | 1 | 3.6600000E-02 | 3.6566667E-02 | 3.6550000E-02 | 3.6550000E-02 | 3.6600000E-02 |
| 4312 2319 | 1 | 2.9970000E-02 | 2.9933333E-02 | 2.9930000E-02 | 2.9970000E-02 | 2.9900000E-02 |
| 4304 2323 | 1 | 2.6610000E-02 | 2.6566667E-02 | 2.6570000E-02 | 2.6590000E-02 | 2.6540000E-02 |
| 4296 2327 | 1 | 2.4540000E-02 | 2.4500000E-02 | 2.4490000E-02 | 2.4510000E-02 | 2.4500000E-02 |
| 4290 2331 | 1 | 2.3810000E-02 | 2.3830000E-02 | 2.3820000E-02 | 2.3870000E-02 | 2.3800000E-02 |
| 4280 2336 | 1 | 2.5390000E-02 | 2.5346667E-02 | 2.5360000E-02 | 2.5340000E-02 | 2.5340000E-02 |
| 4272 2340 | 1 | 2.9140000E-02 | 2.9163333E-02 | 2.9190000E-02 | 2.9140000E-02 | 2.9160000E-02 |
| 4258 2348 | 1 | 3.7380000E-02 | 3.7363333E-02 | 3.7330000E-02 | 3.7370000E-02 | 3.7390000E-02 |
| 4248 2354 | 1 | 3.2840000E-02 | 3.2830000E-02 | 3.2820000E-02 | 3.2820000E-02 | 3.2850000E-02 |
| 4240 2358 | 1 | 2.8100000E-02 | 3.8090000E-02 | 2.8080000E-02 | 2.8100000E-02 | 2.8090000E-02 |
| 4232 2362 | 1 | 2.6100000E-02 | 2.6083333E-02 | 2.6120000E-02 | 2.6050000E-02 | 2.6080000E-02 |
| 4224 2367 | 1 | 2.5820000E-02 | 2.5850000E-02 | 2.5830000E-02 | 2.5840000E-02 | 2.5880000E-02 |
| 4212 2374 | 1 | 2.5640000E-02 | 2.5653333E-02 | 2.5670000E-02 | 2.5620000E-02 | 2.5670000E-02 |
| 4200 2380 | 1 | 2.5860000E-02 | 2.5353333E-02 | 2.5820000E-02 | 2.5840000E-02 | 2.5900000E-02 |
| 4192 2385 | 1 | 2.5820000E-02 | 2.5846667E-02 | 2.5820000E-02 | 2.5800000E-02 | 2.5920000E-02 |
| 4184 2390 | 1 | 2.5970000E-02 | 2.6003333E-02 | 2.6010000E-02 | 2.5970000E-02 | 2.6030000E-02 |
| 4176 2394 | 1 | 2.6210000E-02 | 2.6236667E-02 | 2.6240000E-02 | 2.6190000E-02 | 2.6280000E-02 |
| 4170 2398 | 1 | 2.6600000E-02 | 2.6593333E-02 | 2.6560000E-02 | 2.6580000E-02 | 2.6640000E-02 |
| 4160 2403 | 1 | 2.6370000E-02 | 2.6390000E-02 | 2.6380000E-02 | 2.6370000E-02 | 2.6420000E-02 |
| 4152 2408 | 1 | 2.5710000E-02 | 2.5710000E-02 | 2.5690000E-02 | 2.5710000E-02 | 2.5730000E-02 |
| 4136 2417 | 1 | 2.4620000E-02 | 2.4633333E-02 | 2.4600000E-02 | 2.4640000E-02 | 2.4660000E-02 |
| 4120 2427 | 1 | 2.3990000E-02 | 2.3993333E-02 | 2.3980000E-02 | 2.4000000E-02 | 2.4000000E-02 |
| 4104 2436 | 1 | 2.3060000E-02 | 1.5370000E-02 | 2.3050000E-02 | 2.3060000E-02 | 2.3090000E-02 |
| 4092 2443 | 1 | 2.2600000E-02 | 2.2613333E-02 | 2.2600000E-02 | 2.2610000E-02 | 2.2630000E-02 |
| 4080 2450 | 1 | 2.2730000E-02 | 2.2740000E-02 | 2.2720000E-02 | 2.2730000E-02 | 2.2770000E-02 |
| 4072 2455 | 1 | 2.3350000E-02 | 2.3363333E-02 | 2.3330000E-02 | 2.3370000E-02 | 2.3390000E-02 |
| 4068 2458 | 1 | 2.3640000E-02 | 2.3636667E-02 | 2.3650000E-02 | 2.3610000E-02 | 2.3650000E-02 |
| 4048 2470 | 1 | 2.0700000E-02 | 2.0726667E-02 | 2.0720000E-02 | 2.0720000E-02 | 2.0740000E-02 |
| 4000 2500 | 1 | 1.5150000E-02 | 1.5166667E-02 | 1.5170000E-02 | 1.5140000E-02 | 1.5190000E-02 |
| Density kg/l | | 0.8901 | 0.8898 | 0.8900 | 0.8898 | 0.8896 |
| Sulphur % | | 1.1 | 1.11 | 1.1 | 1.12 | 1.12 |
| Pour Point ° C. | | −9 | −9 | −10 | −9 | −8 |
| Viscosity at 40° C. cSt | | 96.8 | 97.04 | 94.08 | 98.3 | 98.74 |
| Viscosity at 100° C. cSt | | 10.84 | 10.85 | 10.65 | 10.92 | 11 |
| Viscosity Index VI | | 95 | 95.2 | 95.5 | 94.7 | 95.5 |
| Aromatic Carbon % | | 8 | 7.6 | 7.5 | 7.4 | 8 |
| Inflammability Pensky-Martens ° C. | | 239 | 241 | 244 | 239 | 240 |
| Nitrogen base content ppm | | 60 | 59 | 56 | 60 | 63 |

TABLE 16.1

Determination of the properties of a process oil

| | | Oil D | Oil D Estimated | Oil 16A | Oil 16B | Oil 16C |
|---|---|---|---|---|---|---|
| | | | | Proximity index | | |
| | Loading | Measured | 1.09 × 10⁻⁷ | 3.5 × 10⁻⁷ | 1.19 × 10⁻⁷ | 2.19 × 10⁻⁷ |
| Wavelength | | | | | | |
| λ (cm-1)  λ (nm) | | | | | | |
| 4700  2127 | 1 | 4,2000000E − 04 | 3,5000000E − 04 | 3,2000000E − 04 | 3,5000000E − 04 | 3,8000000E − 04 |
| 4688  2133 | 1 | 7,3000000E − 04 | 6,4666667E − 04 | 6,1000000E − 04 | 6,7000000E − 04 | 6,6000000E − 04 |

TABLE 16.1-continued

Determination of the properties of a process oil

| | | | Oil D | Oil D Estimated | Oil 16A | Oil 16B | Oil 16C |
|---|---|---|---|---|---|---|---|
| | | | | | Proximity index | | |
| | | Loading | Measured | $1.09 \times 10^{-7}$ | $3.5 \times 10^{-7}$ | $1.19 \times 10^{-7}$ | $2.19 \times 10^{-7}$ |
| 4680 | 2136 | 1 | 9,8000000E − 04 | 9,6333333E − 04 | 9,6000000E − 04 | 9,4000000E − 04 | 9,9000000E − 04 |
| 4664 | 2144 | 1 | 1,8300000E − 03 | 1,7833333E − 03 | 1,7600000E − 03 | 1,7600000E − 03 | 1,8300000E − 03 |
| 4656 | 2147 | 1 | 2,1600000E − 03 | 2,0900000E − 03 | 2,0900000E − 03 | 2,0600000E − 03 | 2,1200000E − 03 |
| 4648 | 2151 | 1 | 2,5100000E − 03 | 2,4300000E − 03 | 2,4100000E − 03 | 2,4100000E − 03 | 2,4700000E − 03 |
| 4632 | 2158 | 1 | 2,9500000E − 03 | 2,9233333E − 03 | 2,8600000E − 03 | 2,9100000E − 03 | 3,0000000E − 03 |
| 4624 | 2162 | 1 | 3,1100000E − 03 | 3,0966667E − 03 | 3,0100000E − 03 | 3,0800000E − 03 | 3,2000000E − 03 |
| 4616 | 2166 | 1 | 3,1700000E − 03 | 3,1833333E − 03 | 3,1200000E − 03 | 3,1800000E − 03 | 3,2500000E − 03 |
| 4600 | 2173 | 1 | 3,1000000E − 03 | 3,1466667E − 03 | 3,1100000E − 03 | 3,1600000E − 03 | 3,1700000E − 03 |
| 4592 | 2177 | 1 | 3,0700000E − 03 | 3,0500000E − 03 | 3,0000000E − 03 | 3,0500000E − 03 | 3,1000000E − 03 |
| 4576 | 2185 | 1 | 2,6300000E − 03 | 2,5800000E − 03 | 2,5500000E − 03 | 2,5800000E − 03 | 2,6100000E − 03 |
| 4568 | 2189 | 1 | 2,3200000E − 03 | 2,3133333E − 03 | 2,2500000E − 03 | 2,3100000E − 03 | 2,3800000E − 03 |
| 4560 | 2192 | 1 | 2,2300000E − 03 | 2,1933333E − 03 | 2,1500000E − 03 | 2,1600000E − 03 | 2,2700000E − 03 |
| 4540 | 2202 | 1 | 2,0200000E − 03 | 1,9966667E − 03 | 2,0000000E − 03 | 1,9800000E − 03 | 2,0100000E − 03 |
| 4504 | 2220 | 1 | 2,3400000E − 03 | 2,3133333E − 03 | 2,2900000E − 03 | 2,2900000E − 03 | 2,3600000E − 03 |
| 4472 | 2236 | 1 | 3,2300000E − 03 | 3,2000000E − 03 | 3,1500000E − 03 | 3,1900000E − 03 | 3,2600000E − 03 |
| 4440 | 2252 | 1 | 6,1400000E − 03 | 6,0966667E − 03 | 6,0800000E − 03 | 6,0600000E − 03 | 6,1500000E − 03 |
| 4432 | 2256 | 1 | 7,8000000E − 03 | 7,8100000E − 03 | 7,7800000E − 03 | 7,7700000E − 03 | 7,8800000E − 03 |
| 4424 | 2260 | 1 | 1,0270000E − 02 | 1,0210000E − 02 | 1,0180000E − 03 | 1,0190000E − 02 | 1,0260000E − 02 |
| 4416 | 2261 | 1 | 1,3160000E − 02 | 1,3130000E − 02 | 1,3100000E − 02 | 1,3090000E − 02 | 1,3200000E − 02 |
| 4408 | 2268 | 1 | 1,6510000E − 02 | 1,6490000E − 02 | 1,6430000E − 02 | 1,6470000E − 02 | 1,6570000E − 02 |
| 4400 | 2272 | 1 | 1,9410000E − 02 | 1,9386667E − 02 | 1,9340000E − 02 | 1,9350000E − 02 | 1,9470000E − 02 |
| 4392 | 2276 | 1 | 2,0970000E − 02 | 2,0963333E − 02 | 2,0930000E − 02 | 2,0940000E − 02 | 2,1020000E − 02 |
| 4382 | 2282 | 1 | 2,1900000E − 02 | 2,1913333E − 02 | 2,1870000E − 02 | 2,1930000E − 02 | 2,1940000E − 02 |
| 4376 | 2285 | 1 | 2,2570000E − 02 | 2,2530000E − 02 | 2,2510000E − 02 | 2,2520000E − 02 | 2,2560000E − 02 |
| 4368 | 2289 | 1 | 2,3080000E − 02 | 2,3053333E − 02 | 2,3030000E − 02 | 2,3030000E − 02 | 2,3100000E − 02 |
| 4352 | 2297 | 1 | 2,8240000E − 02 | 2,8183333E − 02 | 2,8170000E − 02 | 2,8160000E − 02 | 2,8220000E − 02 |
| 4344 | 2302 | 1 | 3,3140000E − 02 | 3,3196667E − 02 | 3,3230000E − 02 | 3,3220000E − 02 | 3,3140000E − 02 |
| 4330 | 2309 | 1 | 3,8690000E − 02 | 3,8780000E − 02 | 3,8850000E − 02 | 3,8810000E − 02 | 3,8680000E − 02 |
| 4320 | 2314 | 1 | 3,4290000E − 02 | 3,4320000E − 02 | 3,4360000E − 02 | 3,4300000E − 02 | 3,4300000E − 02 |
| 4312 | 2319 | 1 | 2,0890000E − 02 | 3,0883333E − 02 | 3,0830000E − 02 | 3,0870000E − 02 | 3,0950000E − 02 |
| 4304 | 2323 | 1 | 2,8580000E − 02 | 2,8576667E − 02 | 2,8560000E − 02 | 2,8560000E − 02 | 2,8610000E − 02 |
| 4296 | 2327 | 1 | 2,6340000E − 02 | 2,6386667E − 02 | 2,6340000E − 02 | 2,6400000E − 02 | 2,6420000E − 02 |
| 4290 | 2331 | 1 | 2,5250000E − 02 | 2,5223333E − 02 | 2,5200000E − 02 | 2,5230000E − 02 | 2,5240000E − 02 |
| 4280 | 2336 | 1 | 2,5760000E − 02 | 2,5786667E − 02 | 2,5800000E − 02 | 2,5780000E − 02 | 2,5780000E − 02 |
| 4272 | 2340 | 1 | 2,8200000E − 02 | 2,8263333E − 02 | 2,8300000E − 02 | 2,8290000E − 02 | 2,8300000E − 02 |
| 4258 | 2348 | 1 | 3,2280000E − 02 | 3,2410000E − 02 | 3,2500000E − 02 | 3,2470000E − 02 | 3,2260000E − 02 |
| 4248 | 2354 | 1 | 3,9760000E − 02 | 2,9810000E − 02 | 2,9870000E − 02 | 2,9820000E − 02 | 2,9740000E − 02 |
| 4240 | 2358 | 1 | 2,7120000E − 02 | 2,7133333E − 02 | 2,7120000E − 02 | 2,7170000E − 02 | 2,7110000E − 02 |
| 4232 | 2362 | 1 | 2,5410000E − 02 | 2,5393333E − 02 | 2,5410000E − 02 | 2,5410000E − 02 | 2,5360000E − 02 |
| 4224 | 2367 | 1 | 2,3930000E − 02 | 2,4000000E − 02 | 2,4000000E − 02 | 2,4020000E − 02 | 2,3980000E − 02 |
| 4212 | 2374 | 1 | 2,2630000E − 02 | 2,2630000E − 02 | 2,2680000E − 02 | 2,2650000E − 02 | 2,2560000E − 02 |
| 4200 | 2380 | 1 | 2,2060000E − 02 | 2,2106667E − 02 | 2,2140000E − 02 | 2,2160000E − 02 | 2,2020000E − 02 |
| 4192 | 2385 | 1 | 2,2010000E − 02 | 2,2043333E − 02 | 2,2110000E − 02 | 2,2070000E − 02 | 2,1950000E − 02 |
| 4184 | 2390 | 1 | 2,2220000E − 02 | 2,2226667E − 02 | 2,2310000E − 02 | 2,2230000E − 02 | 2,2140000E − 02 |
| 4176 | 2394 | 1 | 2,2780000E − 02 | 2,2816667E − 02 | 2,2860000E − 02 | 2,2840000E − 02 | 2,2750000E − 02 |
| 4170 | 2398 | 1 | 2,3160000E − 02 | 2,3213333E − 02 | 2,3290000E − 02 | 2,3210000E − 02 | 2,3140000E − 02 |
| 4160 | 2403 | 1 | 2,2840000E − 02 | 2,2850000E − 02 | 2,2890000E − 02 | 2,2860000E − 02 | 2,2800000E − 02 |
| 4152 | 2408 | 1 | 2,1510000E − 02 | 2,1843333E − 02 | 2,1900000E − 02 | 2,1860000E − 02 | 2,1770000E − 02 |
| 4136 | 2417 | 1 | 2,0630000E − 02 | 2,0630000E − 02 | 2,0700000E − 02 | 2,0640000E − 02 | 2,0550000E − 02 |
| 4120 | 2427 | 1 | 2,0170000E − 02 | 2,0186667E − 02 | 2,0240000E − 02 | 2,0220000E − 02 | 2,0100000E − 02 |
| 4104 | 2436 | 1 | 1,9520000E − 02 | 1,9563333E − 02 | 1,9590000E − 02 | 1,9590000E − 02 | 1,9510000E − 02 |
| 4092 | 2443 | 1 | 1,9530000E − 02 | 1,9593333E − 02 | 1,9640000E − 02 | 1,9610000E − 02 | 1,9530000E − 02 |
| 4080 | 2450 | 1 | 2,1540000E − 02 | 2,1513333E − 02 | 2,1550000E − 02 | 2,1530000E − 02 | 2,1460000E − 02 |
| 4072 | 2455 | 1 | 2,3530005E − 02 | 2,3530000E − 02 | 2,3550000E − 02 | 2,3530000E − 02 | 2,3510000E − 02 |
| 4068 | 2458 | 1 | 2,3430000E − 02 | 2,3443333E − 02 | 2,3460000E − 02 | 2,3450000E − 02 | 2,3420000E − 02 |
| 4048 | 2470 | 1 | 1,8990000E − 02 | 1,9010000E − 02 | 2,9050000E − 02 | 1,9020000E − 02 | 1,8960000E − 02 |
| 4000 | 2500 | 1 | 1,4630000E − 02 | 1,4593333E − 02 | 1,4620000E − 02 | 1,4580000E − 02 | 1,4580000E − 02 |
| Density kg/l | | | 0.9348 | 0.9351 | 0.9350 | 0.9345 | 0.9360 |
| Sulphur % | | | 2.25 | 2.28 | 2.37 | 1.98 | 2.51 |
| PCA % | | | 2.60 | 2.57 | 2.88 | 2.74 | 2.1 |
| Viscosity at 100° C. sCt | | | 33.19 | 33.22 | 33.23 | 32.25 | 34.18 |
| Flashpoint Cleveland ° C. | | | 310 | 311 | 310 | 208 | 315 |

TABLE 17.1

Determination of the properties of a crude paraffin

| | | Loading | Gatsche D Measured | Gatsche D Estimated | Gatsche 17A $6.76 \times 10^{-6}$ | Gatsche 17B Proximity Index $4.6 \times 10^{-6}$ | Gatsche 17C $2.69 \times 10^{-6}$ |
|---|---|---|---|---|---|---|---|
| Wavelength | | | | | | | |
| $\lambda$ (cm-1) | $\lambda$ (nm) | | | | | | |
| 4680 | 2136 | 1 | 7,0000000E − 05 | 8,0000000E − 05 | 8,0000000E − 05 | 8,0000000E − 05 | 8,0000000E − 05 |
| 4664 | 2144 | 1 | 1,9000000E − 04 | 1,4666667E − 04 | 1,2000000E − 04 | 2,0000000E − 04 | 1,2000000E − 04 |
| 4656 | 2147 | 1 | 3,0000000E − 04 | 7,6666667E − 05 | 1,0000000E − 04 | 6,0000000E − 05 | 7,0000000E − 05 |
| 4648 | 2151 | 1 | 2,7000000E − 04 | 1,6333333E − 04 | 1,9000000E − 04 | 1,4000000E − 04 | 1,6000000E − 04 |
| 4624 | 2162 | 1 | 1,9000000E − 04 | 3,0333333E − 04 | 4,1000000E − 04 | 2,4000000E − 04 | 2,6000000E − 04 |
| 4616 | 2166 | 1 | 4,3000000E − 04 | 2,0333333E − 04 | 4,1000000E − 04 | 1,0000000E − 04 | 1,0000000E − 04 |
| 4600 | 2173 | 1 | 4,0000000E − 04 | 3,4333333E − 04 | 3,6000000E − 04 | 3,0000000E − 04 | 3,7000000E − 04 |
| 4592 | 2177 | 1 | 5,3000000E − 04 | 3,9333333E − 04 | 3,8000000E − 04 | 4,0000000E − 04 | 4,0000000E − 04 |
| 4576 | 2185 | 1 | 7,7000000E − 04 | 3,0000000E − 04 | 3,0000000E − 04 | 2,9000000E − 04 | 3,1000000E − 04 |
| 4568 | 2189 | 1 | 8,1000000E − 04 | 3,5333333E − 04 | 5,5000000E − 04 | 2,5000000E − 04 | 2,6000000E − 04 |
| 4560 | 2192 | 1 | 4,0000000E − 04 | 4,1000000E − 04 | 6,4000000E − 04 | 2,0000000E − 04 | 3,0000000E − 04 |
| 4540 | 2202 | 1 | 6,1000000E − 04 | 4,9666667E − 04 | 4,7000000E − 04 | 5,2000000E − 04 | 5,0000000E − 04 |
| 4504 | 2220 | 1 | 8,9000000E − 04 | 7,3666667E − 04 | 7,9000000E − 04 | 7,2000000E − 04 | 7,0000000E − 04 |
| 4472 | 2236 | 1 | 1,3800000E − 04 | 1,2533333E − 03 | 1,3500000E − 03 | 1,2100000E − 03 | 1,2000000E − 03 |
| 4440 | 2252 | 1 | 3,2900000E − 03 | 3,0766667E − 03 | 3,1900000E − 03 | 3,0400000E − 03 | 3,0000000E − 03 |
| 4432 | 2256 | 1 | 4,0600000E − 03 | 4,1500000E − 03 | 4,1900000E − 03 | 4,1400000E − 03 | 4,1200000E − 03 |
| 4424 | 2260 | 1 | 5,5800000E − 03 | 5,4933333E − 03 | 5,5500000E − 03 | 5,5500000E − 03 | 5,3800000E − 03 |
| 4416 | 2264 | 1 | 7,3800000E − 03 | 7,4700000E − 03 | 7,3900000E − 03 | 7,6000000E − 03 | 7,4200000E − 03 |
| 4408 | 2268 | 1 | 9,9510000E − 03 | 9,9533333E − 03 | 9,8500000E − 03 | 1,0010000E − 02 | 1,0000000E − 02 |
| 4400 | 2272 | 1 | 1,2390000E − 02 | 1,2430000E − 02 | 1,2420000E − 02 | 1,2440000E − 02 | 1,2430000E − 02 |
| 4392 | 2276 | 1 | 1,3630000E − 02 | 1,3890000E − 02 | 1,3740000E − 02 | 1,3900000E − 02 | 1,4030000E − 02 |
| 4382 | 2282 | 1 | 1,5770000E − 02 | 1,5903333E − 02 | 1,5730090E − 02 | 1,6050000E − 02 | 1,5930000E − 02 |
| 4376 | 2285 | 1 | 1,7070000E − 02 | 1,7346667E − 02 | 1,7260000E − 02 | 1,7520000E − 02 | 1,7260000E − 02 |
| 4368 | 2289 | 1 | 1,8580000E − 02 | 1,6422000E − 02 | 1,1856000E − 02 | 1,8760000E − 02 | 1,8650000E − 02 |
| 4352 | 2297 | 1 | 2,7390000E − 02 | 2,7546667E − 02 | 2,7510000E − 02 | 2,7420000E − 02 | 2,7710000E − 02 |
| 4344 | 2302 | 1 | 3,6750000E − 02 | 3,7120000E − 02 | 3,7070000E − 02 | 3,7120000E − 02 | 3,7170000E − 02 |
| 4330 | 2309 | 1 | 4,8280000E − 02 | 4,8853333E − 02 | 4,8950000E − 02 | 4,8810000E − 02 | 4,8800000E − 02 |
| 4320 | 2314 | 1 | 3,3850000E − 02 | 3,4233333E − 02 | 3,3910000E − 02 | 3,4130000E − 02 | 3,4660000E − 02 |
| 4312 | 2319 | 1 | 2,5770000E − 02 | 2,5913333E − 02 | 2,5860000E − 02 | 2,5900000E − 02 | 2,5980000E − 02 |
| 4304 | 2323 | 1 | 2,2440000E − 02 | 2,2740000E − 02 | 2,2410000E − 02 | 2,2710000E − 02 | 2,3100000E − 02 |
| 4296 | 2327 | 1 | 2,1050000E − 02 | 2,1210000E − 02 | 2,1110000E − 02 | 2,1260000E − 02 | 2,1260000E − 02 |
| 4290 | 2331 | 1 | 2,1120000E − 02 | 2,1233333E − 02 | 2,1130000E − 02 | 2,1260000E − 02 | 2,1310000E − 02 |
| 4280 | 2336 | 1 | 2,4680000E − 02 | 2,4666667E − 02 | 2,4510000E − 02 | 2,4760000E − 02 | 2,4730000E − 02 |
| 4272 | 2340 | 1 | 3,1630000E − 02 | 3,1763333E − 02 | 3,1700000E − 02 | 3,1840000E − 02 | 3,1750000E − 02 |
| 4258 | 2348 | 1 | 4,5820000E − 02 | 4,6073333E − 02 | 4,6130000E − 02 | 4,6110000E − 02 | 4,5980000E − 02 |
| 4248 | 2354 | 1 | 3,2680000E − 02 | 3,2866667E − 02 | 3,2780000E − 02 | 3,2860000E − 02 | 3,2960000E − 02 |
| 4240 | 2358 | 1 | 2,6170000E − 02 | 2,6273333E − 02 | 2,6060000E − 02 | 2,6260000E − 02 | 2,6500000E − 02 |
| 4232 | 2362 | 1 | 2,5370000E − 02 | 2,5383333E − 02 | 2,5330000E − 02 | 2,5410000E − 02 | 2,5410000E − 02 |
| 4224 | 2367 | 1 | 2,6390000E − 02 | 2,6493333E − 02 | 2,6390000E − 02 | 2,6520000E − 02 | 2,6570000E − 02 |
| 4212 | 2374 | 1 | 2,6780000E − 02 | 2,6876667E − 02 | 2,6850000E − 02 | 2,6890000E − 02 | 2,6890000E − 02 |
| 4200 | 2380 | 1 | 2,7840000E − 02 | 2,7633333E − 02 | 2,7610000E − 02 | 2,7640000E − 02 | 2,7650000E − 02 |
| 4192 | 2385 | 1 | 2,8190000E − 02 | 2,8150000E − 02 | 2,8210000E − 02 | 2,8140000E − 02 | 2,8100000E − 02 |
| 4184 | 2390 | 1 | 2,8030000E − 02 | 2,8146667E − 02 | 2,8210000E − 02 | 2,8030000E − 02 | 2,8200000E − 02 |
| 4176 | 2394 | 1 | 2,8540000E − 02 | 2,8663333E − 02 | 2,8730000E − 02 | 2,8600000E − 02 | 2,8660000E − 02 |
| 4170 | 2398 | 1 | 2,8970000E − 02 | 2,9000000E − 02 | 2,8960000E − 02 | 2,9010000E − 02 | 2,9030000E − 02 |
| 4160 | 2403 | 1 | 2,8410000E − 02 | 2,8526667E − 02 | 2,8550000E − 02 | 2,8480000E − 02 | 2,8550000E − 02 |
| 4152 | 2408 | 1 | 2,7870000E − 02 | 2,7740000E − 02 | 2,7670000E − 02 | 2,7760000E − 02 | 2,7790000E − 02 |
| 4136 | 2417 | 1 | 2,6790000E − 02 | 2,6840000E − 02 | 2,6860000E − 02 | 2,6810000E − 02 | 2,6850000E − 02 |
| 4120 | 2427 | 1 | 2,5720000E − 02 | 2,5660000E − 02 | 2,5660000E − 02 | 2,5660000E − 02 | 2,5660000E − 02 |
| 4104 | 2436 | 1 | 2,4570000E − 02 | 2,4506667E − 02 | 2,4510000E − 02 | 2,4420000E − 02 | 2,4590000E − 02 |
| 4092 | 2443 | 1 | 2,4010000E − 02 | 2,3953333E − 02 | 2,3970000E − 02 | 2,3910000E − 02 | 2,3980000E − 02 |
| 4080 | 2450 | 1 | 2,3920000E − 02 | 2,4056667E − 02 | 2,4130000E − 02 | 2,3970000E − 02 | 2,4070000E − 02 |
| 4072 | 2455 | 1 | 2,4550000E − 02 | 2,4480000E − 02 | 2,4580000E − 02 | 2,4410000E − 02 | 2,4450000E − 02 |
| 4068 | 2458 | 1 | 2,4530000E − 02 | 2,4540000E − 02 | 2,4580000E − 02 | 2,4480000E − 02 | 2,4560000E − 02 |
| 4048 | 2470 | 1 | 2,0460000E − 02 | 2,0390000E − 02 | 2,0480000E − 02 | 2,0240000E − 02 | 2,0450000E − 02 |
| 4000 | 2500 | 1 | 1,5750000E − 02 | 1,5656667E − 02 | 1,5660000E − 02 | 1,5650000E − 02 | 1,5860000E − 02 |
| Density kg/l | | | 0.8901 | 0.8904 | 0.8898 | 0.8900 | 0.8915 |
| Viscosity at 100° C. sCt | | | 8.07 | 8.03 | 7.80 | 8.15 | 8.15 |
| Oil Content % | | | 28 | 27.8 | 26.9 | 25.75 | 31.0 |

We claim:

1. A method of determining or predicting a value $P_x$ which is a value of a property of a material X or a property of a product of a process from said material or yield of said process, which method comprises measuring the absorption $D_{ix}$ of said material at more than one wavelength in the region 600–2600 nm, comparing said signals indicative of said absorptions or a mathematical function thereof with signals indicative of absorptions $D_im$ at the same wavelengths or a mathematical function thereof for a number of standards S in a bank for which said property or yield P is known, and choosing from the bank at least one standard $S_m$ with property $P_m$ said standard having the smallest average value of the absolute difference at each wavelength i between the signal for the material and the signal for the standard $S_m$ to obtain $P_x$, with averaging of said properties or yields $P_m$ when more than one standard $S_m$ is chosen.

2. A method according to claim 1 comprising comparing absorptions $D_ix$ (or a derivative thereof) with absorption $D_im$ or a derivative thereof.

3. A method according to claim 2 wherein the standard $S_m$ chosen for the property or yield wanted is such that in relation to the unknown material X and each chosen standard $S_m$ the following function is met when $i_{xm} < i_{min}$ then $P_x - P_m \leq$ experimental error in P where $P_x$ is property of unknown X, $P_m$ is property of chosen standard $S_m$, $i_{xm}$ is defined by $i^2(xm) = \Sigma(D_{ix} - D_{im})^2$ and the $i_{min}$ is defined by the proximity index, which is the minimum value in relation to 2 standards Sa and Sb with properties $P_a$ and $P_b$, for which $P_a - P_b < E\sqrt{2}$, where E is the experimental error in determining said property or yield in the standard.

4. A method according to claim 3 wherein the proximity index is less than or equal to the minimal index $i_m$ which has been determined from the standards Sa, Sb, Sc . . . by (a) calculating for each pair of standards Sa/Sb, Sa/Sc the value of $i^2(a,b)$ etc, (b) relating the values of $i^2(a,b)$ etc to the corresponding differences EP (ab) in properties Pa, Pb etc (c) calculating for each value L for which $i^2(ab)$ is $\leq L$, the average of the corresponding differences EPab, (d) calculating Minimal index from the value of minimal index $i^2(ab)$ where average EPab is the same as reproducibility standard for the property.

5. A method according to claim 1, wherein the properties of synthetic standards, which are mixtures, and their spectra for consideration for possible choice for Sm are estimated from existing standards in the bank for which, in respect of each existing standard for use in said mixture equation (4) and (5) are met, $$(Min)C_j - u_j \leq C_{ij} \leq (Max)C_j + u_j \quad (4)$$

$$\text{and } \Sigma C_{ij} = 1 \quad (5)$$

wherein $C_{ij}$ is fraction of component j in the sample i,
Min Cj is the minimum of j in the standards in the bank or in the samples for which the method is to be used, and
Max Cj is the maximum of j in the standards in the bank or in the samples for which the method is to be used and uj is between 1.0 and 0.05.

6. A method according to claim 5 wherein at least one of (i) the estimated Standards and the corresponding spectra, and (ii) the property $P_X$ of the unknown material and its spectrum, are added to the bank.

7. A method according to claim 1 wherein properties of Standards and spectra for consideration for possible choice are estimated by interpolation from measured properties of Standards and spectra for which the proximity index with respect to the unknown X is not more than 10 times the Minimal Index.

8. A method according to claim 1 wherein the property $P_X$ or yield is compared to the desired value and any deviations used in a closed loop control system to control the processing equipment in relation to a process for which the material is a product or a feed.

9. A method according to claim 1 wherein the property is a physicochemical property of material X.

10. A method according to claim 1 wherein the property is a physicochemical property or yield of a product of a process to which at least one material X is a feed.

11. A method according to claim 1 wherein said process is a hydrocarbon conversion or separation process, preferably a reforming or catalytic cracking or hydrotreatment, or distillation or blending.

12. A method according to claim 11 wherein said property is in respect of a feed to a reforming process and is at least one of percentages of saturated linear, isoparaffins, napthenics, and aromatics and density.

13. A method according to claim 11 wherein said property is in respect of a feed to a fluid catalytic cracking unit and is at least one of the density, the weight percentage of sulphur, the aniline point, viscosity at 100° C., refractive index at 20° C. or 60° C., 50% distillation point, molecular weight, percentage of aromatic carbon and the KUOP, crackability or cokability of the feed or yield of gas, gasoline, gas oil or residue.

14. A method according to claim 11 wherein said percentage is in respect of the feed to a hydrogenation unit and is at least one of percentages of linear saturation, isoparaffins, napthenes, linear olefins, cyclic olefins, benzene, toluene, xylene, alkylbenzene, density, or yield of light cut, heavy cut, or raffinate or benzene.

15. A method according to claim 1 wherein said process is a distillation to give at least 1 distillation product and a residue and the properties/yields are obtained in respect of said product and/or residue.

16. A method according to claim 1 wherein said property is in respect of a motor fuel and is at least one of an Octane Number, vapour pressure, volatility percentage distilled at 70 and at 100° C., gum content in mg/100 ml and content of sulphur, benzene or methyl tert. butyl ether.

17. A method according to claim 16 wherein the property is in respect of a blend comprising gasoline, the spectra are measured on feeds to said blending, and by calculation the blend index obtained as a linear or non linear function.

18. A method according to claim 1 wherein said property is in respect of gas oil and is at least one of cetane index, cetane number, percentage of sulphur, density at 15° C., clear point, cloud point, filterability and viscosity at 40° C.

19. A method according to claim 1 wherein said property is in respect of a crude oil and is at least one of density, percentage of sulphur, viscosity at 100° C., content of paraffin and residual carbon percentage (Conradson Carbon).

20. A method according to claim 1 wherein said process is at least one of a polymerization, an oligomerization or an organic reaction in which at least one of the reactant and a product is a functionalized compound.

21. A method according to claim 20 wherein said process is a polymerization.

22. A method according to claim 21 which is an addition polymerization of at least one unsaturated hydrocarbon, and the property is at least one of number and weight average molecular weight, molecular weight distribution, viscosity, viscosity index, fluidity index, density, chemical composition such as percentage of at least one monomer, or unsaturation or side chain group, crystallinity, rigidity, a flow property, draw strength at the flow threshold, cracking resistance and shock resistance.

23. A method according to claim 22, wherein the process is a polymerization of at least one alpha olefin of 2–8 carbons and the property is of the product and is at least one of the density, fluidity index, degree of conversion, content of volatiles and, in the case of copolymerization percentage of comonomer.

24. A method according to claim 20 wherein the process is a reaction in which at least one of a reactant and product is a functionalized compound, and is a hydration, dehydration, etherification, esterification, oxidation, ammoxidation or carbonylation.

25. A method according to claim 21 wherein the process is the polymerization reaction of an epoxide in the presence of an organic compound containing at least one hydroxy group and the property is at least one of the degree of conversion, and of the product, hydroxyl index, viscosity and molecular weight.

26. A method according to claim 22 wherein the process is a polymerization of isobutene and the property is of the product and is at least one of the viscosity, number average molecular weight, distribution of molecular weights, inflammability point, content of butene 1 unsaturation and maleinization index, and percentage of light and heavy fractions from distillation of the direct product of the process.

27. A method according to claim 1 wherein said material X is a composition comprising part of a lubricating oil fraction obtainable from a vacuum distillation of oil.

28. A method according to claim 27 wherein said material comprises at least one of a lube base oil, bright stock, process oil, wax and paraffin.

29. A method according to claim 27, wherein the property is of the material, which is (i) a base oil and the property is at least one of the density, viscosity, Viscosity Index, Flash Point, Pour Point, and the content of sulphur, nitrogen base, aromatic carbon and Polycyclic aromatic hydrocarbon, (ii) a wax or paraffin or mixture thereof with a base oil and the property is at least one of the density, viscosity and base oil content or (iii) a process oil and the property is at least one of the density, clear point, viscosity and content of sulphur or polycyclic aromatic hydrocarbon.

30. A method according to claim 29 wherein the property is of a finished lubricating oil which comprises at least one non hydrocarbon additive.

31. A method according to claim 1 which is computer implemented.

32. A computer implemented method according to claim 31 involving a spectrometer linked to a process line containing a material X, a computer linked to the spectrometer, and a controller linked to the computer and the process line, the computer including databanks having stored therein signals indicative of absorptions of standard materials or mathematical functions thereof, and corresponding properties of said materials, or products of said process of which X is a feed or yield of said process, the method comprises steps of:

measuring absorption at more than one wavelength in the region 600–2600 nm at the process line and producing absorption signals or mathematical functions thereof, by the spectrometer in accordance therewith;

accessing the databanks of the computer in accordance with the absorption signals or functions thereof;

comparing, by the computer, the absorption signals or functions thereof to the signals or functions thereof of the standard materials stored in the databanks;

choosing at least one standard based on the comparing, said standard having the smallest average value of the absolute difference at each wavelength i between the signal (or function thereof) for the material and the signal (or function thereof) for the standards, with averaging of said properties or yields when more than one standard is chosen; and controlling said process in accordance with the outputted property/yield.

33. A computer programmed to perform the method of claim 1.

34. Apparatus suitable for use in the method of claim 1 which comprises an NIR spectrometer receiving at least one signal from a feed or product line in said process and being coupled to a computer to effect continuous measurement of the spectra of the feed and/or product and provide feed back control of the process.

35. Method of controlling a process for which a material X is a feed or a product, in order to keep substantially constant the value $V_c$ of a property P of said product or the product of said process from said feed, or the yield of said process, which method comprises measuring the absorption $D_{ix}$ of said material at more than one wavelength in the region 600–2600 nm, comparing signals (i) indicative of said absorptions or a mathematical function thereof with signals (ii) indicative of absorptions $D_{im}$ at the same wavelengths or a mathematical function thereof for at least 2 standards $S_m$ for which said property or yield has a known value V, at least one of said standards $S_{mc}$ having a value $V_c$ for said property or yield and controlling said process to ensure that said standard $S_{mc}$ or standard(s) $S_{mc}$ is the standard or standards having the smaller or smallest average value of the absolute difference at each wavelength i between the signal for said material and the signal from the standard $S_m$.

36. A method according to claim 35 which comprises comparing signals (i) from said material with signals (ii) from standards $S_m$, at least 2 of which have smallest average values of the differences, and the average of the values V of the property of yield of said at least 2 standards being $V_c$.

37. A method according to claim 35 comprising comparing absorptions $D_ix$ (or a derivative thereof) with absorption $D_im$ or a derivative thereof.

38. A method according to claim 35 wherein the standard $S_{mc}$ is such that in relation to the material X and the or each standard $S_{mc}$ the following function is met when $i_{xm} < i_{min}$ then $P_x - P_m \leq$ experimental error in P where $P_x$ is property of unknown X, $P_m$ is property of chosen standard $S_m$, $i_{xm}$ is defined by $i^2(xm) = \Sigma(D_{ix} - D_{im})^2$ and the $i_{min}$ is defined by the proximity index, which is the minimum value in relation to 2 standards Sa and Sb with properties $P_a$ and $P_b$ for which $P_a - P_b < E\sqrt{2}$, where E is the experimental error in determining said property or yield in the standard.

39. A modification of a method according to claim 38 wherein the comparison of signals (i) is with signals (ii) indicative of absorptions $D_{im}$ at the same wavelength or a mathematical function thereof of one standard $S_{mc}$ having the known value $V_c$ of said property or yield and controlling said process to ensure that the function specified in claim 7 is met.

40. A method according to claim 38 wherein the proximity index is less than or equal to the minimal index $i_m$ which has been determined form the standards Sa, Sb, Sc . . . by (a) calculating for each pair of standards Sa/Sb, Sa/Sc the value of $i^2(a,b)$ etc, (b) relating the values of $i^2(a,b)$ etc to the corresponding differences EP (ab) in properties Pa, Pb etc (c) calculating for each value L for which $i^2(a,b)$ is $\leq L$, the average of the corresponding differences EPab, (d) calculating Minimal index from the value of minimal index (ab) where 95% of EPab is the same as reproducibility standard for the property.

41. A method according to claim 35 wherein the process is controlled in a closed loop control system to control the process equipment in relation to a process for which the material X is a product.

42. A method according to claim 35 which is computer implemented.

43. A method according to claim 35 wherein said process is a hydrocarbon conversion or separation process, preferably a reforming or catalytic cracking or hydrotreatment, or distillation or blending.

44. A method according to claim 35 wherein said process is at least one of a polymerization, an oligomerization or an organic reaction in which at least one of the reactant and a product is a functionalized compound.

45. A method according to claim 35 wherein said material X is a composition comprising part of a lubricating oil fraction obtainable from a vacuum distillation of oil.

46. A method for adding an extra synthetic standard to a bank of known standards, each of which relates at least one absorption in the 600–2600 nm region (or signal indicative thereof or mathematical function of said absorption) of a known material to a known property related to that material, which property is of said material which is a feed to a process, or is of a product from said process or yield of said process, which method comprises choosing from the bank at least 2 standards for which equations 4 and 5 as defined below are met, $$(Min)Cj-uj \leq Cij \leq (Max)Cj+uj \quad (4)$$

$$\text{and } \Sigma Cij=1 \quad (5)$$

wherein Cij is fraction of component j in the sample i,
Min Cj is the minimum of j in the standards in the bank or in the samples for which the method is to be used, and
Max Cj is the maximum of j in the standards in the bank or in the samples for which the method is to be used and uj is between 1.0 and 0.05, considering mixing the chosen standards in at least one proportion to produce at least one mixture for use in a synthetic standard, and estimating the spectrum of said mixture according to equation 6, $$S_{Mi} = \Sigma C_{ij} X S_j \quad (6)$$

where $S_j$ is the spectrum in the mixture of component j in the calibration matrix, and estimating a property of said mixture according to equation 7

$$P_{Mi} = \Sigma C_{ij} X P_j \quad (7)$$

where Pj is the property of component j,
and then adding the spectrum and property of each "mixture" to the bank, and using them in at least one model involving a correlation/regression approach to relate NIR spectra to at least one property.

* * * * *